US011135309B2

(12) United States Patent
Lam et al.

(10) Patent No.: US 11,135,309 B2
(45) Date of Patent: Oct. 5, 2021

(54) POLY(VINYL ALCOHOL) NANOCARRIERS

(71) Applicant: THE REGENTS OF THE UNIVERSITY OF CALIFORNIA, Oakland, CA (US)

(72) Inventors: Kit S. Lam, Oakland, CA (US); Yuanpei Li, Oakland, CA (US); Kai Xiao, Oakland, CA (US); Caihong Feng, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/752,326

(22) PCT Filed: Aug. 15, 2016

(86) PCT No.: PCT/US2016/047097
§ 371 (c)(1),
(2) Date: Feb. 13, 2018

(87) PCT Pub. No.: WO2017/031084
PCT Pub. Date: Feb. 23, 2017

(65) Prior Publication Data
US 2018/0243442 A1    Aug. 30, 2018

Related U.S. Application Data

(60) Provisional application No. 62/205,402, filed on Aug. 14, 2015.

(51) Int. Cl.
*A61K 47/69* (2017.01)
*A61K 9/51* (2006.01)
*A61K 47/32* (2006.01)
*C08F 230/06* (2006.01)
*A61K 9/00* (2006.01)
*A61K 47/58* (2017.01)
*A61K 47/54* (2017.01)
*A61K 47/68* (2017.01)
*A61K 49/18* (2006.01)
*A61P 35/00* (2006.01)
*A61K 31/69* (2006.01)

(52) U.S. Cl.
CPC ........ *A61K 47/6933* (2017.08); *A61K 9/0019* (2013.01); *A61K 9/5138* (2013.01); *A61K 31/69* (2013.01); *A61K 47/32* (2013.01); *A61K 47/546* (2017.08); *A61K 47/547* (2017.08); *A61K 47/58* (2017.08); *A61K 47/6847* (2017.08); *A61K 47/6869* (2017.08); *A61K 49/1854* (2013.01); *A61P 35/00* (2018.01); *C08F 230/06* (2013.01)

(58) Field of Classification Search
None
See application file for complete search history.

(56) References Cited

U.S. PATENT DOCUMENTS

| 5,053,423 A | 10/1991 | Liu |
| 8,318,795 B2 | 11/2012 | Yu |
| 8,557,292 B2 | 10/2013 | Davis |
| 2006/0159736 A1* | 7/2006 | Zalipsky .............. A61K 9/0019 424/450 |
| 2009/0209508 A1* | 8/2009 | Lange .................... B82Y 5/00 514/185 |
| 2012/0322145 A1* | 12/2012 | Onofiok ................. C09J 129/04 435/325 |
| 2014/0161719 A1 | 6/2014 | Lam et al. |

FOREIGN PATENT DOCUMENTS

| CN | 104177548 A | 12/2014 |
| WO | 99/12577 | 3/1999 |
| WO | 2012153254 A1 | 11/2012 |

OTHER PUBLICATIONS

Jiang, F.N., et al., "Photodynamic Killing of Human Squamous Cell Carcinoma Cells Using a Monoclonal Antibody-Photosensitizer Conjugate", J. National Cancer Institute, pp. 1218-1225 (Year: 1991).*
Giuntini, F., et al., "Synthetic approaches for the conjugation of porphyrins and related macrocycles to peptides and proteins", Photochemical and Photobiological Sciences, pp. 759-791 (Year: 2011).*
Zhao, Z., et al., "Boronic Acid Shell-Crosslinked Dextran-b-PLA Micelles for Acid-Responsive Drug Delivery", Macromol. Biosci., pp. 1609-1618 (Year: 2014).*
United States Patent and Trademark Office, International Search Report and Written Opinion for PCT International Application No. PCT/US2016/047097, dated Oct. 31, 2016, 14 pages.
Drury et al., "Hydrogels for tissue engineering: scaffold design variables and applications", Biomaterials, 2003, vol. 24, pp. 4337-4351.
Li et al., "Reversibly crosslinked poly (vinyl alcohol) nanoparticles for triggered release of 1-5,6/2-5,9,11-15, doxorubicin", Journal of Controlled Release, 2011, vol. 152, abstract; scheme 1; e54-e55.

* cited by examiner

*Primary Examiner* — Michael G. Hartley
*Assistant Examiner* — Lance W Rider
(74) *Attorney, Agent, or Firm* — Mintz Levin Cohn Ferris Glovsky and Popeo, P.C.

(57) ABSTRACT

The present invention provides a nanoparticle including at least one poly(vinyl alcohol) (PVA) having a molecular weight of from about 10 kDa to about 200 kDa, substituted with one or more moieties selected from: a therapeutic agent having a boronic acid moiety, wherein the therapeutic agent is covalently linked to the PVA via a boronate ester bond; a crosslinking group having a disulfide moiety, wherein the crosslinking group is covalently linked to the PVA, and a porphyrin, wherein the porphyrin is covalently linked to the PVA. Use of the nanoparticles for tumor detection and the treatment of diseases, including methods for photodynamic therapy and photothermal therapy, are also described.

11 Claims, 41 Drawing Sheets

Optical imaging (PVA-LA-Cy5.5)

Orthotopic MDA-MB-231 breast cancer xenograft mouse model

POLY(VINYL ALCOHOL) NANOCARRIERS

CROSS-REFERENCES TO RELATED APPLICATIONS

The present application claims priority to U.S. Provisional Pat. Appl. No. 62/205,402, filed on Aug. 14, 2015, which application is incorporated herein by reference in its entirety.

STATEMENT AS TO RIGHTS TO INVENTIONS MADE UNDER FEDERALLY SPONSORED RESEARCH AND DEVELOPMENT

The present invention was made with government support from the National Institutes of Health under Grant Nos. 3R01CA115483 and R01EB012569. The United States government has certain rights to the invention.

BACKGROUND OF THE INVENTION

Nanotechnology is an emerging field that has shown promise for the development of novel diagnostic, imaging, and therapeutic agents for a variety of diseases, including cancer. The nanomaterials used for drug delivery include solid nanoparticles, liposomes, dendrimers, polymeric micelles, water soluble polymers, and protein aggregates. Nanoparticles offer several distinct advantages for these drugs, such as improved solubility, prolonged in vivo circulation time and preferential accumulation at tumor sites due to the enhanced permeability and retention exhibited by many tumor tissues. The optimal particle size of nanoparticles for passive tumor targeting has been reported to range from 10 to 100 nm. The enhanced accumulation of drugs in tumor tissue can result in increased therapeutic efficacy as well as a decrease in side effects. In order to successfully develop an effective nanotherapeutic, an agent must be associated with a suitable carrier (such as a nanoparticle) in a manner that does not inhibit its therapeutic or diagnostic activity. If the carrier is to include targeting groups that direct the drug to a desired location in a subject, such as a tumor, the targeting groups must also be linked to the carrier in a way that does not interfere with their ability to interact with the target. The identification and combination of drugs, carriers, and targeting agents to provide effective nanotherapeutics remains a challenge. Versatile platforms for efficiently combining these various components and testing the combinations are still needed. The present invention addresses this and other needs.

BRIEF SUMMARY OF THE INVENTION

In one embodiment, the present invention provides a nanoparticle including at least one poly(vinyl alcohol) (PVA) having a molecular weight of from about 10 kDa to about 200 kDa substituted with one or more moieties selected from:
  a therapeutic agent having a boronic acid moiety, wherein the therapeutic agent is covalently linked to the PVA via a boronate ester bond;
  a crosslinking group having a disulfide moiety, wherein the crosslinking group is covalently linked to the PVA, and
  a porphyrin, wherein the porphyrin is covalently linked to the PVA.
In some embodiments, the PVA has a structure according to formula I:

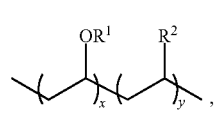

wherein:
each $R^1$ is independently selected from H and a moiety according to formula Ia:

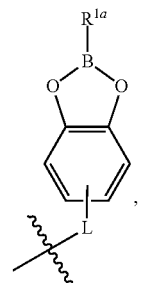

wherein L is a linking moiety and $R^{1a}$ is a therapeutic moiety, or
any two adjacent $R^1$ moieties are taken together with the oxygen atoms to which they are bound to form a moiety according to Formula Ib:

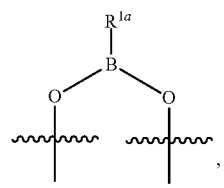

wherein $R^{1a}$ is a therapeutic moiety,
  provided that at least one $R^1$ is H and at least one $R^1$ is other than H;
each $R^2$ is independently selected from —OH, a cellular targeting moiety, and an imaging moiety, or any two adjacent $R^2$ moieties are taken together to form a cellular targeting moiety or an imaging moiety;
subscript x is an integer of from about 1 to about 1200, and
subscript y is an integer of from 0 to about 3800, wherein the sum of x and y is an integer of from about 200 to about 5000, and the x and y repeating units are randomly distributed in the PVA.
In some embodiments, the PVA has a structure according to formula II:

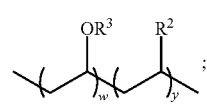

wherein
each $R^3$ is independently selected from H and a moiety -$L^3$-$R^{3a}$, wherein $L^3$ is a linking moiety and $R^{3a}$ is the disulfide moiety, provided that at least one $R^3$ is H and at least two $R^3$ are the moiety -$L^3$-$R^{3a}$;

each $R^2$ is independently selected from —OH, a cellular targeting moiety, and an imaging moiety, or any two adjacent $R^2$ moieties are taken together to form a cellular targeting moiety or an imaging moiety;

subscript w is an integer of from about 2 to about 1200, and subscript y is an integer of from 0 to about 3800, wherein the sum of w and y is an integer of from about 200 to about 5000, and the w and y repeating units are randomly distributed in the PVA.

In some embodiments, the PVA has a structure according to formula III:

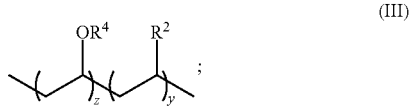

(III)

wherein each $R^4$ is independently selected from H and a moiety -$L^4$-$R^{4a}$, wherein $L^4$ is a linking moiety and $R^{4a}$ is the porphyrin, provided that at least one $R^4$ is H and at least one $R^4$ is the moiety -$L^4$-$R^{4a}$;

each $R^2$ is independently selected from —OH, a cellular targeting moiety, and an imaging moiety, or any two adjacent $R^2$ moieties are taken together to form a cellular targeting moiety or an imaging moiety;

subscript z is an integer of from about 1 to about 1200, and subscript y is an integer of from 0 to about 3800, wherein the sum of z and y is an integer of from about 200 to about 5000, and the z and y repeating units are randomly distributed in the PVA.

In some embodiments, the invention provides a method for treating a disease including administering a therapeutically effective amount of a nanoparticle of the invention to a subject in need thereof.

In some embodiments, the invention provides a method of treating a disease via photodynamic or photothermal therapy including administering to a subject in need thereof a therapeutically effective amount of a nanoparticle of the invention, wherein the nanoparticle has a porphyrin, and exposing the subject to radiation, thereby treating the disease via photodynamic or photothermal therapy.

In further embodiments, the invention provides a method of detecting a tumor in a subject including administering to the subject an effective amount of a nanoparticle of the invention and detecting the nanoparticle via fluorescence imaging, magnetic resonance imaging, or positron emission tomography.

BRIEF DESCRIPTION OF THE DRAWINGS

FIG. 13(C) shows the size of DOX loaded pre-crosslinked PVA-LA NPs.

FIG. 13(D) shows the size of DOX loaded crosslinked PVA-LA NPs.

DETAILED DESCRIPTION OF THE INVENTION

I. General

Figure 1:
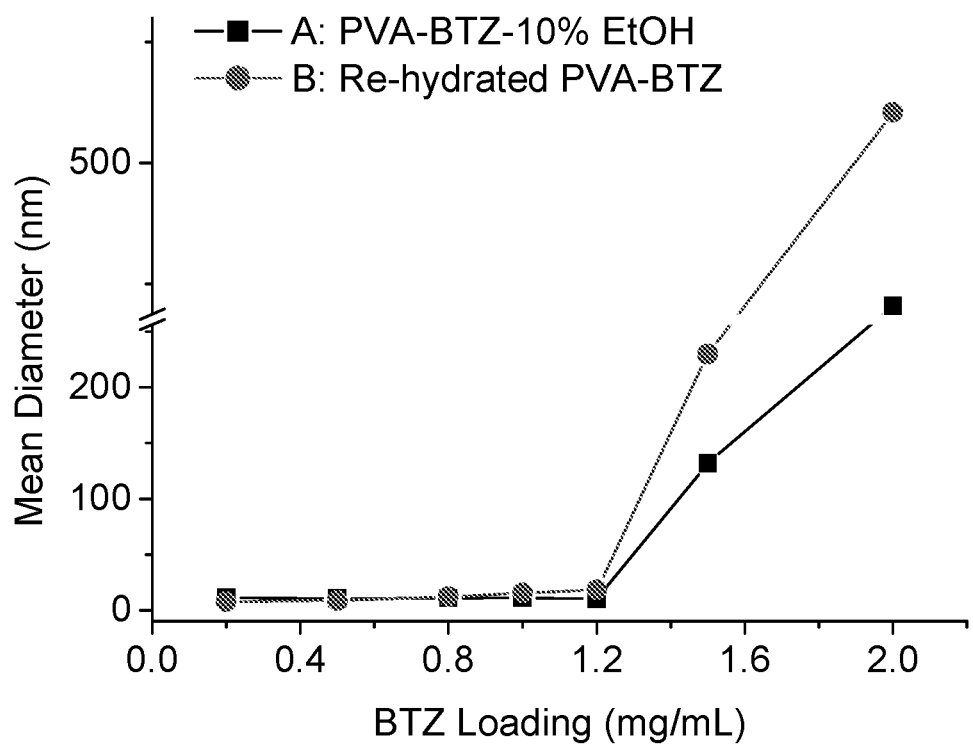
FIG. 1 shows the size of bortezomib-loaded PVA particles as assessed by dynamic light scattering.

The present invention provides nanoformulations based on polyvinyl alcohol (PVA) for targeted delivery of therapeutic and diagnostic agents to subjects in need thereof. Therapeutic agents, including porphyrins and boronic acid-containing drugs such as bortezomib, can be covalently linked to PVA nanoparticles. The PVA particles can be further stabilized by crosslinking via formation of boronate esters or disulfides. Ligands for cancer tissues or other cellular targets can be covalently conjugated to the PVA nanoparticles by utilizing Huisgen [3+2] cycloaddition with azides and alkynes or by forming boronate ester bonds. In certain embodiments, the PVA nanoparticles contain a redox-sensitive hydrophobic core for loading of hydrophobic drugs and subsequent release in the reducing environment of target tissues. PVA nanoparticles having fluorophores and chromophores, such as porphyrin groups, also demonstrate unique architecture-dependent fluorescence self-quenching and photothermal properties. These particles can provide for low-background fluorescence imaging, as well as tumor-specific magnetic resonance imaging, and imaging-guided photothermal therapy. The highly versatile nanoparticles exhibit useful multimodality for a variety of imaging and therapeutic applications.

II. DEFINITIONS

As used herein, the term "nanoparticle" refers to a polymeric particle with a diameter ranging from about 1 nm to about 1000 nm. The nanoparticles can have a symmetric or nearly symmetric shape such as a sphere or an ellipsoid, or the nanoparticles can have an irregular asymmetric shape. The nanoparticles of the invention can include one or more polymer chains that can be crosslinked by covalent or non-covalent inter-chain or intra-chain bonds. Polymer chains in the nanoparticle can also be associated with each other by physical entanglement.

As used herein, the terms "poly(vinyl alcohol)" and "PVA" refer to a polymer having repeating units with the formula —CH$_2$CH(OH)—. PVA is also referred to or marketed as ethenol homopolymer, Covol, Elvanol, Galvatol, Gohsenol, Lamicel, Mowiol, poly(1-hydroxyethylene), polyvinol, Polyviol, Poval, Vinarol, and Vinarol, among other commonly used names. PVA used in the present invention can be linear, branched, or dendritic. The molecular weight of the PVA can range from about 1000 Daltons (i.e., 1 kDa or 1000 g/mole) to several hundred kDa or more. The PVA can be chemically modified with therapeutic agents, imaging agents, cellular targeting agents, and other functional groups as described herein.

As used herein, the term "therapeutic agent" refers to any type of drug, medicine, pharmaceutical, hormone, antibiotic, protein, gene, growth factor, bioactive material, etc., used for treating, controlling, or preventing diseases or medical conditions.

As used herein, the term "boronic acid" refers to a functional group having the formula R—B(OH)$_2$, wherein R represents a substituted carbon atom. R can be, for example, a boronic acid-containing therapeutic agent such as bortezomib.

As used herein, the term "boronate ester" refers to a functional group having the formula R—B(OR')(OR''). R can be, but is not limited to, a boronic acid-containing therapeutic agent such as bortezomib, or a carbon atom of a therapeutic agent, an imaging moiety, a cellular targeting moiety, or a linking moiety. R' and R'' can each independently be, but are not limited to, C$_{1-6}$ alkyl and C$_{1-6}$ aryl. Boronate esters can also be formed with PVA such that R' and R'' represent adjacent PVA monomers as show below:

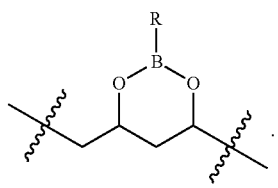

As used herein, the term "covalently linked" refers to two atoms which are bonded together by the sharing of at least one pair of electrons.

As used herein, the term "crosslinking group" refers to a bifunctional or multi-functional compound or moiety that reacts with one or more monomers in a first polymer chain and also with one or more monomers in a second polymer chain, thereby linking the first polymer chain and the second polymer chains together. A crosslinking group can also react with one or monomers in a polymer chain and also with additional monomers in the same polymer chain, thereby linking two different portions of the same polymer chain together. A crosslinking group can be homobifunctional group or a heterobifunctional group. Homobifunctional crosslinkers have two or more of the same reactive group for reaction with the polymers to be linked. Heterobifunctional crosslinkers have two or more different reactive groups for reaction with the polymers to be linked. Examples of crosslinking groups include—but are not limited to—disulfides, which can form covalent bonds with other disulfide groups when appended to polymers such as PVA, as well as boronic acids, which can form covalent bonds with PVA hydroxyl groups.

As used herein, the term "disulfide" refers to any moiety having a sulfur-sulfur covalent bond.

As used herein, the term "porphyrin" refers to a heterocyclic macrocycle having four pyrrole subunits linked on opposite sides through four methine bridges. Porphyrins readily combine with metals coordinating them in the central cavity. Examples of porphyrins include, but are not limited to, pyropheophorbide-a, pheophorbide, chlorin e6, purpurin, and purpurinimide.

As used herein, the term "linking moiety" refers to a moiety that links a PVA monomer to a functional group such as a disulfide, a porphyrin, an imaging moiety, or a cellular targeting moiety. Linking moieties can be bound to PVA monomers, for example, via ether, ester, or boronate ester linkages formed from PVA hydroxyl groups. Other types of bonds useful for connecting linking moieties to functional groups and PVAs include, but are not limited to, amides, amines, esters, carbamates, ureas, thioethers, thiocarbamates, thiocarbonates and thioureas.

As used herein, the terms "drug" and "therapeutic agent" refer to an agent capable of treating and/or ameliorating a condition or disease. Drugs useful in the present invention include, but are not limited to, paclitaxel, doxorubicin, etoposide, irinotecan, SN-38, cyclosporin A, podophyllotoxin, Carmustine, Amphotericin, Ixabepilone, Patupilone (epothelone class), rapamycin and platinum drugs. The drugs of the present invention also include prodrug forms. One of skill in the art will appreciate that other drugs are useful in the present invention.

As used herein, the term "therapeutic moiety" refers to the portion of a PVA-bound drug that is not covalently linked to a PVA. If a boronic acid-containing drug such as bortezomib is covalently linked to PVA via a boronate ester linkage, for example, the "therapeutic moiety" refers to the radical connected to the bortezomib —B(OH)$_2$ group as shown below:

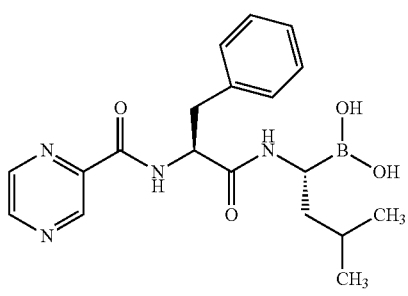

Bortezomib

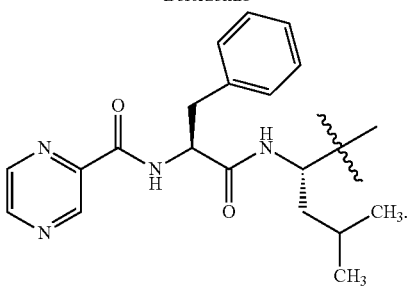

Bortezomib
therapeutic moiety

Use of the term "therapeutic moiety" when referring to a PVA-bound drug is not intended to mean that any particular therapeutic moiety will have therapeutic activity absent the other portions of the PVA-bound drug.

As used herein, the term "cellular targeting moiety" refers to a compound or functional group that will selectively localize to a particular tumor, tissue, organ, or other region of the body. The localization can be mediated by specific recognition of molecular determinants, the molecular size or weight of the targeting agent or conjugate, ionic interactions, hydrophobic interactions, and the like. Other mechanisms of targeting an agent to a particular tissue or region are known to those of skill in the art. For example, certain cellular targeting moieties are capable of binding to a target macromolecule, such as, cell-surface receptors of normal cells, cancer cells and endothelial cells, as well as components in the extracellular matrix and the bony matrix, and surface receptors of infectious agents (virus, fungus, bacteria and parasite, among others). Exemplary targeting agents include, but are not limited to, small organic molecules, peptides, peptidomimetics, peptoids, proteins, polypeptides, glycoproteins, oligosaccharides, nucleic acids, transferrin, HS-glycoprotein, coagulation factors, serum proteins, β-glycoprotein, G-CSF, GM-CSF, M-CSF, EPO, D-phe(1)-tyr(3)-octreotide, and the like. In certain instances, the targeting agent comprises a compound such as a peptidomimetic that cannot be photolytically, chemically, thermally, and/or enzymatically cleaved, e.g., by a protease. Certain targeting moieties include a peptide or peptidomimetic ligand specific for an integrin receptor expressed by a particular cell, tumor, tissue, or organ. As a non-limiting example, peptidomimetic ligands specific for $\alpha_4\beta_1$ integrin (e.g., Ligand 2A, also known as LLP2A) are suitable for use as targeting agents in the antibody conjugates of the present invention.

As used herein, the term "imaging moiety" refers to chemicals that allow body organs, tissue or systems to be imaged. Exemplary imaging agents include paramagnetic agents, optical probes, and radionuclides.

As used herein, the term "randomly distributed" refers to monomer subunits that are arranged in a polymer chain without a repeating order. Any number of monomers having the same structure can reside next to each other in a randomly distributed polymer, or monomers having different structures can reside next to each other in the randomly distributed polymer. In general, however, the arrangement of the monomers does not repeat over the entire length of the polymer chain. As a non-limiting example, one random distribution of monomers A, B, and C in a randomly distributed polymer can be represented visually as: A-B-C-C-C-A-A-B-C-B-A-C-C-B-A-B-A-B-B-B-B-B-B-A-B-B-B-C-A-A-B-C-A-A-C-A, etc.

As used herein, the term "proteasome inhibitor" refers to any substance which inhibits enzymatic activity of the 20S or 26S proteasome in vitro or in vivo. Proteasome inhibitors, their pharmacological properties and use in treating disease, including oncological diseases and inflammatory diseases are reviewed in Ruggeri et al. (2009) *Adv. Pharmacol* 57:91-135. Proteasome inhibitors include, but are not limited to, peptidyl boronic acids.

As used herein, the term "serine protease inhibitor" refers to any substance which inhibits enzymatic activity of a serine protease. A serine protease is an enzyme that catalyzes the hydrolysis of peptide bonds and that is capable of degrading proteins into smaller peptides. Serine proteases are distinguished by the presence of a serine residue in the enzyme reactive side that plays a role in catalysis. Examples of serine proteases include, but are not limited to, chymotrypsin A, subtilisin, and nucleoporin 145.

As used herein, the term "β-lactamase inhibitor" refers to any compound which inhibits enzymatic activity of one or more β-lactamase enzymes. A β-lactamase is an enzyme or protein or any oilier substance that breaks down a β-lactam ring. β-lactamases include enzymes that are produced by bacteria and have the ability to hydrolyze the beta-lactam ring in a beta-lactam antibiotic, either partially or completely.

As used herein, the term "arginase inhibitor" refers to any compound which inhibits enzymatic activity of an arginase. Arginases are enzymes that mediate conversion of L-arginine into ornithine and urea and include, but are not limited to arginase type I and arginase type II.

As used herein, the term "encapsulated" refers to a drug or other compound that is physically adsorbed to, or entrapped in, a nanoparticle of the invention.

As used herein, the term "forming a mixture" refers to the process of bringing into contact at least two distinct species such that they mix together and can react, either modifying one of the initial reactants or forming a third, distinct, species, a product. It should be appreciated, however, the resulting reaction product can be produced directly from a reaction between the added reagents or from an intermediate from one or more of the added reagents which can be produced in the reaction mixture.

As used herein, the term "reducing agent" refers to a compound that can reduce disulfide bonds. Reducing agents include, but are not limited to sodium dithionite, phosphines such as tris(2-carboxyethyl)phosphine, and thiols such as cysteine, cystamine, and β-mercaptoethanol.

As used herein, the term "metal" refers to an element of Groups 2 through 13, inclusive, plus selected elements in Groups 14 and 15 of the periodic table. Metals useful in the present invention include, but are not limited to: Group 2 or IIA elements including beryllium (Be), barium (Ba), and radium (Ra); transition metals (i.e., group IIIB, IVB, VB, VIB, VIIB, VIII, IB, and IIB elements), including scandium (Sc), yttrium (Y), titanium (Ti), rhenium (Re), iron (Fe), cobalt (Co), nickel (Ni), palladium (Pd), platinum (Pt), copper (Cu), silver (Ag), gold (Au), zinc (Zn); Group 13 or IIIA elements including gallium (Ga); and lanthanides including indium (In), thallium (Tl), lanthanum (La), gadolinium (Gd), and lutetium (Lu). Metals of any suitable isotope, ionic state, and/or oxidation state can be used.

As used herein, the term "chelated" refers to a metal ion that is ionically or covalently linked to one or more functional groups of a PVA polymer.

As used herein, the term "fluorophore" refers to a chemical compound, which when excited by exposure to a particular wavelength of light, emits light at a different wavelength. Fluorophores are often described in terms of their emission profile, or "color." Green fluorophores (for example Cy3, FITC, and Oregon Green) can be characterized by their emission at wavelengths generally in the range of 515-540 nanometers. Red fluorophores (for example Texas Red, Cy5, and tetramethylrhodamine) can be characterized by their emission at wavelengths generally in the range of 590-690 nanometers.

As used herein, the term "branched polymer" refers to a polymer having a first polymer chain and one or more polymer side chains extending from the first polymer chain.

As used herein, the term "administering" refers to oral, topical, parenteral, intravenous, intraperitoneal, intramuscular, intralesional, intranasal, subcutaneous, or intrathecal administration to a subject, as well administration as a suppository or the implantation of a slow-release device, e.g., a mini-osmotic pump, in the subject.

As used herein, the terms "treatment" and "treating" refer to full or partial treatment or amelioration of an injury, pathology, condition, or symptom e.g., pain including any objective or subjective parameter such as abatement; remission; diminishing of symptoms or making the symptom, injury, pathology or condition more tolerable to the patient; decreasing the frequency or duration of the symptom or condition; or, in some situations, preventing the onset of symptoms. The treatment or amelioration of symptoms can be based on any objective or subjective parameter; including, e.g., the result of a physical examination.

As used herein, the teen "therapeutically effective amount" refers to a dose of a drug or other agent that produces therapeutic effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins). In sensitized cells, the therapeutically effective dose can often be lower than the conventional therapeutically effective dose for non-sensitized cells.

As used herein, the term "subject" refers to animals such as mammals, including, but not limited to, primates (e.g., humans), cows, sheep, goats, horses, dogs, cats, rabbits, rats, mice and the like. In certain embodiments, the subject is a human.

As used herein, the term "cancer" refers to any member of a class of diseases or disorders characterized by uncontrolled division of cells and the ability of these cells to invade other tissues, either by direct growth into adjacent tissue through invasion or by implantation into distant sites by metastasis. Metastasis is defined as the stage in which cancer cells are transported through the bloodstream or lymphatic system. Cancers include, but are not limited to, carcinomas, lymphomas, leukemias, sarcomas, mesotheliomas, gliomas, germinomas, and choriocarcinomas.

As used herein, the term "tumor" refers to a solid lesion resulting from abnormal growth of cells in a subject. Tumors can be benign or malignant, and can be formed from cancer cells.

As used herein, the term "viral infection" refers to any stage of a viral infection, including incubation phase, latent or dormant phase, acute phase, and development and maintenance of immunity towards a virus. Examples of viruses include, but are not limited to, hepatitis type B or type C, influenza, varicella, adenovirus, herpes simplex virus type I or type II, rinderpest, rhinovirus, echovirus, rotavirus, respiratory syncytial virus, papilloma virus, papova virus, cytomegalovirus, echinovicus, arbovirus, hantavirus, coxsachie virus, mumps virus, measles virus, rubella virus, polio virus, and human immunodeficiency virus type I or type II.

As used herein, the term "bacterial infection" refers to an infection caused by one or more bacterial species such as staphylococci, streptococci, enterococci, *Nesseria* species, *Clostridium* species, *Bordetella* species, *Bacillus* species, or *Corynebacterium* species.

As used herein, the term "photodynamic therapy" refers to the use of nontoxic, light-sensitive compounds that become toxic to malignant or diseased cells upon exposure to light. Photodynamic therapy involves a photosensitizer, a light source, and oxygen. Upon exposure to the light, the photosensitizer generates reactive oxygen species (singlet oxygen, an oxygen free radical) that react with and destroy the malignant tissue. A variety of photosensitizers can be used, including porphyrins, chlorophylls and dyes.

As used herein, the term "photothermal therapy" refers to use of nontoxic, light-sensitive compounds that generate heat upon exposure to light. Like photodynamic therapy, photothermal therapy involves a photosensitizer and a source of light, typically infrared. But photothermal therapy does not require oxygen. A variety of photosensitizers can be used, including porphyrins, chlorophylls and dyes.

As used herein, the term "radiation" refers to the propagation of energy as waves. Examples of radiation include, but are not limited to, visible light, infrared radiation, and microwave radiation.

As used herein, the term "detecting" refers to observing the presence of a chemical, compound, substance, or other species in a given environment. Detecting can include detecting a chemical or physical property of the species in vivo.

As used herein, the term "fluorescence spectroscopy" refers to a type of electromagnetic spectroscopy which analyzes fluorescence from a sample. It typically involves using a beam of light, such as ultraviolet light, to excite the electrons in molecules of certain compounds and causes them to emit light of a lower energy, such as visible light. The emitted light is detected using instruments that are known in the art. As used herein, the term "fluorescence imaging" refers to recording an image of a sample such as a tissue sample by detecting emitted light from fluorescent molecules in the sample to obtain a two-dimensional or three-dimensional image of the sample.

As used herein, the terms "magnetic resonance imaging" and "MRI" refer to conventional MRI methods, as well as improved magnetic resonance (MR) techniques, such as cell-specific imaging, magnetization transfer imaging (MTI), gadolinium (Gd)-enhanced. MRI, proton magnetic resonance spectroscopy (MRS), diffusion-weighted imaging (DWI), functional MR imaging (fMRI), and the other neuro-imaging methods known in the art. MRI methods and their applications to MS are described, for example, in Rovaris et al. *J. Neurol. Sci.* 186 Suppl 1.S3-9 (2001).

As used herein, the terms "positron emission tomography" and "PET" refer to the generation of an image of a sample by detecting gamma rays resulting from the annihilation of positrons emitted by a radiotracer in the sample. Various aspects of PET are described, for example by Bailey, et al. (2005. *Positron Emission Tomography: Basic Sciences*, Secaucus, N.J.: Springer-Verlag).

III. PVA NANOPARTICLES

The present invention provides a nanoparticle including at least one poly(vinyl alcohol) (PVA) having a molecular weight of from about 10 kDa to about 200 kDa, substituted with one or more moieties selected from: a therapeutic agent having a boronic acid moiety, wherein the therapeutic agent is covalently linked to the PVA via a boronate ester bond; a crosslinking group having a disulfide moiety, wherein the crosslinking group is covalently linked to the PVA, and a porphyrin, wherein the porphyrin is covalently linked to the PVA.

The nanoparticles of the present invention include one or more PVAs having a molecular weight of from about 10 kDa to about 200 kDa. The PVA can have any suitable molecular weight such as, for example, from about 15 kDa to about 175 kDa, from about 24 kDa to about 160 kDa, or from about 28 kDa to about 96 kDa, or from about 32 kDa to about 60 kDa. The PVA can have a molecular weight of from about 10 kDa to about 100 kDa, or from about 100 kDa, to about 200 kDa. The molecular weight can be about 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 kDa. One of skill in the art will appreciate that a certain degree of polydispersity is exhibited by any sample of a polymeric material. That is, the sample will include polymers having a distribution of molecular weights around the average molecular weight of the polymers in the sample.

Any molecular weight set forth herein can be a number average molecular weight or a weight average molecular weight. The number average molecular weight ($M_n$) of a polymer sample refers to the statistical average molecular weight of all of the polymer chains in the sample, defined by Equation 1:

$$M_n = \frac{\Sigma N_i M_i}{\Sigma N_i} \quad (1)$$

In Equation 1, $M_i$ is the molecular weight of a polymer chain and $N_i$ is the number of polymer chains that has that molecular weight. The weight average molecular weight ($M_w$) of a polymer sample takes into account the fact that the molecular weight of a particular polymer will affect that polymer chain's contribution to the average molecule weight. The weight average molecular weight is defined by Equation 2:

$$M_w = \frac{\Sigma N_i M_i^2}{\Sigma N_i M_i} \quad (2)$$

Unless otherwise specified, the molecular weight values referred to herein are weight average molecular weights.

Both weight average molecular weight and number average molecular weight can be determined using known techniques (e.g., gel permeation chromatography analysis, intrinsic viscosity measurement, and the like). The polydispersity index (PDI) relates to the breadth of the molecular weight distribution of a given polymer sample and can be expressed as the ratio of the weight average molecular weight to the number average molecular weight as shown in Equation 3.

$$PDI = \frac{M_w}{M_n} \quad (3)$$

Methods for the synthesis of monodisperse PVA (or nearly monodisperse polymers) are known, and monodisperse PVA can be used in the nanoparticles of the present invention. The nanoparticles of the invention can include any suitable number of PVA polymer chains. The nanoparticles of the present invention include at least one PVA polymer chain and can include 2, 3, 4, 5, 6, 7, 8, 9, or 10 PVA polymer chains. The nanoparticles of the present invention can include 10 or more, or 20 or more, or 30 or more, or 40 or more, or 50 or more PVA polymer chains.

The nanoparticles of the present invention can be of any suitable size. In general, the nanoparticles have diameters ranging from about 1 nm to about 1000 nm. The diameter of the nanoparticles can be, for example, from about 1 nm to about 25 nm, from about 25 nm to about 50 nm, from about 50 nm to about 100 nm, from about 250 nm to about 500 nm, from about 500 nm to about 750 nm, from about 750 nm to about 1000 nm, from about 1 to about 10 nm, from about 10 to about 100 nm, from about 25 nm to about 250 nm, or from about 50 nm to about 500 nm. In some embodiments, the diameter of the nanoparticles is less than about 500 nm. In some embodiments, the diameter is less than about 250 nm. In some embodiments, the diameter is less that about 100 nm. In some embodiments, the diameter of the nanoparticle is about 5 nm. In some embodiments, the diameter of the nanoparticle is about 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95 or 100 nm. One of skill in the art will appreciate that the size of the nanoparticle will depend on factors such as the size and number of PVA chains in the particle; the extent of PVA functionalization with moieties such as boronic-acids, porphyrins, and lipoic acid; as well as the extent of loading with drugs, imaging agents, and the like. The nanoparticles are generally formed by the self-assembly of PVA-based polymer conjugates in aqueous solutions by dialysis.

A. Boronic Acid PVA Nanoparticles

In some embodiments, the PVA includes the therapeutic agent having the boronic acid moiety as described above.

In some embodiments, the PVA has a structure according to formula I:

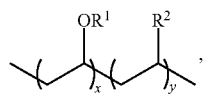

(I)

wherein:

each $R^1$ is independently selected from H and a moiety according to formula Ia:

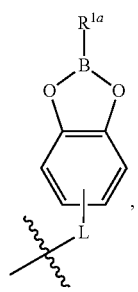

(Ia)

wherein L is a linking moiety and $R^{1a}$ is a therapeutic moiety, or any two adjacent $R^1$ moieties are taken together with the oxygen atoms to which are bound to form a moiety according to Formula Ib:

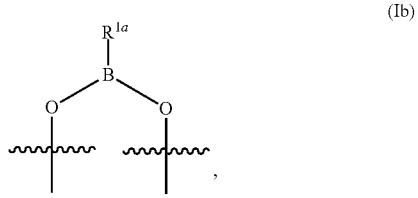

(Ib)

wherein $R^{1a}$ is a therapeutic moiety,
provided that at least one $R^1$ is H and at least one $R^1$ is other than H;
each $R^2$ is independently selected from —OH, a cellular targeting moiety, and an imaging moiety, or any two adjacent $R^2$ moieties are taken together to form a cellular targeting moiety or an imaging moiety;
subscript x is an integer of from about 1 to about 1200, and
subscript y is an integer of from 0 to about 3800, wherein the sum of x and y is an integer of from about 200 to about 5000, and the x and y repeating units are randomly distributed in the PVA.

In some embodiments, each $R^2$ is independently selected from a cellular targeting moiety and an imaging moiety, or any two adjacent $R^2$ moieties are taken together to form a cellular targeting moiety or an imaging moiety. In some embodiments, subscript y is an integer of from about 199 to about 3800.

A number of useful boronic acid-containing compounds can be bound to the PVA nanoparticles of the present invention. Boronic acids that inhibit proteasomes, serine proteases, aspartic proteases, metalloproteases, γ-glutamyl transpeptidase inhibitors, thioesterases, cysteine proteases, tyrosine kinases, β-lactamases, and arginases are known in the art and can be used with the nanoparticles of the invention. Examples of such compounds include phenylboronic acids; borodipeptides such as N-(2,3-dihydro-1,4-benzodioxin-2-ylcarbonyl)-L-phenylalanyl-(R)-boropheneyl-alanine and [(1R)-3-methyl-1-({(2S)-3-phenyl-2-[(pyrazin-2-ylcarbonyl)amino]propanoyl}amino)butyl] boronic acid (bortezomib); and boronic chalcones such as 3,5-bis-(4-boronic acidbenzylidene)-1-methyl-piperidin-4-one. Further examples of useful boronic acid-containing compounds include those described in U.S. Pat. Nos. 4,499,082; 5,106,948; 5,169,841; 5,187,157; 5,242,904; 5,250,720; 5,574,017; 5,780,454; 6,066,730; 6,083,903; 6,169,076; 6,297,217; 6,933,290; 6,699,835; 7,223,745; 7,317,109; 7,576,206; 7,674,913; 7,829,742; 7,998,997; 8,378,099; and 8,664,200; which patents are incorporated by reference herein in their entirety.

The nanoparticles of the present invention can be loaded with boronic acid-containing compounds via formation of boronate ester bonds with PVA hydroxyl groups shown below in Scheme 1.

Scheme 1

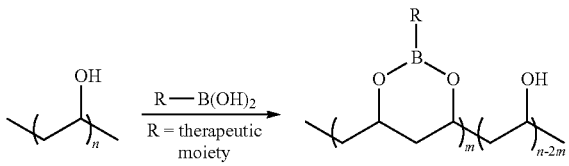

The PVA can be modified with additional functional groups, such as targeting moieties or imaging moieties, as shown in Scheme 2. PVA hydroxyl groups can be converted to azides and subsequently reacted with functionalized alkynes via 1,3-dipolar cycloaddition to install the additional functional groups. Loading with a boronic acid-containing compound can be conducted before or after modification via the cycloaddition reaction.

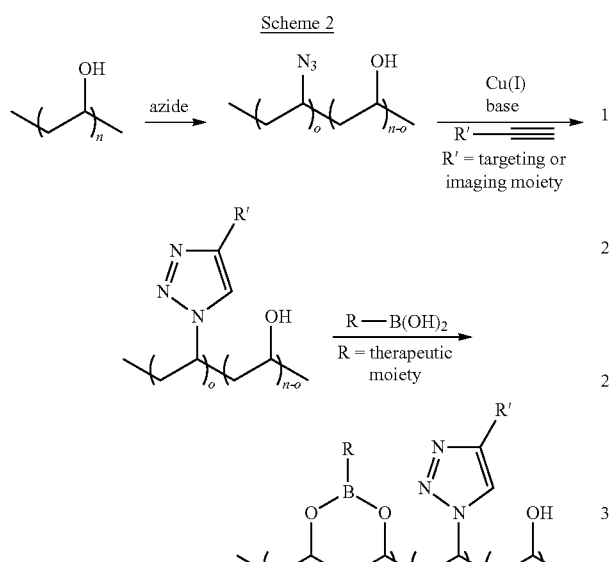

The nanoparticles of the invention can also be loaded with boronic acid-containing compounds by modifying the PVA with catechol moieties as shown in Scheme 3. The hydroxyl groups of the catechol moieties are used to form boronate ester bonds with the boronic acid-containing compound. Modification of the PVA with functional groups, such as targeting moieties or imaging moieties, via the azide-alkyne cycloaddition chemistry described above can be conducted before or after modification of the PVA with catechol moieties.

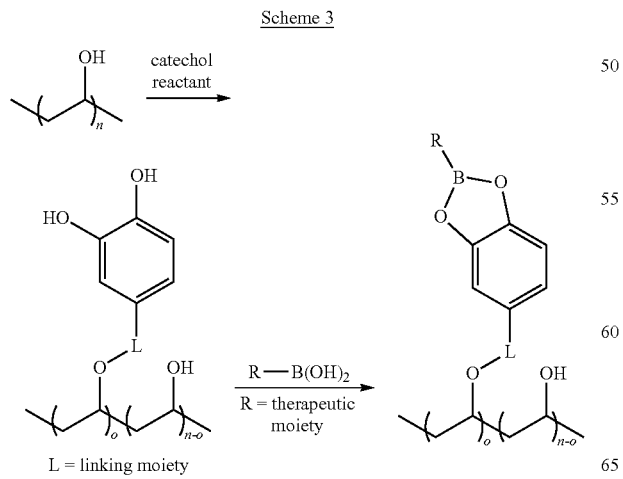

In some embodiments, the therapeutic agent is selected from the group consisting of a proteasome inhibitor, a serine protease inhibitor, a β-lactamase inhibitor, and an arginase inhibitor.

In some embodiments, each $R^{1a}$ is independently selected from the group consisting of:

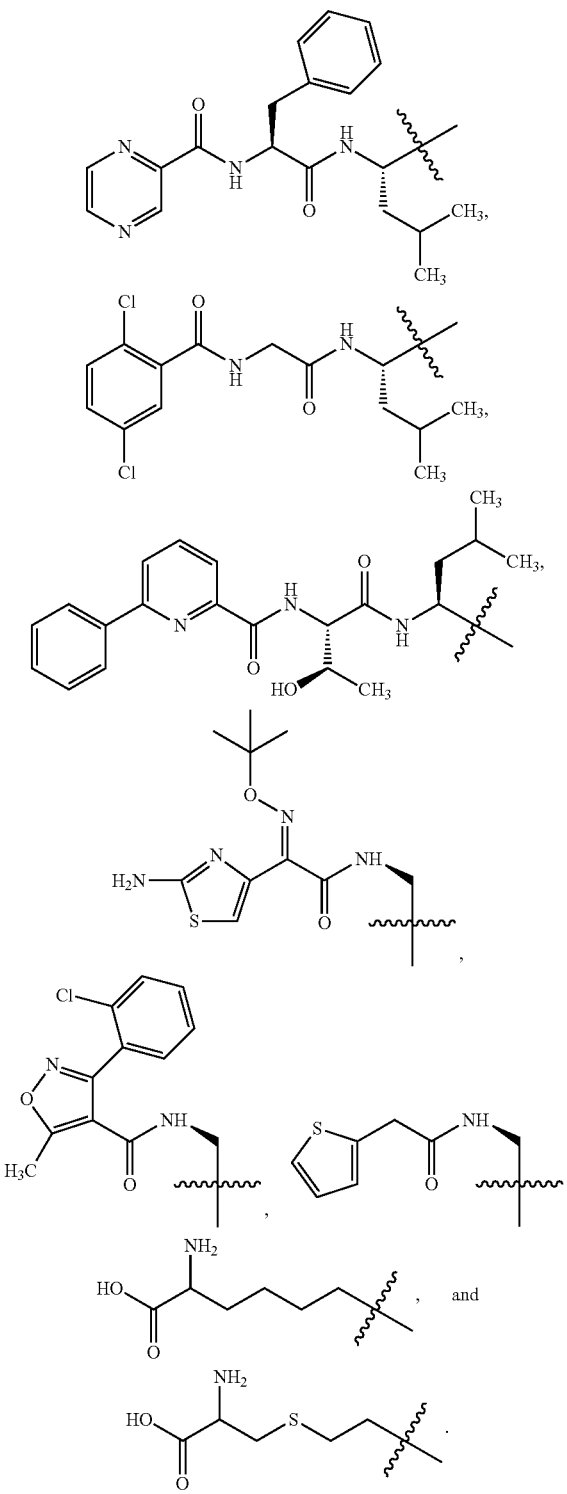

In some embodiments, $R^{1a}$ is:

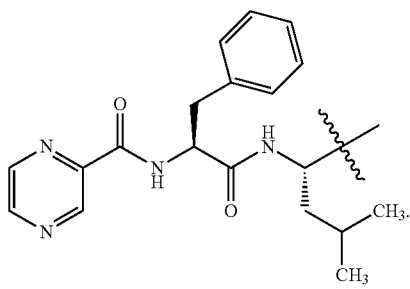 [SMILES: *[C@H](CC(C)C)NC(=O)[C@H](Cc1ccccc1)NC(=O)c1cnccn1]

The nanoparticles of the invention can include any suitable number of boronic acid-containing therapeutic agents. In general, up to about 25% of PVA monomers can be bound to a boronic acid containing drug. For example, from about 1% to about 25% of the PVA monomers can be bound to a boronic acid containing drug, or from about 5% to about 15% of the PVA monomers can be bound to a boronic acid containing drug. In some embodiments, about 1, 5, 10, 15, 20, or 25% of the PVA monomers can be bound to a boronic acid containing drug. The loading level of the particles will depend in part on factors such as the molecular weight of the PVA as well as the identity of the particular boronic acid containing drug.

In some embodiments, the nanocarrier includes at least one monomer unit that is optionally linked to an optical probe, a radionuclide, a paramagnetic agent, a metal chelate or a drug. The drug can be a variety of hydrophilic or hydrophobic drugs. Drugs that can be sequestered in the nanocarriers or linked to the conjugates of the present invention include, but are not limited to, cytostatic agents, cytotoxic agents (such as for example, but not limited to, DNA interactive agents (such as cisplatin or doxorubicin)); taxanes (e.g., taxotere, taxol); topoisomerase II inhibitors (such as etoposide); topoisomerase I inhibitors (such as irinotecan (or CPT-11), camptostar, or topotecan); tubulin interacting agents (such as paclitaxel, docetaxel or the epothilones); hormonal agents (such as tamoxifen); thymidilate synthase inhibitors (such as 5-fluorouracil); antimetabolites (such as methotrexate); alkylating agents (such as temozolomide (TEMODAR™ from Schering-Plough Corporation, Kenilworth, N.J.), cyclophosphamide); aromatase combinations; ara-C, adriamycin, cytoxan, and gemcitabine. Other drugs useful in the nanocarrier of the present invention include but are not limited to Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, oxaliplatin (ELOXATIN™ from Sanofi-Synthelabo Pharmaceuticals, France), Pentostatins, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17α-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, Anastrazole, Letrazole, Capecitahine, Reloxatine, Droloxafine, or Hexamethylmelamine. Prodrug forms are also useful in the present invention.

Other drugs useful in the present invention also include radionuclides, such as $^{67}$Cu, $^{90}$Y, $^{123}$I, $^{125}$I, $^{131}$I, $^{177}$Lu, $^{188}$Re, $^{186}$Re, $^{211}$At, and $^{223}$Ra. In some embodiments, a radionuclide can act therapeutically as a drug and as an imaging agent.

In some embodiments, the nanoparticle further includes a drug encapsulated in the nanoparticle. In some embodiments, the drugs are present on the exterior of the particles (e.g., via adsorption).

B. Lipoic Acid PVA Nanoparticles

In some embodiments, the nanoparticle includes a PVA comprising the crosslinking group having the disulfide moiety. In some embodiments, the PVA has a structure according to formula II:

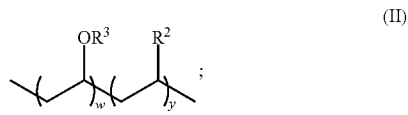

wherein
each $R^3$ is independently selected from H and a moiety -$L^3$-$R^{3a}$, wherein
    $L^3$ is a linking moiety and $R^{3a}$ is the disulfide moiety, provided that at least one $R^3$ is H and at least two $R^3$ are the moiety -$L^3$-$R^{3a}$;
each $R^2$ is independently selected from —OH, a cellular targeting moiety, and an imaging moiety, or any two adjacent $R^2$ moieties are taken together to form a cellular targeting moiety or an imaging moiety;
subscript w is an integer of from about 2 to about 1200, and
subscript y is an integer of from 0 to about 3800, wherein the sum of w and y is an integer of from about 200 to about 5000, and
the w and y repeating units are randomly distributed in the PVA.

In some embodiments, each $R^2$ is independently selected from a cellular targeting moiety and an imaging moiety, or any two adjacent $R^2$ moieties are taken together to form a cellular targeting moiety or an imaging moiety. In some embodiments, y is an integer of from about 198 to about 3800.

Any suitable moiety disulfide moiety and linking moiety can be used in the nanoparticles of the invention. In some embodiments, the two sulfur atoms of the disulfide moiety are adjacent ring atoms in a 4- to 10-membered monocyclic or bicyclic group. In some embodiments, the two atoms of the disulfide moiety are adjacent ring atoms in a 5- to 6-membered ring. In some embodiments, the two atoms of the disulfide moiety are adjacent ring atoms in a 5-membered ring. Alternatively, the disulfide moiety can be an acyclic, mixed disulfide such as a 2-pyridyl disulfide or a 4-thio2-nitrobenzoic acid (TNB) disulfide.

In PVAs according to Formula II, a disulfide moiety $R^{3a}$ is linked to the PVA in the nanoparticle via a linking moiety $L^3$. Any suitable linking moiety can be used in the nanoparticles of the invention. In some embodiments, the linking moiety $L^3$ contains a hydrophobic group such as a branched or straight-chain $C_4$-$C_{18}$ alkylene group. The linking moiety can contain, for example, a straight-chain $C_4$ alkylene group or a straight-chain $C_{10}$ alkylene group.

Disulfide moieties can be installed on the polyvinyl alcohol using a suitable reactive group. For example, PVA hydroxyl groups can be reacted with a disulfide-containing carboxylic acid in the presence of coupling agent, such as a carbodiimide (e.g., dicychohexylcarbodiimide or 1-ethyl-3-(3-dimethyaminopropyl)carbodiimide), a phosphonium reagent (BOP), or an aminium reagent, to install the disulfide moieties via ester formation. Alternatively, PVA hydroxyl groups can be reacted with a carbonylating reagent such as carbonyldiimidazole followed by a disulfide-containing amine to install the disulfide moieties via carbamate formation. Other reactions for modification of alcohols can be used to install the disulfide moieties on the PVA in the nanoparticles of the invention. Such reactions are described, for example, by March and Smith (2007. *Advanced Organic Chemistry: Reactions, Mechanisms, and Structure*. John Wiley & Sons).

In some embodiments, the disulfide moieties are installed on the PVA by reaction of PVA hydroxyl groups with lipoic acid using dicyclohexylcarbodiimide (DCC) or 1-ethyl-3-(3-dimethylaminopropyl)carbodiimide (EDC). In some embodiments, the disulfide moieties are installed on the PVA by reaction of PVA hydroxyl groups with a mixed disulfide (such as a 2-pyridyl disulfide) of 6-mercaptohexanoic acid or 11-mercaptoundecanoic acid.

In some embodiments, the PVA has a structure according to formula II as described above wherein the moiety -$L^3$-$R^{3a}$ has a structure according to formula IIa:

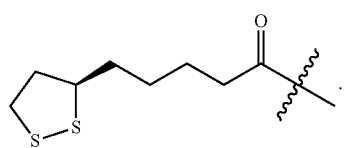

(IIa)

In some embodiments, the nanoparticle further includes a drug encapsulated in the nanoparticle.

In related embodiments, the invention provides a method for preparing a nanoparticle having a crosslinking group with a disulfide moiety and further having a drug encapsulated in the nanoparticle. The method includes forming a mixture comprising the nanoparticle and a drug and adding a reducing agent to the mixture under conditions sufficient to form disulfide bonds between at least two sulfur-containing polymer sidechains, thereby encapsulating the drug in the particle.

Any suitable reducing agent can be used in the methods of the invention. Suitable reducing agents include, but are not limited to, thiols such as cysteine, N-acetylcysteine, cysteamine, β-mercaptoethanol, 2-mercaptoethanesulfonic acid sodium salt, dithiothreitol (DTT), dithioerythritol (DTE), bis(2-mercaptoethyl)sulfone, (2S)-2-amino-1,4-dimercaptobutane (as described in U.S. Patent Appl. Pub. No. 2013/02110555), and the like. Any suitable amount of reducing agent can be used in the methods of the invention. In general, the molar ratio of the reducing agent to the disulfide moiety ranges from about 0.01:1 to about 10.1:1. In some embodiments, the molar ratio of DTT to lipoyl moieties in the PVA is about 0.1:1.

C. Porphyrin PVA Nanoparticles

In some embodiments, the PVA comprises the porphyrin. In some embodiments, the PVA has a structure according to formula III:

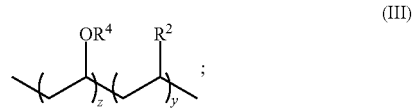

(III)

wherein
each $R^4$ is independently selected from H and a moiety -$L^4$-$R^{4a}$, wherein $L^4$ is a linking moiety and $R^{4a}$ is the porphyrin,
  provided that at least one $R^4$ is H and at least one $R^4$ is the moiety -$L^4$-$R^{4a}$;
each $R^2$ is independently selected from OH, a cellular targeting moiety, and an imaging moiety, or any two adjacent $R^2$ moieties are taken together to form a cellular targeting moiety or an imaging moiety;
subscript z is an integer of from about 1 to about 1200, and
subscript y is an integer of from 0 to about 3800, wherein the sum of z and y is an integer of from about 200 to about 5000, and
  the z and y repeating units are randomly distributed in the PVA.

In some embodiments, each $R^2$ is independently selected from a cellular targeting moiety and an imaging moiety, or any two adjacent $R^2$ moieties are taken together to form a cellular targeting moiety or an imaging moiety. In some embodiments, y is an integer of from about 199 to about 3800.

Any suitable porphyrin can be used in the nanoparticles of the present invention. Representative porphyrins suitable in the present invention include, but are not limited to, pym-pheophorbide-a, pheophorbide, chlorin e6, purpurin or purpurinimide. Representative structures are shown below:

| PORPHYRIN | STRUCTURE |
|---|---|
| Porphyrin | 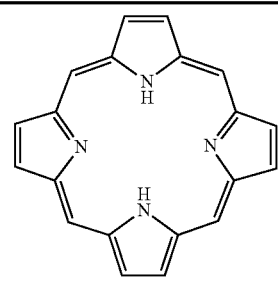 |
| Pyro-pheophorbide-a | 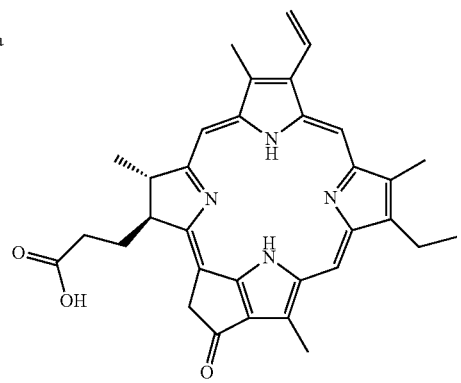 |

| PORPHYRIN | STRUCTURE |
|---|---|
| Pheophorbide | 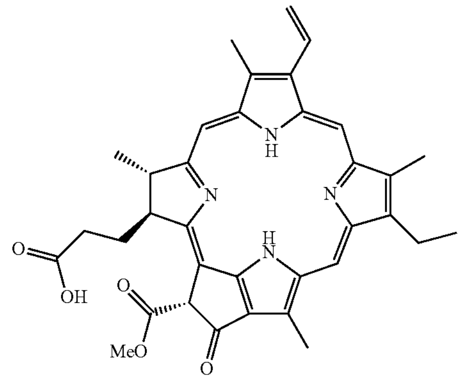 [SMILES: C=Cc1c(C)c2cc3nc(c4c5[nH]c(cc6nc(cc1[nH]2)C(C)=C6CC)c(C)c5C(=O)[C@@H]4C(=O)OC)[C@@H](CCC(=O)O)[C@@H]3C] |
| Chlorin e6 | 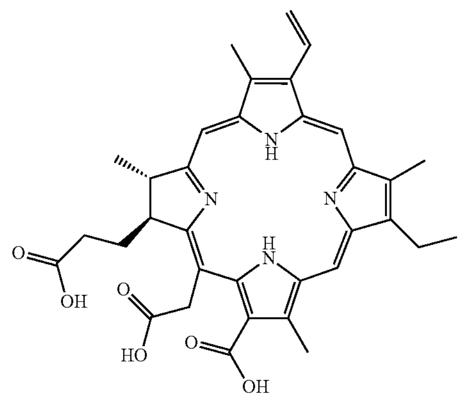 [SMILES: C=Cc1c(C)c2cc3nc(c(CC(=O)O)c4[nH]c(cc5nc(cc1[nH]2)C(C)=C5CC)c(C)c4C(=O)O)[C@@H](CCC(=O)O)[C@@H]3C] |
| Purpurin | 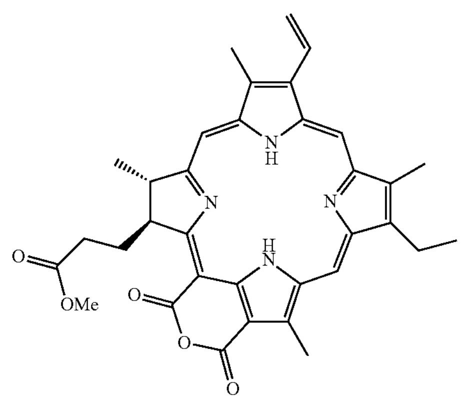 [SMILES: C=Cc1c(C)c2cc3nc(c4c5[nH]c(cc6nc(cc1[nH]2)C(C)=C6CC)c(C)c5C(=O)OC4=O)[C@@H](CCC(=O)OC)[C@@H]3C] |
| Purpurinimide | 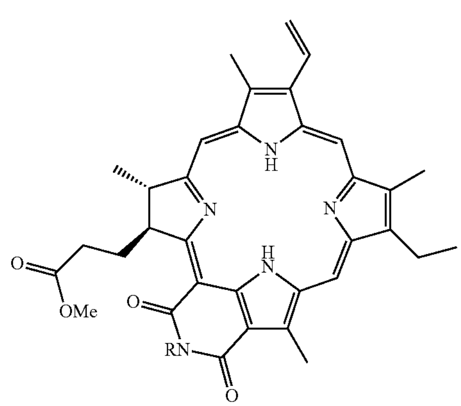 |

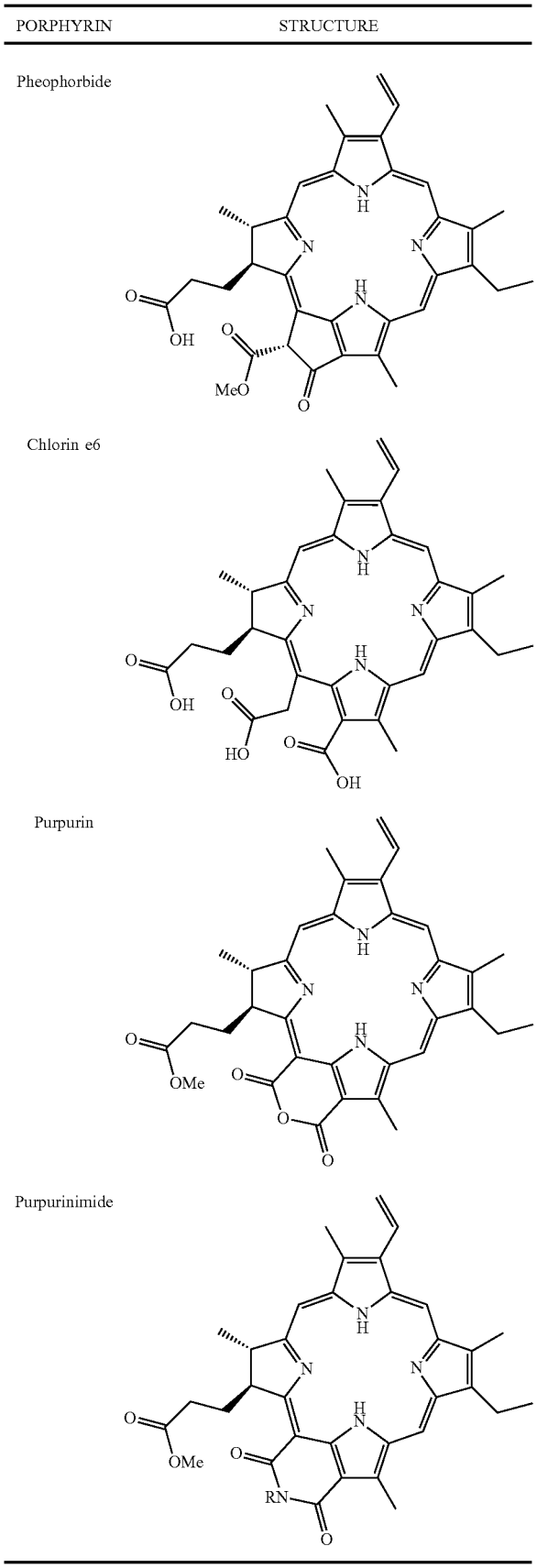

In some embodiments, each $R^{4a}$ is independently selected from pyropheophorbide-a, pheophorbide, chlorin e6, purpurin, and purpurinimide. In some embodiments, the porphyrin is pyropheophorbide-a.

In some embodiments, the moiety -$L^4$-$R^{4a}$ has a structure according to formula (IIIa)

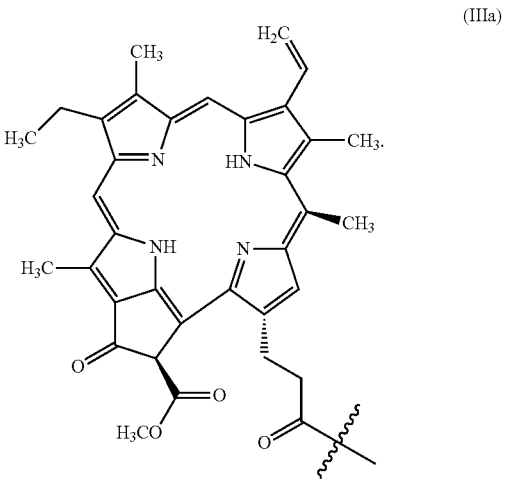

In some embodiments, the nanoparticle further includes a metal chelated to the porphyrin moiety, wherein the metal is selected from the group consisting of Fe, Zn, Pd, Pt, Gd, $^{63}$Cu, $^{65}$Cu, $^{64}$Cu, $^{67}$Cu, $^{177}$Lu, $^{67}$Ga, $^{111}$In, $^{90}$Yt, and $^{223}$Ra.

In some embodiments, the nanoparticle further comprises a drug encapsulated in the particle.

IV. PVA NANOPARTICLES WITH TARGETING MOIETIES AND IMAGING MOIETIES

The nanoparticles of the present invention can optionally include one more additional functional groups including targeting moieties, imaging moieties, or both targeting and imaging moieties. In some embodiments, the nanoparticles include a PVA according to formula I, formula II, or formula III as described above:

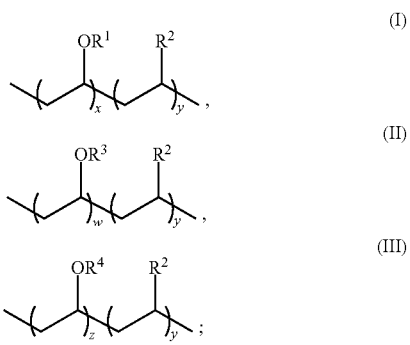

wherein the subscript y is 0. In such embodiments, the PVA does not include targeting or imaging moieties.

In some embodiments, the nanoparticles include a PVA according to formula I, formula II, or formula III as described above:

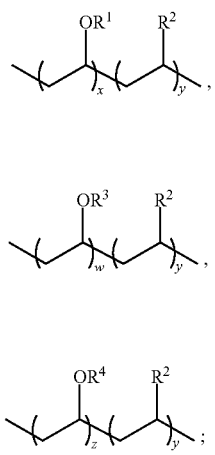

wherein the subscript y is an integer of from 1 to about 400.

Targeting moieties and imaging moieties can be installed on the PVA using a number of synthetic routes. Targeting or imaging moieties can be installed on the polyvinyl alcohol using a suitable reactive group. For example, PVA hydroxyl groups can be reacted with a carboxylic acid having a targeting or imaging moiety in the presence of coupling agent, such as a carbodiimide (e.g., dicychohexylcarbodiimide or 1-ethyl-3-(3-dimethyaminopropyl)-carbodiimide), a phosphonium reagent (BOP), or an aminium reagent, to install the targeting or imaging moieties via ester formation. Alternatively, PVA hydroxyl groups can be reacted with a carbonylating reagent such as carbonyldiimidazole followed by a functionalized amine to install the targeting or imaging moieties via carbamate formation.

In some embodiments, targeting moieties or imaging moieties can be installed using azide-alkyne cycloaddition as described above and shown in Scheme 2. In some embodiments, a targeting or imaging moiety can be conjugated to an arylboronic acid and be installed on the PVA via subsequent boronate ester formation. Other reactions for modification of alcohols as described, for example, by March (supra) can be used to install the targeting or imaging moieties on the PVA in the nanoparticles of the invention.

Accordingly, some embodiments of the invention provide nanoparticles of Formula I, formula II, or Formula III as described above, wherein the subscript y is an integer of from 1 to about 400 and wherein each $R^2$ is a moiety according to formula IVa

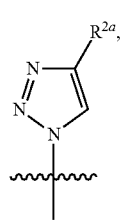

or any two adjacent $R^2$ moieties are taken together to form a moiety according to formula IVb

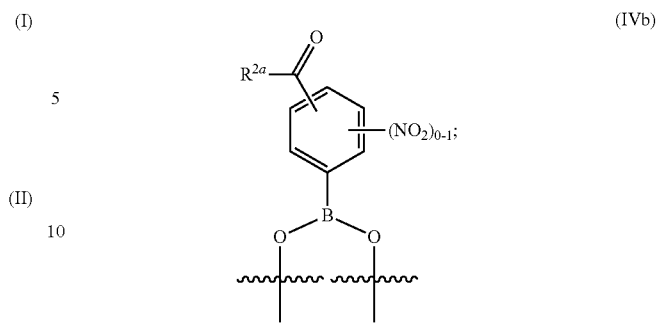

wherein each is independently selected from a cellular targeting moiety and an imaging moiety.

In some embodiments, each $R^2$ is the moiety according to formula IVa.

In some cases, the nanoparticles of the invention can accumulate at a target site in a subject due to the enhanced permeability and retention characteristics of certain tissues such as cancer tissues. Accumulation in such a manner often results in part because of nanoparticle size and may not require special targeting functionality. In other cases, the targeting moieties can be used to direct the nanoparticles to the desired site within the subject. Generally, the targeting moieties of the present invention can associate with any target of interest, such as a target associated with an organ, tissues, cell, extracellular matrix, or intracellular region. In certain embodiments, a target can be associated with a particular disease state, such as a cancerous condition. In some embodiments, a targeting moiety can be specific to only one target, such as a receptor. Suitable targets can include but are not limited to a nucleic acid, such as a DNA, RNA, or modified derivatives thereof. Suitable targets can also include but are not limited to a protein, such as an extracellular protein, a receptor, a cell surface receptor, a tumor-marker, a transmembrane protein, an enzyme, or an antibody. Suitable targets can include a carbohydrate, such as a monosaccharide, disaccharide, or polysaccharide that can be, for example, present on the surface of a cell.

In certain embodiments, a targeting moiety can include target ligand (e.g., an RGD-containing peptide), a small molecule mimic of a target ligand (e.g., a peptide mimetic ligand), or an antibody or antibody fragment specific for a particular target. In some embodiments, a targeting moiety can further include folic acid derivatives, B-12 derivatives, integrin RGD peptides, NOR derivatives, somatostatin derivatives or peptides that bind to the somatostatin receptor, e.g., octreotide and octreotate, and the like. The targeting moieties of the present invention can also include an aptamer. Aptamers can be designed to associate with or bind to a target of interest. Aptamers can be comprised of, for example, DNA, RNA, and/or peptides, and certain aspects of aptamers are well known in the art. (See. e.g., Klussman, S., Ed., The Aptamer Handbook, Wiley-VCH (2006); Nissenbaum, E. T., Trends in Biotech. 26(8): 442-449 (2008)).

In another embodiment, the targeting moiety is selected from the group consisting of an antibody, antibody fragment, small organic molecule, peptide, protein, polypeptide, glycoprotein, oligosaccharide, and the like. In a preferred embodiment, the targeting moiety is an antibody or antibody fragment. Suitable antibodies include, but are not limited to, monoclonal, polyclonal, and recombinant antibodies, as well as antigen binding fragments (Fab) thereof. Preferably, the antibody is a monoclonal antibody. The antibodies of the present invention can be derived from any mammalian species, such as mouse, rat, and rabbit, and are preferably humanized or chimeric, for example, by including human protein sequence in the constant region of the antibody light and heavy chains. In another embodiment, the antibody binds to an antigen on the surface of a cancer or tumor cell. Such antibodies include, but are not limited to, antibodies against the ChL6, Lym-1, CD1b, CD3, CD5, CD 14, CD20, CD22, CD33, CD52, CD56, TAG-72, HER2/neu, interleukin-2 receptor (IL-2R), ferritin, neural cell adhesion molecule (NCAM), melanoma-associated antigen, ganglioside $G_D2$, EGF receptor, and tenascin antigens.

Targeting moieties can also be identified using screening methods such as the one-bead one-compound (OBOC) combinatorial library method, which has been applied to the discovery of tumor cell specific targeting ligands (Lam, K. S., et al. *Nature* 354, 82-84 (1991)). For example, by screening random OBOC peptidomimetic libraries against live Jurkat T-lymphoid leukemia cells, LLP2A, a peptidomimetic ligand against activated $\alpha 4\beta 1$ integrin with an $IC_{50}$ of 2 pM in a cell adhesion assay (Peng, L., et al. *Nat Chem Biol* 2, 381-389 (2006)) was discovered. When conjugated to a near infra-red dye, LLP2A is able to image $\alpha 4\beta 1$-expressing tumor (e.g., T- and B-lymphoma) in a xenograft model in nude mice, with high sensitivity and specificity. Furthermore, through screening the secondary library (cXGXGXXc-Bead) and two highly focused cyclic peptide libraries against $\alpha 3$ integrin expressing breast cancer cell line (MDA-MB-231), a cyclic peptide (LXY3) with high binding specificity ($K_d$=57 nM) to $\alpha 3$ integrin was identified (Yao. N., et al. *J Med Chem* (2008)). The targeting efficiency and specificity of LXY3 to the breast adenocarcinoma tumors in mouse xenografts were confirmed by in vivo and ex vivo near-infrared optical imaging. LXW7 (cGRGDdvc, a cyclized D-amino acid containing peptide) has also been identified as a highly specific targeting ligands for $\alpha v \beta 3$ integrin that is present on endothelial cells of growing blood vessels (Xiao, W., et al. *Mol Cancer Ther* 9, 2714-2723 (2010)).

In the OBOC combinatorial library method, a "split-mix" synthetic strategy is used to generate a combinatorial library and each bead expresses only one chemical entity (Lam et al, supra; Lam et al., *Chem. Rev.*, 97:411-448 (1997)). Random libraries of millions of beads can then be screened in parallel for a specific acceptor molecule (e.g., receptor, antibody, enzyme, virus, whole cell, etc.). Using an enzyme-linked colorimetric assay similar to that used in Western blotting, the OBOC combinatorial library method was successful in identifying ligands for an anti-$\beta$-endorphin antibody (Lam et al., *Bioorg. Med. Chem. Lett.*, 3:419-424 (1993)), streptavidin (Lain et al., *Pept.: Chem., Struct., Biol., Proc. Am. Pept. Symp.* 13th, pp. 1005-1006 (1994)), avidin (Lam and Lebl, *ImmunoMethods*, 1:11-15 (1992)), an anti-insulin monoclonal antibody recognizing a discontinuous epitope (Lam et al., In "Peptides: Chem., Sturct., and Biol." Ed. Hodges, pp. 1003-1004 (1994)), MHC-Class I molecules (Smith et al., *Mol. Immunol.*, 31:1431-1437 (1994)), indigo carmine (a small organic dye) (Lam et al., *Drug Dev. Res.*, 33:157-160 (1994)), and a surface idiotype of B-cell lymphoma cell lines (Lam et al., *Biomed. Pept. Prot., and Nuc. Acids*, 1:205-210 (1995)). The positive beads were then physically isolated for structural determination by microsequencing using automatic Edman degradation (Lam et al., *Nature*, 354:82-84 (1991)).

The OBOC combinatorial library method can also be used for screening radiolabeled peptides. For example, substrate motifs for protein kinases were identified using peptides radiolabeled with [$\gamma$-$^{32}$P]-ATP. (Lam and Wu, *Methods*, 6:401-403 (1994); Wu et al., *Biochem.*, 33:14825-14833 (1994); Lam et al., *Intl. Prot. Pept. Res.*, 45:587-592 (1995); Lou et al., *Bioorg. Med. Chem.*, 4:677-682 (1996)). Using these peptide substrates as templates, potent pseudo-substrate-based peptide inhibitors for p60$^{c-src}$ protein tyrosine kinase were also developed (Alfaro-Lopez et al., *J. Med. Chem.*, 41:2252-2260 (1998)). Since the OBOC combinatorial library method uses a parallel approach, each compound is spatially separated on individual beads, and multiple different peptide motifs can be identified (Wu et al., *J. Comb. Chem. High-throughput screening* (2002)). Recently, OBOC combinatorial peptidomimetic libraries were used to identify peptidomimetic substrates for the development of c-src inhibitors (Kamath et al., In "Peptides: the wave of the future." Proc. of Pept. Symp., Jun. 9-14, 2001).

For example, U.S. Patent Publication No. 20060019900 describes the synthesis and structures of peptidomimetic ligands specific for $\alpha_4\beta_1$ integrin. In particular, using 4-((N'-2-methylphenyl)ureido)-phenylacetyl-LDVP ("BIO-1211") as a template, various OBOC combinatorial peptidomimetic libraries containing both naturally-occurring amino acids, unnatural amino acids, and D-amino acids were designed to elucidate $\alpha_4\beta_1$ integrin ligands with increased affinity, specificity, and stability. In order to remove ligands with low to moderate binding affinity, the screening method was modified by incorporating, BIO-1211 as a competitive ligand in solution. As a result, only those ligands with high affinity were completely covered by a monolayer of live lymphoid cancer cells. Cancer cell-binding affinity was performed on Jurkat T leukemia cells, Molt-4 leukemia cells, and/or fresh cancer cells obtained from acute lymphocytic leukemia patients. By using this method, $\alpha_4\beta_1$ integrin ligands with affinity significantly higher than that of BIO-1211 were identified. Furthermore, the ligands identified by this method contained at least one unnatural $\alpha$-amino acid, D-amino acid, or a combination thereof, a property that confers greater stability to the ligands upon administration. Therefore, these ligands have significantly better pharmacokinetic properties as well as cancer targeting properties compared to BIO-1211.

Ligands specific for additional members of the integrin family or other cell-surface receptors can also be identified using the OBOC combinatorial library method. Examples of additional integrin family members for which ligands can be identified include, without limitation, $\alpha_1\beta_1$, $\alpha_2\beta_1$, $\alpha_3\beta_1$, $\alpha_4\beta_1$, $\alpha_4\beta_7$, $\alpha_5\beta_1$, $\alpha_6\beta_1$, $\alpha_6\beta_4$, $\alpha_7\beta_1$, $\alpha_8\beta_1$, $\alpha_9\beta_1$, $\alpha_D\beta_2$, $\alpha_D\beta_2$, $\alpha_M\beta_2$, $\alpha_v\beta_1$, $\alpha_v\beta_3$, $\alpha_v\beta_5$, $\alpha_v\beta_6$, $\alpha_v\beta_8$, $\alpha_x\beta_2$, $\alpha_{IIb}\beta_3$, and $\alpha_{IELb}\beta_7$. Non-limiting examples of other cell-surface receptors for which ligands can be identified include CD19, CD20, CD22, CD37, CD40, L6, CD2, CD28, CD30, CD40, CD50 (ICAM3), CD54 (ICAM1), CD80, CD86, B7-H1, CD134, (OX40), CD137 (41BB), CD152 (CTLA-4), CD153 (CD30 ligand), CD154 (CD40 ligand), ICOS, CD19, CD3, CD4, CD25, CD8, CD11b, CD14, CD25, CD56CD69, EGFR/HER1/ErbB1, HER2/Neu/ErbB2, HER3/ErbB3, HER4/ErbB4, VEGFR-1/FLT-1, VEGFR-2/FLK-1/KDR, VEGFR-3/FLT-4, FLT-3/FLK-2, PDGFRA, PDGFRB, c-KIT/SCFR, INSR (insulin receptor), IGF-IR, IGF-IIR, IRR (insulin receptor-related receptor), CSF-1R, FGFR-1, FGFR-2, FGFR-3, FGFR-4, HGFR-1, HGFR-2, CCK4, TRK-A, TRK-B, TRK-C, MET, RON, EPHA-1, EPHA-2, EPHA-3, EPHA-4, EPHA-5, EPHA-6, EPHA-7, EPHA-8, EPHB-1, EPHB-2, EPHB-3, EPHB-4, EPHB-5, EPHB-6, AXL, MER, TYRO3, TIE-1, TIE-2, TEK, RYK, DDR-1, DDR-2, RET, c-ROS, LTK (leukocyte tyrosine kinase), ALK (anaplastic lymphoma kinase), ROR-1, ROR-2, MUSK, CD28, and RTK 106, as well as neurotrophin receptors, G-protein coupled receptors, adrenergic receptors, olfactory receptors, NMDA receptors, Toll-like receptors, T cell receptors, and the like.

Ligands specific for other targets can also be identified using the OBOC combinatorial library method. Examples include, but are not limited to, ligands that bind to target proteins on pathogens, microbial agents, or infectious agents (e.g., viruses, bacteria, fungi, parasites, etc.); ligands that bind to target protein aggregates such as amyloid or prion aggregates or any other proteinaceous aggregate associated with a neurological disorder; ligands that bind to target toxins or metabolites derived from a subject's metabolism or from the metabolism of a pathogen, microbial agent, or infectious agent; and ligands that bind to target poisonous agents such as snake venom or drugs.

Accordingly, some embodiments of the invention provide nanoparticles including PVA having one or more cellular targeting moieties as described above, wherein each cellular targeting moiety is independently selected from an antibody, a peptidomimetic moiety, a folic acid moiety, and a peptide. In some embodiments, each cellular targeting moiety is independently selected from LLP2A, bombesin, LXY1, LXY3, LXY4, LXY30, LXW7, OA02, luteinizing-hormone-releasing hormone (LHRH), a melanocyte-stimulating hormone (MSR), folic acid, prostate-specific membrane antigen (PSMA)-targeted ligand, and a PSMA-targeted antibody.

The nanoparticles of the present invention can also contain imaging agents or other diagnostic agents. An imaging agent used in the present invention can include any imaging agent known in the art, as provided, for example, in the following references: Armstrong et al., *Diagnostic Imaging*, 5$^{th}$ Ed., Blackwell Publishing (2004); Torchilin, V. P., Ed., *Targeted Delivery of Imaging Agents*, CRC Press (1995); Vallabhajosula, S., *Molecular Imaging: Radiopharmaceuticals for PET and SPECT*, Springer (2009). An imaging agent can be detected by a variety of ways, including as an agent providing and/or enhancing a detectable signal that includes, but is not limited to, gamma-emitting, radioactive, echogenic, optical, fluorescent, absorptive, magnetic or tomography signals. Imaging techniques that are useful for detecting the nanoparticles of the invention include, but are not limited to, single photon emission computed tomography (SPECT), magnetic resonance imaging (MRI), optical imaging, positron emission tomography (PET), computed tomography (CT), x-ray imaging, gamma ray imaging, and the like.

In some embodiments, the imaging agent can include chelators that bind to metal ions to be used for a variety of diagnostic imaging techniques. Exemplary chelators include but are not limited to ethylenediaminetetraacetic acid (EDTA), [4-(1,4,8,11-tetraazacyclotetradec-1-yl) methyl] benzoic acid (CPTA), cyclohexanediaminetetraacetic acid (CDTA), ethylenebis(oxyethylenenitrilo)tetraacetic acid (EGTA), diethylenetriaminepentaacetic acid (DTPA), citric acid, hydroxyethyl ethylenediamine triacetic acid (HEDTA), iminodiacetic acid (IDA), triethylene tetraamine hexaacetic acid (TTHA), 1,4,7, 10-tetraazacyclododecane-1,4,7,10-tetra(methylene phosphonic acid) (DOTP), 1,4,8,11-tetraazacyclododecane-1,4,8,11-tetraacetic acid (TETA), 1,4,7, 10-tetraazacyclododecane-1,4,7,10-tetraacetic acid (DOTA), and derivatives thereof.

A radioisotope can be incorporated into some of the imaging agents described herein and can include radionuclides that emit gamma rays, positrons, beta and alpha particles, and X-rays. Suitable radionuclides include but are not limited to $^{225}$Ac, $^{72}$As, $^{211}$At, $^{11}$B, $^{128}$Ba, $^{212}$Bi, $^{75}$Br, $^{77}$Br, $^{14}$C, $^{109}$Cd, $^{62}$Cu, $^{64}$Cu, $^{67}$Cu, $^{18}$F, $^{67}$Ga, $^{68}$Ga, $^{3}$H, $^{123}$I, $^{125}$I, $^{130}$I, $^{131}$I, $^{111}$In, $^{177}$, $^{13}$N, $^{15}$O, $^{32}$P, $^{212}$Pb, $^{103}$Pd, $^{223}$Ra, $^{186}$Re, $^{188}$Re, $^{47}$Sc, $^{153}$Sm, $^{89}$Sr, $^{99m}$Tc, $^{88}$Y and $^{90}$Y. In certain embodiments, radioactive agents can include $^{111}$In-DTPA, $^{99m}$Tc(CO)$_3$-DTPA, $^{99m}$Tc(CO)$_3$-ENP2, $^{62/64/67}$Cu-TETA, $^{99m}$Tc(CO)$_3$-IDA, and $^{99m}$Tc(CO)$_3$triamines (cyclic or linear). In other embodiments, the agents can include DOTA and its various analogs with $^{111}$In, $^{177}$Lu, $^{153}$Sm, $^{88/90}$Y, $^{62/64/67}$Cu, or $^{67/68}$Ga.

In other embodiments, the imaging moieties can include optical agents such as fluorescent agents, phosphorescent agents, chemiluminescent agents, and the like. Numerous agents (e.g., dyes, probes, labels, or indicators) are known in the art and can be used in the present invention. (See, e.g., Invitrogen, The Handbook—A Guide to Fluorescent Probes and Labeling Technologies, Tenth Edition (2005)). Fluorescent agents can include a variety of organic and/or inorganic small molecules or a variety of fluorescent proteins and derivatives thereof. For example, fluorescent agents can include but are not limited to cyanines, phthalocyanines, porphyrins, indocyanines, rhodamines, phenoxazines, phenykanthenes, phenothiazines, phenoselenazines, fluoresceins, benzoporphyrins, squaraines, dipyrrolo pyrimidones, tetracenes, quinolines, pyrazines, corrins, croconiums, acridones, phenanthridines, rhodamines, acridines, anthraquinones, chalcogenopyrylium analogues, chlorins, naphthalocyanines, methine dyes, indolenium dyes, azo compounds, azulenes, azaazulenes, triphenyl methane dyes, indoles, benzoindoles, indocarbocyanines, benzoindocarbocyanines, and BODIPY™ derivatives having the general structure of 4,4-difluoro-4-bora-3a,4a-diaza-s-indacene, and/or conjugates and/or derivatives of any of these. Other agents that can be used include, but are not limited to, for example, fluorescein, fluorescein-polyaspartic acid conjugates, fluorescein-polyglutamic acid conjugates, fluorescein-polyarginine conjugates, indocyanine green, indocyanine-dodecaaspartic acid conjugates, indocyanine-polyaspartic acid conjugates, isosulfan blue, indole disulfonates, benzoindole disulfonate, bis(ethylcarboxymethyl)indocyanine, bis(pentylcarboxymethyl)indocyanine, polyhydroxyindole sulfonates, polyhydroxybenzoindole sulfonate, rigid heteroatomic indole sulfonate, indocyaninebispropanoic acid, indocyaninebishexanoic acid, 3,6-dicyano-2,5-[(N,N,N',N'-tetrakis(carboxymethyl)amino]pyrazine, 3,6-[(N,N,N',N'-tetrakis(2-hydroxyethyl)amino]pyrazine-2,5-dicarboxylic acid, 3,6-bis(N-azatedino)pyrazine-2,5-dicarboxylic acid, 3,6-bis(N-morpholino)pyrazine-2,5-dicarboxylic acid, 3,6-bis(N-piperazino)pyrazine-2,5-dicarboxylic acid, 3,6-bis(N-thiomorpholino)pyrazine-2,5-dicarboxylic acid, 3,6-bis(N-thiomorpholino)pyrazine-2,5-dicarboxylic acid S-oxide, 2,5-dicyano-3,6-bis(N-thiomorpholino)pyrazine S,S-dioxide, indocarbocyaninetetrasulfonate, chloroindocarbocyanine, and 3,6-diaminopyrazine-2,5-dicarboxylic acid.

One of ordinary skill in the art will appreciate that particular optical agents used can depend on the wavelength used for excitation, depth underneath skin tissue, and other factors generally well known in the art. For example, optimal absorption or excitation maxima for the optical agents can vary depending on the agent employed, but in general, the optical agents of the present invention will absorb or be excited by light in the ultraviolet (UV), visible, or infrared (IR) range of the electromagnetic spectrum. For imaging, dyes that absorb and emit in the near-IR (~700-900 nm, e.g., indocyanines) preferred. For topical visualization using an endoscopic method, any dyes absorbing in the visible range are suitable.

In some embodiments, the non-ionizing radiation ranging in wavelength from about 350 nm to about 1200 nm can be used to detect fluorescent imaging moieties. For example, the fluorescent agent can be excited by light having a wavelength in the blue range of the visible portion of the electromagnetic spectrum (from about 430 nm to about 500 nm) and emits at a wavelength in the green range of the visible portion of the electromagnetic spectrum (from about 520 nm to about 565 nm). For example, fluorescein dyes can be excited with light with a wavelength of about 488 nm and have an emission wavelength of about 520 nm. As another example, 3,6-diaminopyrazine-2,5-dicarboxylic acid can be excited with light having a wavelength of about 470 nm and fluoresces at a wavelength of about 532 inn. The excitation and emission wavelengths of the optical agent can also fall in the near-infrared range of the electromagnetic spectrum. For example, indocyanine dyes, such as indocyanine green, can be excited with light with a wavelength of about 780 nm and have an emission wavelength of about 830 nm.

The imaging moieties can also include magnetic resonance (MR) and x-ray contrast agents that are generally well known in the art, including, for example, iodine-based x-ray contrast agents, superparamagnetic iron oxide (SPIO), complexes of gadolinium or manganese, and the like. (See, e.g., Armstrong et al., *Diagnostic Imaging*, 5$^{th}$ Ed., Blackwell Publishing (2004)). In some embodiments, an imaging moiety can include a magnetic resonance (MR) imaging agent. Exemplary magnetic resonance agents include but are not limited to paramagnetic agents, superparamagnetic agents, and the like. Exemplary paramagnetic agents can include but are not limited to gadopentetic acid, gadoteric acid, gadodiamide, gadolinium, gadoteridol mangafodipir, gadoversetamide, ferric ammonium citrate, gadobenic acid, gadobutrol, or gadoxetic acid. Superparamagnetic agents can include but are not limited to superparamagnetic iron oxide and ferristene. In certain embodiments, the diagnostic agents can include x-ray contrast agents as provided, for example, in the following references: H. S Thomsen, R. N. Muller and R. F. Mattrey, Eds., *Trends in Contrast Media*, (Berlin: Springer-Verlag, 1999); P. Dawson, D. Cosgrove and R. Grainger, Eds, *Textbook of Contrast Media* (ISIS Medical Media 1999); Torchilin, V. P., *Curr. Pharm. Biotech.* 1:183-215 (2000); Bogdanov, A. A. et al., *Adv. Drug Del. Rev.* 37:279-293 (1999); Sachse, A. et al., *Investigative Radiology* 32(1):44-50 (1997). Examples of x-ray contrast agents include, without limitation, iopamidol, iomeprol, iohexol, iopentol, iopromide, iosimide, ioversol, iotrolan, iotasul, iodixanol, iodecimol, ioglucamide, ioglunide, iogulamide, iosarcol, ioxilan, iopamiron, metrizamide, iobitridol and iosimenol.

In some embodiments, the invention provides nanoparticles including PVA having one or more imaging moieties as described above, wherein the imaging moiety includes a fluorophore.

In some embodiments, the nanoparticle further includes a branched polymeric crosslinker having from 2 to 4 branches and one boronic acid moiety per branch.

V. METHODS FOR TREATING DISEASES

The invention also provides a method for treating a disease including administering a therapeutically effective amount of a nanoparticle of the invention to a subject in need thereof.

Other diseases that can be treated by the nanocarriers of the present invention include: (1) inflammatory or allergic diseases such as systemic anaphylaxis or hypersensitivity responses, drug allergies, insect sting allergies; inflammatory bowel diseases, such as Crohn's disease, ulcerative colitis, ileitis and enteritis; vaginitis; psoriasis and inflammatory dermatoses such as dermatitis, eczema, atopic dermatitis, allergic contact dermatitis, urticaria; vasculitis; spondyloarthropathies, scleroderma, respiratory allergic diseases such as asthma, allergic rhinitis, hypersensitivity lung diseases, and the like, (2) autoimmune diseases, such as arthritis (rheumatoid and psoriatic), osteoarthritis, multiple sclerosis, systemic lupus erythematosus, diabetes mellitus, glomerulonephritis, and the like, (3) graft rejection (including allograft rejection and graft-v-host disease), and (4) other diseases in which undesired inflammatory responses are to be inhibited (e.g., atherosclerosis, myositis, neurological conditions such as stroke and closed-head injuries, neurodegenerative diseases, Alzheimer's disease, encephalitis, meningitis, osteoporosis, gout, hepatitis, nephritis, sepsis, sarcoidosis, conjunctivitis, otitis, chronic obstructive pulmonary disease, sinusitis and Behcet's syndrome). In some embodiments, the disease can be cancer. In other embodiments, the disease can be bladder cancer or ovarian cancer.

In addition, the nanocarriers of the present invention are useful for the treatment of infection by pathogens such as viruses, bacteria, fungi, and parasites. Other diseases can be treated using the nanocarriers of the present invention.

In some embodiments, the disease is selected from cancer, a viral infection, and a bacterial infection.

In some embodiments, the disease is cancer.

VI. METHODS FOR PHOTODYNAMIC THERAPY AND PHOTOTHERMAL THERAPY

In addition, the invention provides a method of treating a disease via photodynamic or photothermal therapy including administering to a subject in need thereof a therapeutically effective amount of a nanoparticle of the invention, wherein the nanoparticle has a porphyrin, and exposing the subject to radiation, thereby treating the disease via photodynamic or photothermal therapy.

The methods of treatment using the nanocarriers of the present invention also include treating a disease by photodynamic therapy or photothermal therapy. The methods generally involve administering a nanocarrier of the present invention to a subject, and then exposing the subject to radiation of a specific wavelength to induce the photodynamic or photothermal therapy depending on the wavelength of light. Upon exposure to the radiation or light, the porphyrins used in the nanocarriers of the present invention, either complexed to a metal or not, generate either the reactive singlet oxygen suitable for photodynamic therapy, or generate heat sufficient of photothermal therapy. In some embodiments, the present invention provides a method of treating a disease via photodynamic or photothermal therapy, including administering to a subject in need thereof, a therapeutically effective amount of a nanocarrier of the present invention, and exposing the subject to radiation, thereby treating the disease via photodynamic or photothermal therapy. In some embodiments, the method is a method of treating a disease via photodynamic therapy. In other embodiments, the method is a method of treating a disease via photothermal therapy.

In some embodiments, the disease is cancer. The nanocarriers of the present invention can be administered to a subject for treatment, e.g., of hyperproliferative disorders including cancer such as, but not limited to: carcinomas, gliomas, mesotheliomas, melanomas, lymphomas, leukemias, adenocarcinomas, breast cancer, ovarian cancer, cervical cancer, glioblastoma, leukemia, lymphoma, prostate cancer, and Burkitt's lymphoma, head and neck cancer, colon cancer, colorectal cancer, non-small cell lung cancer, small cell lung cancer, cancer of the esophagus, stomach cancer, pancreatic cancer, hepatobiliary cancer, cancer of the gallbladder, cancer of the small intestine, rectal cancer, kidney cancer, bladder cancer, prostate cancer, penile cancer, urethral cancer, testicular cancer, cervical cancer, vaginal cancer, uterine cancer, ovarian cancer, thyroid cancer, parathyroid cancer, adrenal cancer, pancreatic endocrine cancer, carcinoid cancer, bone cancer, skin cancer, retinoblastomas, multiple myelomas, Hodgkin's lymphoma, and non-Hodgkin's lymphoma (see, CANCER: PRINCIPLES AND PRACTICE (DeVita, V. T. et al. eds 2008) for additional cancers).

In some embodiments, the invention provides a method of detecting a tumor in a subject including administering to the subject an effective amount of a nanoparticle of the invention and detecting the nanoparticle (tumor?) via fluorescence imaging (spectroscopy?). In related embodiments, the invention provides a method of detecting a tumor in a subject including administering to the subject an effective amount of a nanoparticle of the invention and detecting the nanoparticle (tumor?) via magnetic resonance imaging. In related embodiments, the invention provides a method of detecting a tumor in a subject including administering to the subject an effective amount of a nanoparticle of the invention and detecting the nanoparticle (tumor?) via positron emission tomography. In certain embodiments, nanoparticles contain PVA having a structure according to Formula III wherein the subscript y is an integer ranging from 1 to about 400.

The nanocarriers of the invention can be administered at any suitable dose in the methods of the invention. In general, the nanocarriers are administered such that the dose of boronic acid-containing drug, porphyrin, or other active agent ranges from about 0.1 milligrams to about 1000 milligrams per kilogram of a subject's body weight (i.e., about 0.1-1000 mg/kg). The dose of the active agent can be, for example, about 0.1-1000 mg/kg, or about 1-500 mg/kg, or about 25-250 mg/kg, or about 50-100 mg/kg. The dose of the active agent can be about 1, 2, 3, 4, 5, 10, 15, 20, 25, 30, 35, 40, 45, 50, 55, 60, 65, 70, 75, 85, 90, 95, 100, 150, 200, 250, 300, 350, 400, 450, 500, 550, 600, 650, 700, 750, 800, 850, 900, 950 or 1000 mg/kg.

The dosages can be varied depending upon the requirements of the patient, the severity of the disorder being treated, and the particular formulation being administered. The dose administered to a patient should be sufficient to result in a beneficial therapeutic response in the patient. The size of the dose will also be determined by the existence, nature, and extent of any adverse side-effects that accompany the administration of the drug in a particular patient. Determination of the proper dosage for a particular situation is within the skill of the typical practitioner. The total dosage can be divided and administered in portions over a period of time suitable to treat to a particular condition.

Administration of the nanocarriers can be conducted for a period of time which will vary depending upon the nature of the particular nanocarrier and active agent, as well as on the particular disorder, its severity and the overall condition of the patient. Administration can be conducted, for example, hourly, every 2 hours, three hours, four hours, six hours, eight hours, or twice daily including every 12 hours, or any intervening interval thereof. Administration can be conducted once daily, or once every 36 hours or 48 hours, or once every month or several months. Following treatment, a patient can be monitored for changes in his or her condition and for alleviation of the symptoms of the disorder. The dosage can either be increased in the event the patient does not respond significantly to a particular dosage level, or the dose can be decreased if an alleviation of the symptoms of the disorder is observed, or if the disorder has been ablated, or if unacceptable side effects are seen with a particular dosage.

A therapeutically effective amount of a nanocarrier can be administered to the subject in a treatment regimen comprising intervals of at least 1 hour, or 6 hours, or 12 hours, or 24 hours, or 36 hours, or 48 hours between dosages. Administration can be conducted at intervals of at least 72, 96, 120, 168, 192, 216, or 240 hours, or the equivalent amount of days. The dosage regimen can consist of two or more different interval sets. For example, a first part of the dosage regimen can be administered to a subject multiple times daily, daily, every other day, or every third day. The dosing regimen can start with dosing the subject every other day, every third day, weekly, biweekly, or monthly. The first part of the dosing regimen can be administered, for example, for up to 30 days, such as 7, 14, 21, or 30 days. A subsequent second part of the dosing regimen with a different interval administration administered weekly, every 14 days, or monthly can optionally follow, continuing for 4 weeks up to two years or longer, such as 4, 6, 8, 12, 16, 26, 32, 40, 52, 63, 68, 78, or 104 weeks. Alternatively, if the disorder goes into remission or generally improves, the dosage may be maintained or kept at lower than maximum amount. If the condition relapses, the first dosage regimen can be resumed until an improvement is seen, and the second dosing regimen can be implemented again. This cycle can be repeated multiple times as necessary.

The present invention also provides pharmaceutical compositions for the administration of the nanocarriers of the invention. The pharmaceutical compositions can be prepared by any of the methods well known in the art of pharmacy and drug delivery. In general, methods of preparing the compositions include the step of bringing the nanocarriers, including drug-loaded nanocarriers, into association with one or more accessory ingredients. The pharmaceutical compositions are typically prepared by uniformly and intimately bringing the active ingredient into association with a liquid base or a finely divided solid base or both, and then, if necessary, shaping the product into the desired formulation. The compositions can be conveniently prepared and/or packaged in unit dosage form.

The pharmaceutical compositions can be in the form of a sterile injectable aqueous or oleaginous solutions and suspensions. Sterile injectable preparations can be formulated using non-toxic parenterally-acceptable vehicles including water, Ringer's solution, and isotonic sodium chloride solution, and acceptable solvents such as 1,3-butane diol. In certain embodiments, the pharmaceutical composition includes an aqueous solution without an organic solvent. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables.

Aqueous suspensions contain the nanocarriers in admixture with excipients suitable for the manufacture of aqueous suspensions. Such excipients include, but are not limited to: suspending agents such as sodium carboxymethylcellulose, methylcellulose, oleagino-propylmethylcellulose sodium alginate, polyvinyl-pyrrolidone, gum tragacanth and gum acacia; dispersing or wetting agents such as lecithin, polyoxyethylene stearate, and polyethylene sorbitan monooleate; and preservatives such as ethyl, n-propyl, and p-hydroxybenzoate.

Oily suspensions can be formulated by suspending the nanocarriers in a vegetable oil, for example, arachis oil, olive oil, sesame oil or coconut oil, or in a mineral oil such as liquid paraffin. The oily suspensions can contain a thickening agent, for example beeswax, hard paraffin or cetyl alcohol. These compositions can be preserved by the addition of an anti-oxidant such as ascorbic acid.

Dispersible powders and granules (suitable for preparation of an aqueous suspension by the addition of water) can contain the nanocarriers in admixture with a dispersing agent, wetting agent, suspending agent, or combinations thereof. Additional excipients can also be present.

The pharmaceutical compositions of the invention can also be in the form of oil-in-water emulsions. The oily phase can be a vegetable oil, for example olive oil or arachis oil, or a mineral oil, for example liquid paraffin or mixtures of these. Suitable emulsifying agents can be naturally-occurring gums, such as gum acacia or gum tragacanth; naturally-occurring phospholipids, such as soy lecithin; esters or partial esters derived from fatty acids and hexitol anhydrides, such as sorbitan monooleate; and condensation products of said partial esters with ethylene oxide, such as polyoxyethylene sorbitan monooleate.

Pharmaceutical compositions containing the nanocarriers of the invention can also be in a form suitable for oral use. Suitable compositions for oral administration include, but are not limited to, tablets, troches, lozenges, aqueous or oily suspensions, dispersible powders or granules, emulsions, hard or soft capsules, syrups, elixirs, solutions, buccal patches, oral gels, chewing gums, chewable tablets, effervescent powders, and effervescent tablets. Compositions for oral administration can be formulated according to any method known to those of skill in the art. Such compositions can contain one or more agents selected from sweetening agents, flavoring agents, coloring agents, antioxidants, and preserving agents in order to provide pharmaceutically elegant and palatable preparations.

Tablets generally contain the nanocarriers, including drug-loaded nanocarriers, in admixture with non-toxic pharmaceutically acceptable excipients, including: inert diluents, such as cellulose, silicon dioxide, aluminum oxide, calcium carbonate, sodium carbonate, glucose, mannitol, sorbitol, lactose, calcium phosphate, and sodium phosphate; granulating and disintegrating agents, such as corn starch and alginic acid; binding agents, such as polyvinylpyrrolidone (PVP), cellulose, polyethylene glycol (PEG), starch, gelatin, and acacia; and lubricating agents such as magnesium stearate, stearic acid, and talc. The tablets can be uncoated or coated, enterically or otherwise, by known techniques to delay disintegration and absorption in the gastrointestinal tract and thereby provide a sustained action over a longer period. For example, a time delay material such as glyceryl monostearate or glyceryl distearate can be employed. Tablets can also be coated with a semi-permeable membrane and optional polymeric osmogents according to known techniques to form osmotic pump compositions for controlled release.

Compositions for oral administration can be formulated as hard gelatin capsules wherein the active ingredient is mixed with an inert solid diluent (such as calcium carbonate, calcium phosphate, or kaolin), or as soft gelatin capsules wherein the active ingredient is mixed with water or an oil medium (such as peanut oil, liquid paraffin, or olive oil).

Transdermal delivery of the nanocarriers, including drug-loaded nanocarriers, can be accomplished by means of iontophoretic patches and the like. The nanocarriers can also be administered rectally using suppository compositions. These compositions can be prepared by mixing the nanocarriers with a suitable non-irritating excipient which is solid at ordinary temperatures but liquid at the rectal temperature and will therefore melt in the rectum to release the drug. Such materials include, but are not limited to, cocoa butter and polyethylene glycols.

VII. EXAMPLES

Example 1

Targeting Nanoformulation of Boronic Acid Containing Drugs Based on Poly(Vinyl Alcohol)

Scheme 4 shows a schematic representation of the conjugation of cancer targeting ligand on the PVA via "click chemistry" and loading of boronic acid containing drugs via boronate ester bonds formed between the boronic acid moiety of BTZ and the cis-diol groups of PVA.

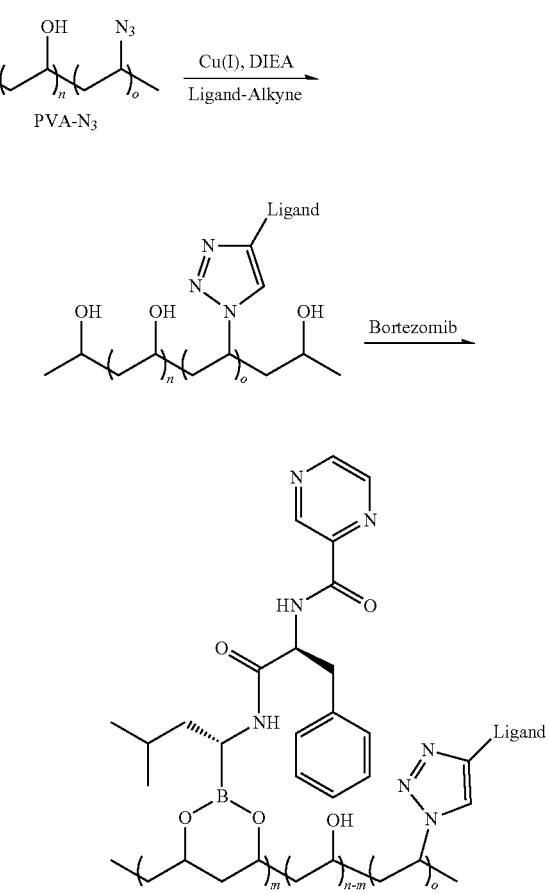

Scheme 5 shows a schematic representation of the conjugation of cancer targeting ligands to and loading of BTZ on PVA via boronate ester bond formation.

Scheme 5

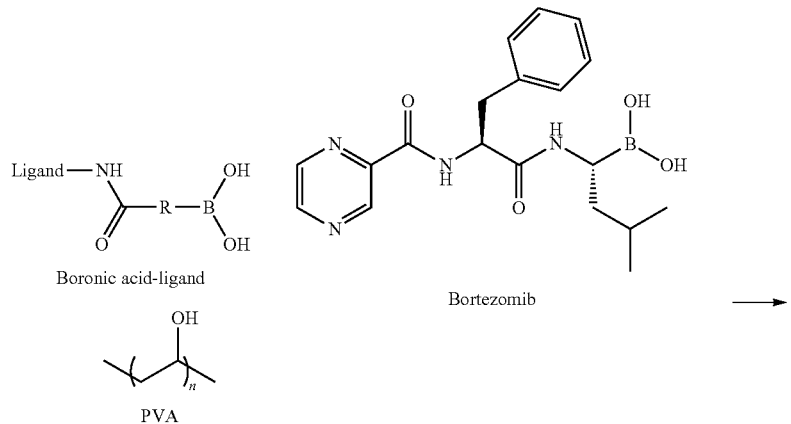

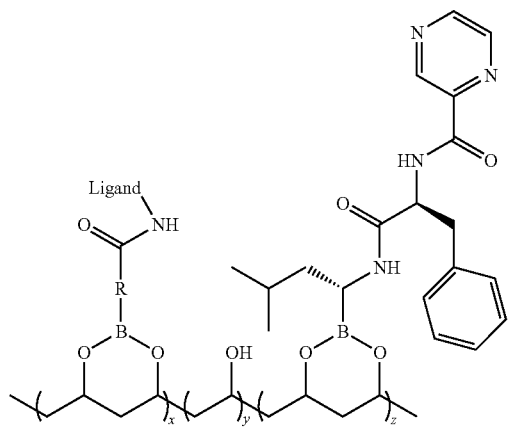

For certain particles, the molecular weights of PVA can range from 27 KDa to 180 KDa.

The boronic acid containing drugs include, but are not limited to, proteasome inhibitors (e.g., bortezomib), arginase inhibitors (e.g., 2(S)-amino-6-boronohexanoic acid (ABH), S-(2-boronoethyl)-L-cysteine (BEC)) and β-lactamase inhibitor.

Cancer targeting ligands include, but are not limited to, antibodies, LLP2A, LXY1, LXY3, LXY4, LXW7, OAO2, LHRH, MSH, Bombesin, and folic acid.

Boronic acids of the boronic acid containing ligands include, but are not limited to, 4-carboxyphenylboronic acid, 3-carboxy-5-nitrophenylboronic acid, and 4-carboxy-2-nitrophenylboronic acid.

Scheme 6 shows the chemical structure of certain boronic acid-containing therapeutic agents that can be loaded into PVA carriers. The boronic acid containing drugs, such as bortezomib (BTZ) can be loaded on PVA via boronate ester bonds formed between boronic acid of BTZ and cis-diols of PVA. In brief, BTZ was dissolved in ethanol and then the solution was added into PVA aqueous solution. The ethanol was removed by evaporation. The unbound drug was removed by filtration.

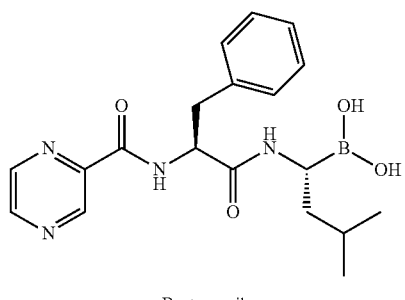

Serine protease inhibitor
Beta-lactamase inhibitor

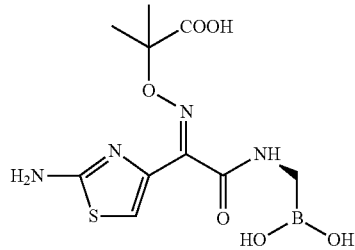

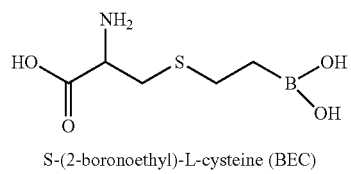

S-(2-boronoethyl)-L-cysteine (BEC)

Example 2

Bortezomib-Loaded PVA Nanoparticles

FIG. 1(A) shows the size of BTZ loaded PVA (27 KDa) in fresh PBS containing 10% ethanol (closed squares). The boronic acid containing drugs, such as bortezomib (BTZ) can be loaded on PVA via boronate ester bonds formed between boronic acid of BTZ and cis-diols of PVA. Briefly, BTZ (1 mg) was first dissolved in ethanol (0.1 mL) under sonication, added to the PBS solution (0.9 mL) of PVA (27 KDa), and then dialyzed against PBS buffer for 3 hours. Unbound free BTZ was removed via column filtration with a 10 kDa molecular weight cutoff membrane. FIG. 1(B) shows the size of BTZ loaded PVA (27 KDa) re-hydrated from lyophilized powder, measured by dynamic light scattering (DLS, Microtrac; closed circles). The final PVA concentration was kept at 10 mg/mL.

Figure 2:
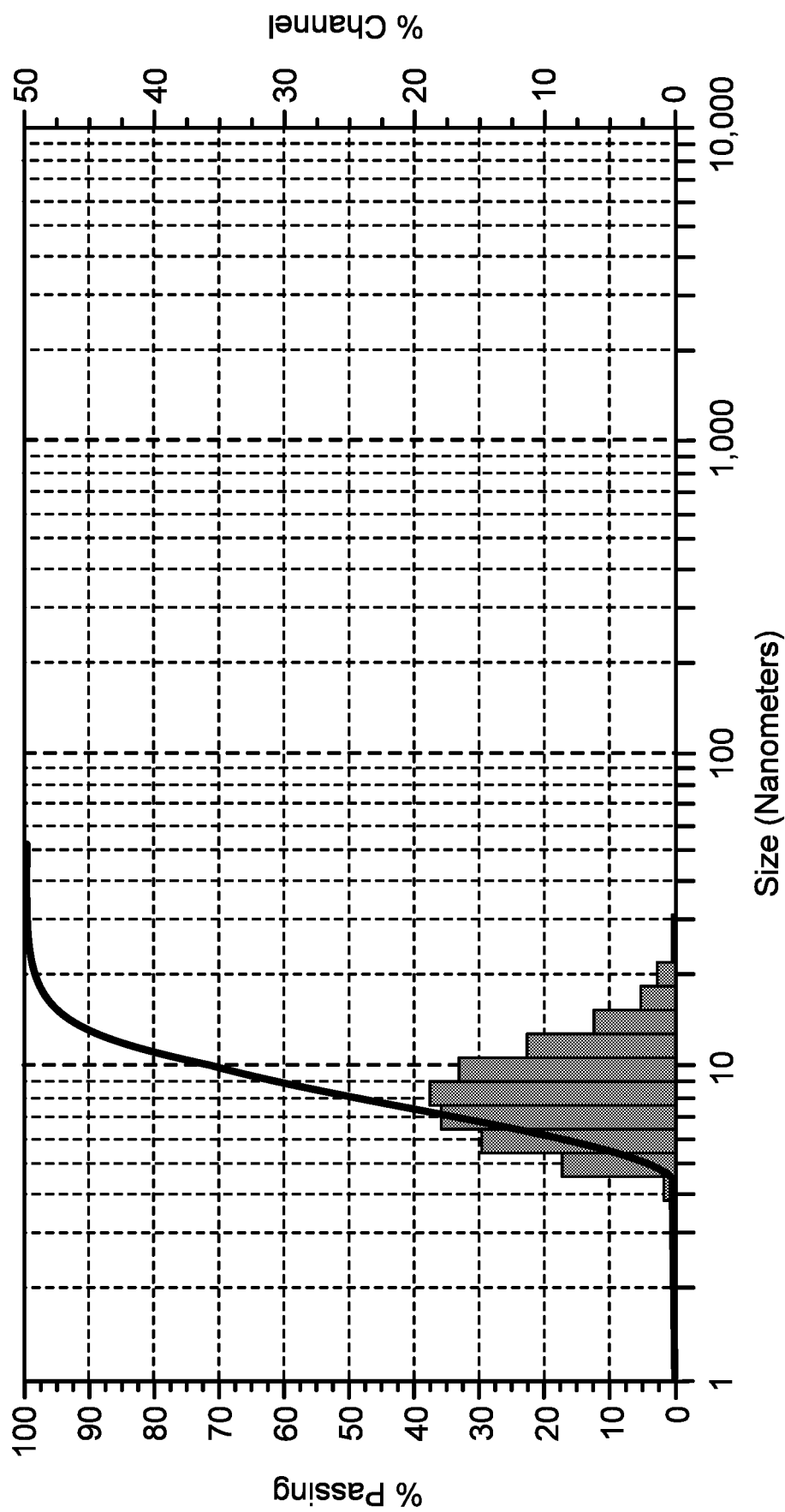
FIG. 2 shows the particle size distribution of bortezomib-loaded PVA particles.
Figure 3:
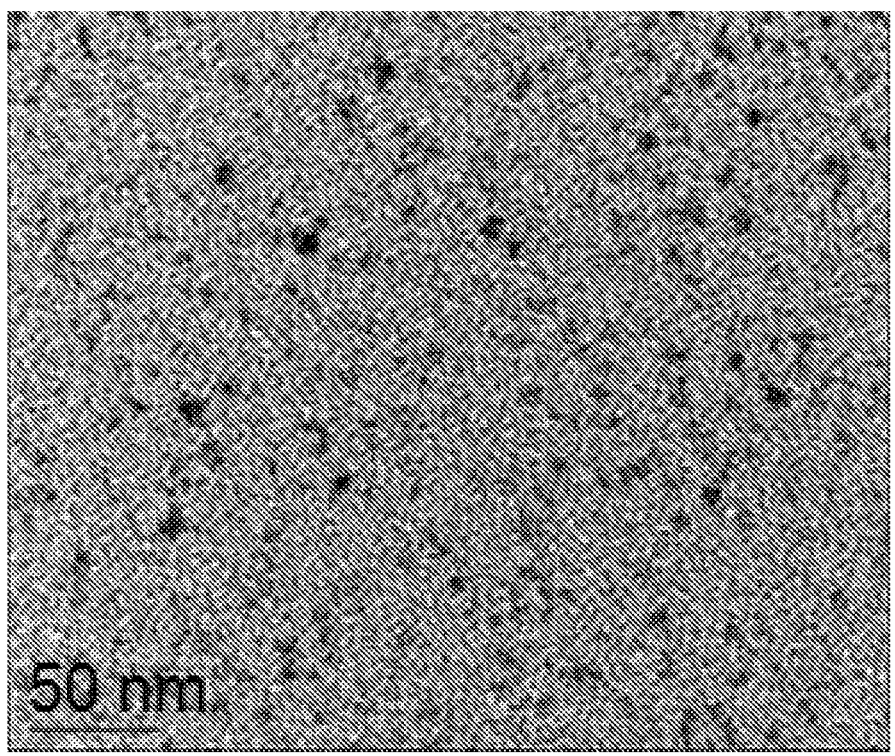
FIG. 3 shows the morphology of bortezomib-loaded PVA particles.

FIG. 2 shows the particle size distribution of BTZ-loaded PVA nanoformulation as characterized by DLS. FIG. 3 shows the morphology of BTZ-loaded PVA nanoformulation as observed by TEM. The BTZ loading level was 1 mg/ml BTZ in 20 mg/ml PVA polymer. The procedure for nanoparticle preparation is similar to that described for FIG. 1A.

Figure 4A:
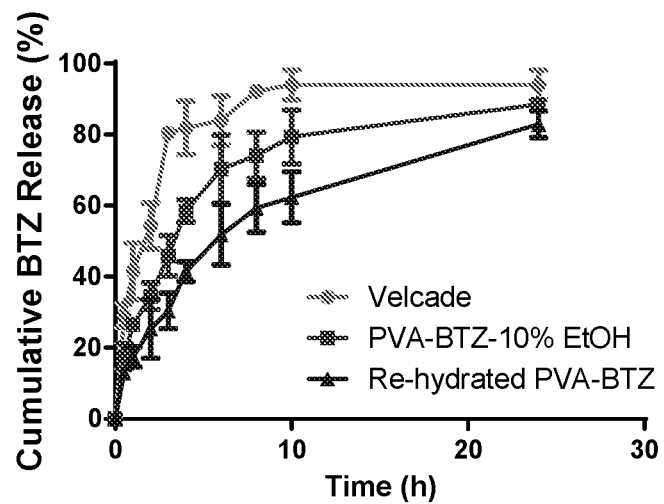
FIG. 4(A) shows a comparison of cumulative drug release profiles for the bortezomib-PVA formulations of the present invention and a clinical bortezomib formulation.
Figure 4B:
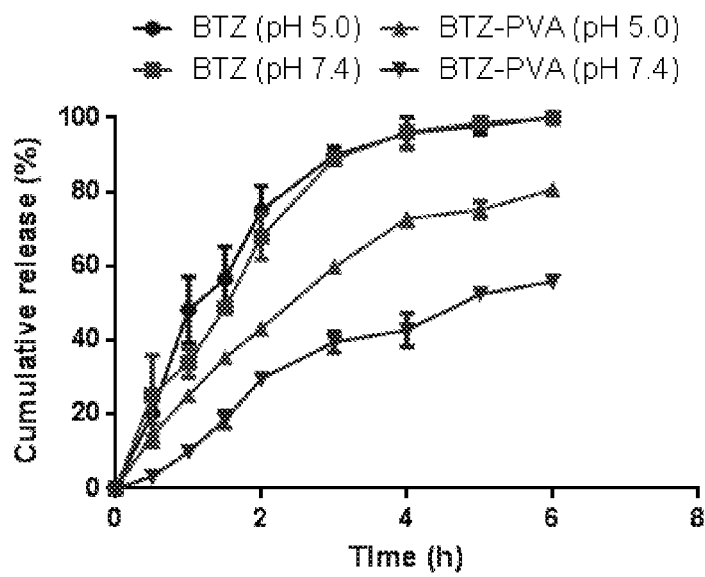
FIG. 4(B) shows a comparison of cumulative drug release profiles for bortezomib-PVA formulations of the invention.

FIG. 4(A) shows cumulative BTZ release profiles from Velcade® (clinical free drug form of BTZ formulated with mannitol) and two PVA formulations of BTZ in PBS medium at pH 7.4. The molecular weight of PVA was 27 KDa. BTZ release from Velcade® was rapid and about 80% of BTZ was released within the first 3 h. In contrast, BTZ release from the two PVA formulations was much slower. FIG. 4(B) shows cumulative BTZ release profiles from Velcade® and PVA nanoformulation of BTZ at different pH (7.4, 5.0).

Figure 5A:
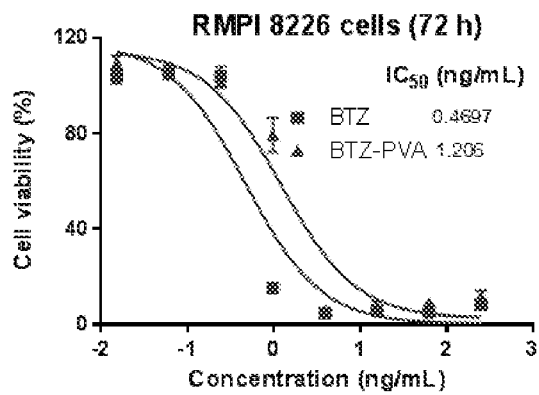
FIG. 5(A) shows the viability of RMPI 8226 cells after incubation with the bortezomib-PVA formulations of the present invention and a clinical bortezomib formulation.
Figure 5B:
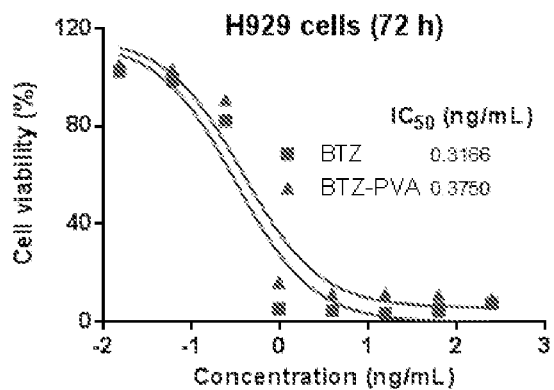
FIG. 5(B) shows the viability of H929 cells after incubation with the bortezomib-PVA formulations of the present invention and a clinical bortezomib formulation.
Figure 5C:
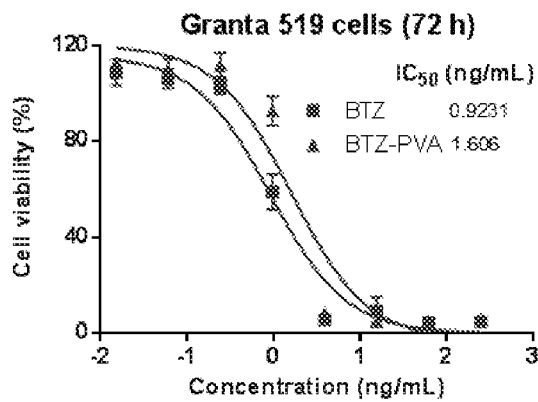
FIG. 5(C) shows the viability of Granta 519 cells after incubation with the bortezomib-PVA formulations of the present invention and a clinical bortezomib formulation.

FIG. 5 shows MTT assay results indicating the viability of multiple myeloma cells RMPI8226 (A), H929 (B), and mantle cell lymphoma cells Granta 519 (C) after 72 h continuous incubation with different concentrations of Velcade® and BTZ PVA nanoformulation. The cell viability was calculated as the ratio of cell number in the treated sample divided by that in the untreated control. Values reported are the mean±SD for triplicate samples. PVA formulations of BTZ exhibited comparable in vitro antitumor effects against these cells as the clinical free drug form of BTZ (Velcade®).

Figure 6A:
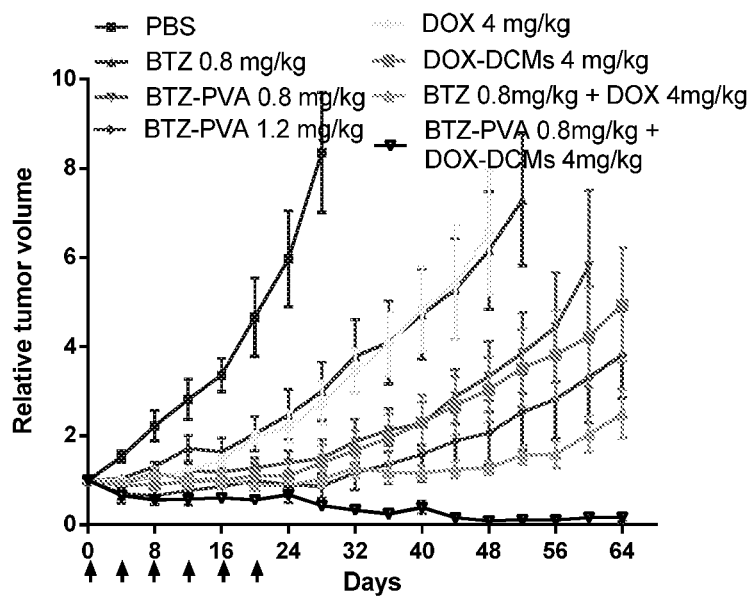
FIG. 6(A) shows in vivo tumor growth inhibition of subcutaneous RMPI8226 multiple myeloma bearing mice after intravenous treatment of BTZ-PVA nanoformulations with or without combination of doxorubicin (DOX, or DOX-loaded micelles).
Figure 6B:
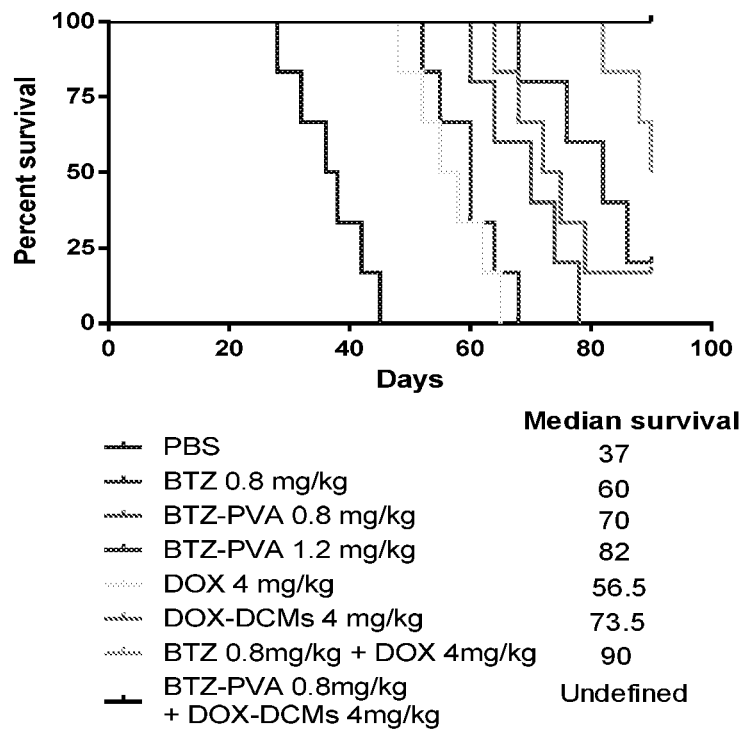
FIG. 6(B) shows Kaplan-Meier survival curves of subcutaneous RMPI8226 multiple myeloma bearing mice after intravenous treatment of BTZ-PVA nanoformulations with or without combination of doxorubicin (DOX, or DOX-loaded micelles).
Figure 6C:
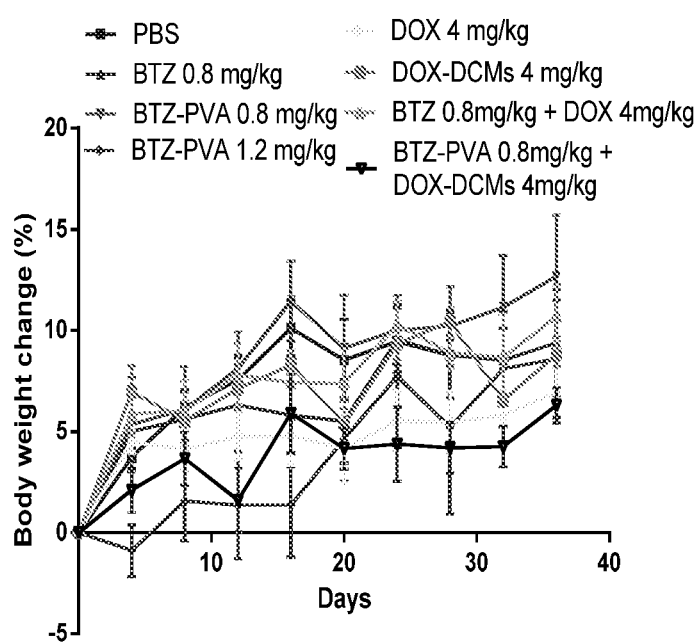
FIG. 6(C) shows body weight changes of subcutaneous RMPI8226 multiple myeloma bearing mice after intravenous treatment of BTZ-PVA nanoformulations with or without combination of doxorubicin (DOX, or DOX-loaded micelles).

FIG. 6 shows in viva tumor growth inhibition (A), Kaplan-Meier survival curves (B), and body weight changes (C) of subcutaneous RMPI8226 multiple myeloma bearing mice after intravenous treatment of BTZ-PVA nanoformulations with or without combination of doxorubicin (DOX, or DOX-loaded micelles). Tumor bearing mice (n=6-8) were intravenously administered PBS; Velcade® (0.8 mg/kg); BTZ-PVA (0.8, 1.2 mg/kg); DOX (4 mg/kg); DOX-DCMs (4 mg/kg); BTZ 0.8 mg/kg followed by DOX 4 mg/kg 24 h later; or BTZ-PVA 0.8 mg/kg followed by DOX-DCMs 24 h later every four days for a total of 6 doses. Data represent mean±SEM. The PVA formulation of BTZ was found to be more efficacious than Velcade® against RAPI8226 multiple myeloma. The combination of BTZ-PVA with DOX-DCMs exhibited the best tumor growth inhibition and longest survival time among all these treatment groups.

TABLE 1

Blood cell count after the last dosage in the therapeutic study

| Groups | WBC (K/µl) | Neutrophil cells (K/µl) | RBC (M/µl) | Hemoglobin (g/dL) | Platelets (K/µL) |
|---|---|---|---|---|---|
| PBS | 8.5 ± 1.5 | 1.1 ± 0.3 | 9.8 ± 0.5 | 15.0 ± 0.7 | 1330.0 ± 170.7 |
| BTZ 0.8 mg/kg | 5.6 ± 1.3* | 0.5 ± 0.4* | 9.2 ± 0.5 | 14.6 ± 0.6 | 1424.3 ± 146.2 |
| BTZ-PVA 0.8 mg/kg | 6.6 ± 2.1 | 0.8 ± 0.5 | 8.9 ± 0.4 | 14.1 ± 0.5 | 1598.3 ± 322.8 |
| BTZ-PVA 1.2 mg/kg | 6.5 ± 1.2 | 0.6 ± 0.3 | 8.7 ± 0.4 | 14.1 ± 0.6 | 1641.3 ± 160.5 |
| DOX 4 mg/kg | 5.8 ± 1.0* | 0.5 ± 0.2* | 8.3 ± 0.5* | 13.6 ± 0.9 | 1618.2 ± 190.5 |
| DOX-DCMs 4 mg/kg | 7.0 ± 2.1 | 1.0 ± 0.2 | 9.0 ± 0.5 | 14.5 ± 0.8 | 1305.6 ± 201.4 |
| BTZ 0.8 mg/kg + DOX 4 mg/kg | 5.5 ± 1.2* | 0.4 ± 0.2* | 8.1 ± 0.4* | 13.3 ± 0.5* | 1553.2 ± 161.5 |
| BTZ-PVA 0.8 mg/kg + DOX-DCM 4 mg/kg | 6.5 ± 1.6 | 0.6 ± 0.4 | 9.0 ± 0.5 | 14.2 ± 0.7 | 1463.6 ± 236.5 |

Note:
*$P < 0.05$, when compared to PBS control

TABLE 2

Serum chemistry (Hepatic and renal function panel) on day 7 after the last dosage in the therapeutic study

| Groups | ALT (U/L) | AST (U/L) | BUN (mg/dL) | Creatinine (mg/dL) | Total Bilirubin (mg/dL) |
|---|---|---|---|---|---|
| PBS | 26.0 ± 2.4 | 127.8 ± 32.7 | 17.6 ± 1.2 | 0.3 ± 0.0 | 0.1 ± 0.0 |
| BTZ 0.8 mg/kg | 28.3 ± 3.3 | 117.1 ± 26.4 | 16.3 ± 2.1 | 0.2 ± 0.1 | 0.1 ± 0.0 |
| BTZ-PVA 0.8 mg/kg | 24.5 ± 7.6 | 124.6 ± 25.5 | 15.4 ± 1.8 | 0.2 ± 0.0 | 0.1 ± 0.0 |
| BTZ-PVA 1.2 mg/kg | 33.6 ± 9.6 | 124.0 ± 29.6 | 15.1 ± 2.2 | 0.2 ± 0.0 | 0.1 ± 0.0 |
| DOX 4 mg/kg | 42.6 ± 8.6 | 167.7 ± 23.4 | 18.0 ± 2.6 | 0.2 ± 0.0 | 0.1 ± 0.0 |
| DOX-DCMs 4 mg/kg | 39.1 ± 6.8 | 156.0 ± 23.7 | 19.8 ± 4.0 | 0.2 ± 0.0 | 0.1 ± 0.0 |
| BTZ 0.8 mg/kg + DOX 4 mg/kg | 45.0 ± 7.7 | 157.4 ± 17.9 | 17.6 ± 3.4 | 0.2 ± 0.0 | 0.1 ± 0.0 |
| BTZ-PVA 0.8 mg/kg + DOX-DCM 4 mg/kg | 37.7 ± 7.6 | 130.6 ± 13.4 | 15.2 ± 1.9 | 0.2 ± 0.0 | 0.1 ± 0.0 |

Example 5

Catechol-Containing PVA Nanocarriers

Scheme 7 shows a schematic representation of loading of boronic acid containing drugs (e.g., bortezomib, BTZ) to PVA-catechol via boronate ester bonds formed between the boronic acid moiety of BTZ and the cis-diol groups of catechols.

Scheme 7

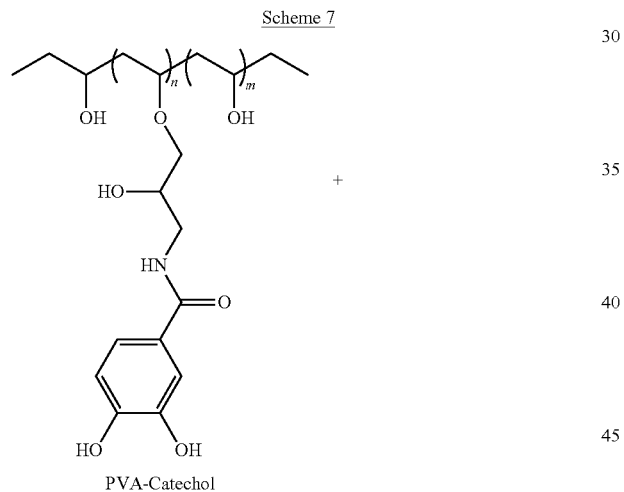

PVA-Catechol

+

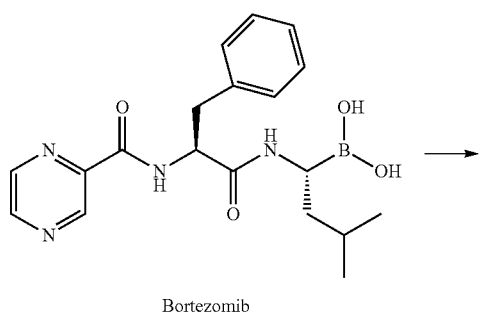

Bortezomib

-continued

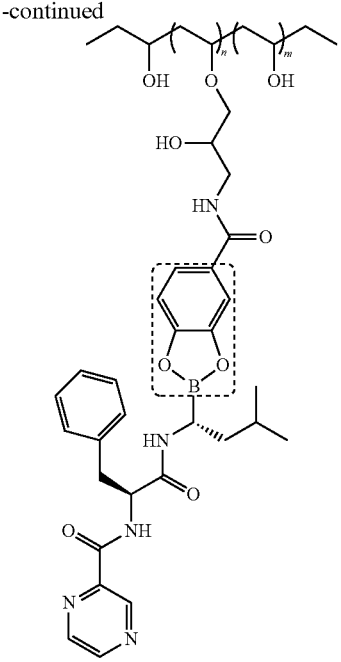

Figure 9:
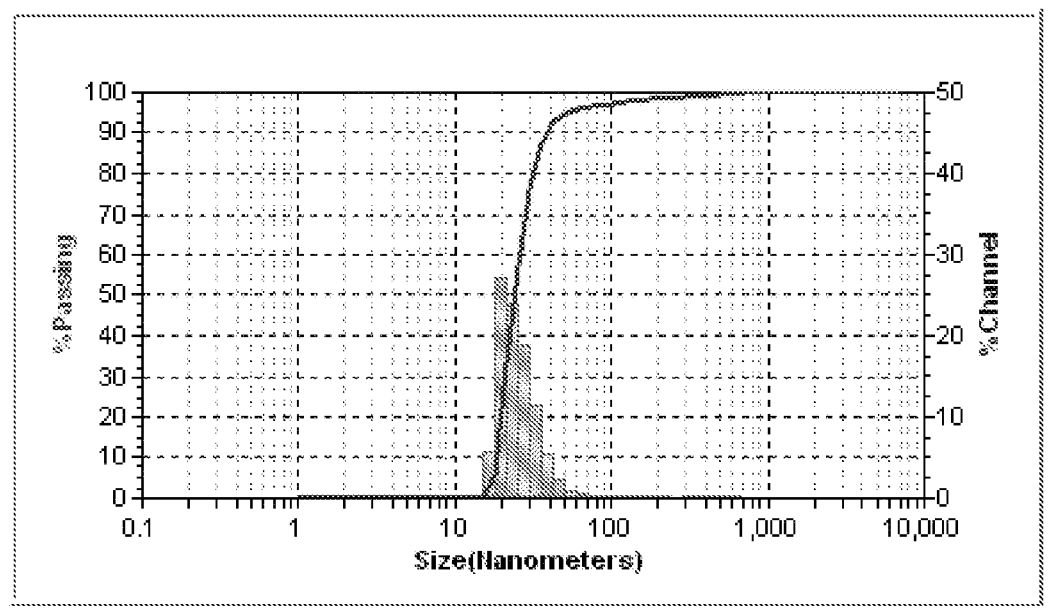
FIG. 9 shows the particle size of PVA-catechol nanoparticles loaded with bortezomib.

FIG. 9 shows the particle size of PVA-5% catechol-BTZ measured by DLS. drug loading level was 0.8 mg BTZ in 10 mg PVA-5% catechol polymer.

Preparation of Catechol-Containing PVA: Briefly, 100 ml of 2% polyvinyl alcohol solution (PVA,26 k Da) in dry DMSO was treated with NaH (0.05 eq., 2.3 mmol, 91 mg of NaH in mineral oil with 60% of purity) under $N_2$ atmosphere at room temp. with magnetic stirring for 2 hr. Excess epichlorohydrin (0.5 eq., 23 mmol, 2.1 g) was then introduced into the reaction and agitated overnight. Followed by the addition of 30 ml of ammonium hydroxide solution (concentration 28-30%). The reaction mixture was further stirred under nitrogen for 24 hr. 5 times volume of ethanol as added into DMSO solution to precipitate amino-PVA, the polymer was sufficintely washed with ethanol until the washing filtrate showed a negative result in the Kaiser test. Polymer was further washed with acetonitrile (3 times) and then dissolved in 20 mL of pure water and lyophilized. The polymer was then coupled with 3,4-dihydroxybenzoic acid to generate catechol-containing PVA.

Preparation of PVA-5% catechol-BTZ nanoparticles: Briefly, BTZ (0.8 mg) and PVA-Catechol (27 KDa 10 mg) were dissolved in DMSO under sonication and then dialyzed against PBS buffer for 3 hours. Unbound free BTZ was removed via column filtration with a 10 kDa molecular weight cutoff membrane.

Figure 10:
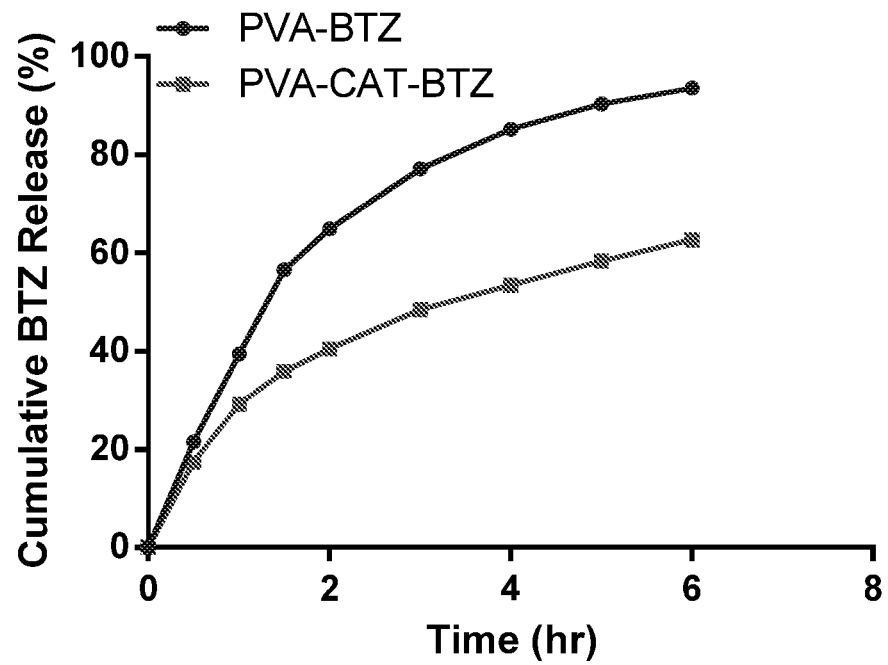
FIG. 10 shows cumulative drug release profiles for PVA nanoparticles and PVA-catechol nanoparticles loaded with bortezomib.
Figure 11:
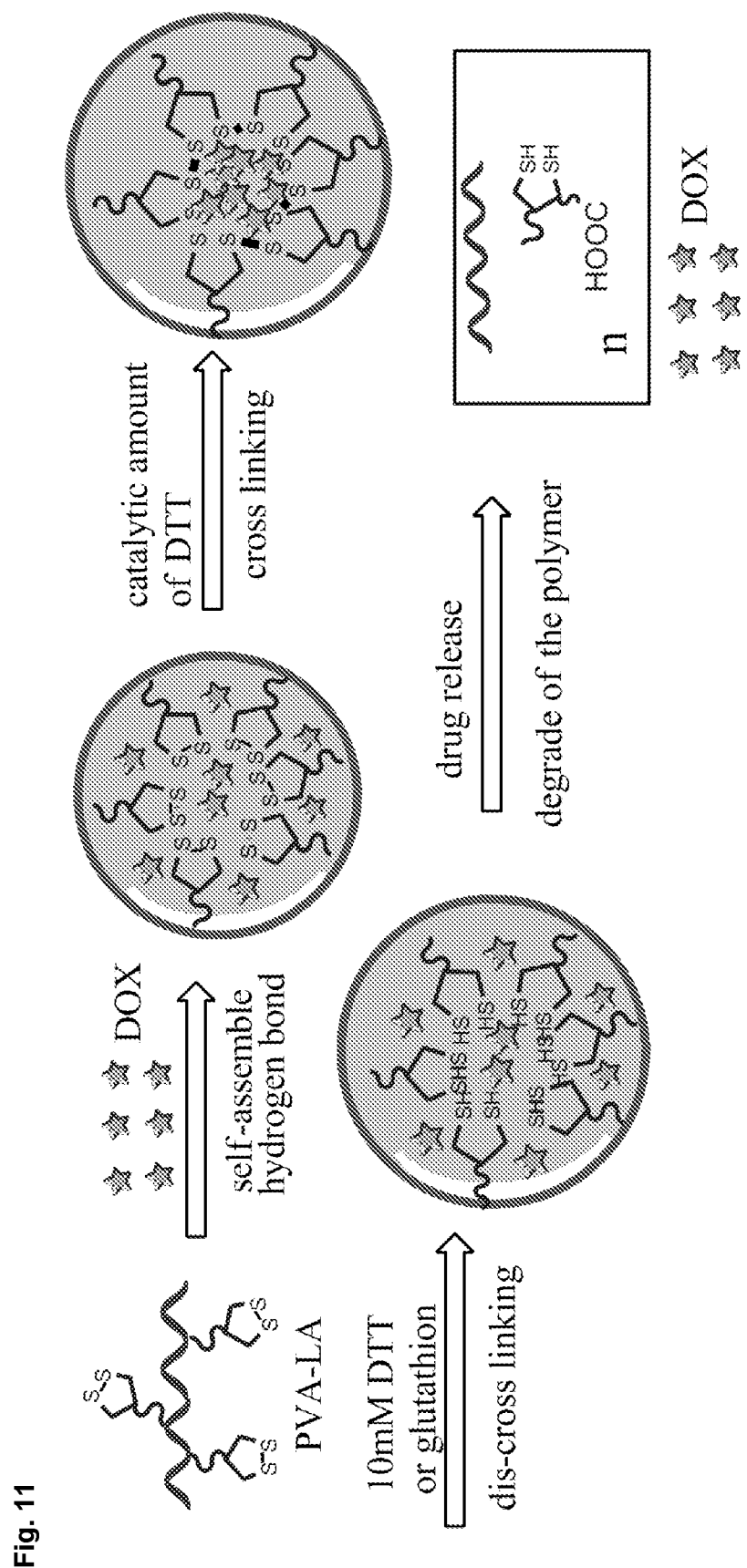
FIG. 11 shows a schematic illustration of DOX loaded in cross-linked PVA-lipoic acid (PVA-LA) nanoparticles.

FIG. 10 shows cumulative BTZ release profiles from PVA-BTZ and PVA-5% CAT-BTZ in PBS medium at pH 7.4. PVA-5% CAT-BIZ exhibited much slower drug release rate than PVA-BTZ.

Example 6

Lipoic Acid-Crosslinked Nanoparticles

Figure 7A:
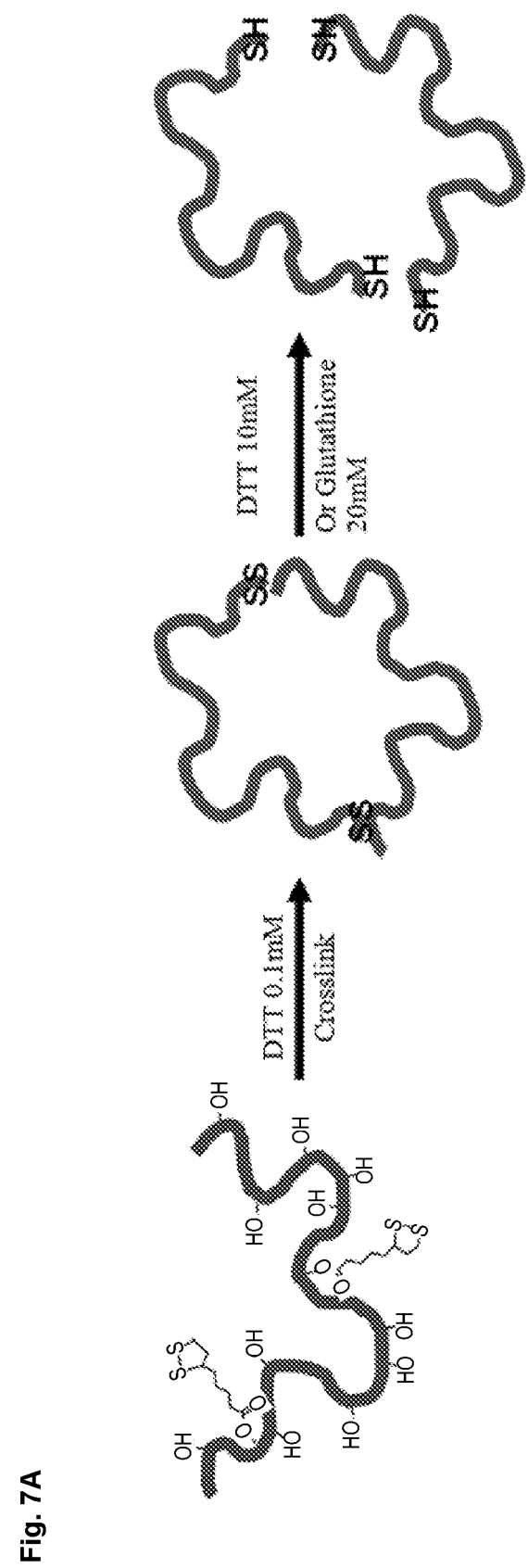
FIG. 7(A) shows a schematic representation of the lipoic acid-PVA derivative crosslinked by using dithiothreitol (DTT) by introducing 10 mol % DTT relative to the lipoyl units.
Figure 7B:
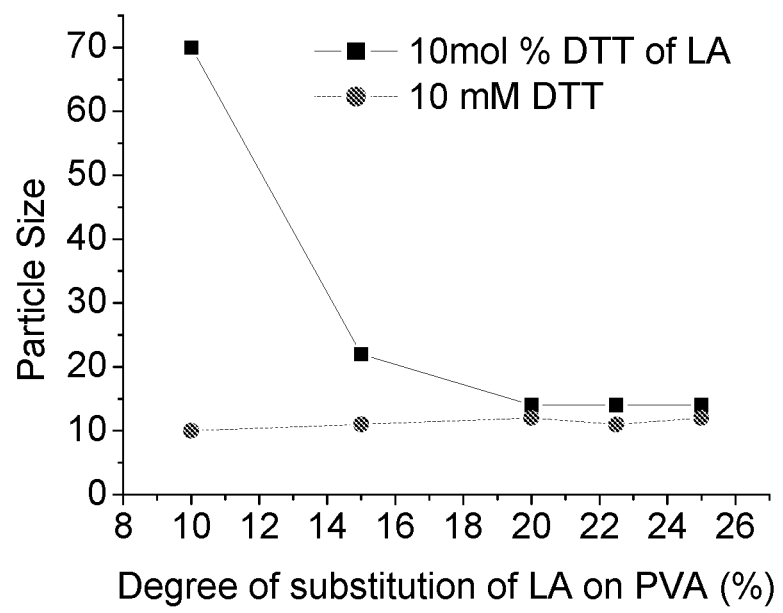
FIG. 7(B) shows the particle size of 27 KDa PVA with different levels of lipoic acid substitution in the presence of DTT.

FIG. 7(A) shows a schematic representation of a lipoic acid-PVA derivative crosslinked by introducing 10 mol % DTT relative to the lipoyl units. The cross-linking mechanism is based on thiol-disulfide exchange under catalysis by DTT, wherein lipoyl rings are opened to form preferentially linear disulfide bonds between different lipoyl units. FIG. 7(B) shows the particle size of the 27 KDa PVA with different ratios of lipoic acid substitutions in the presence of 10 mol % DTT relative to the lipoyl units and 10 mM DTT, respectively. The concentration of 27 KDa PVA was kept at 10 mg/mL.

Figure 8:
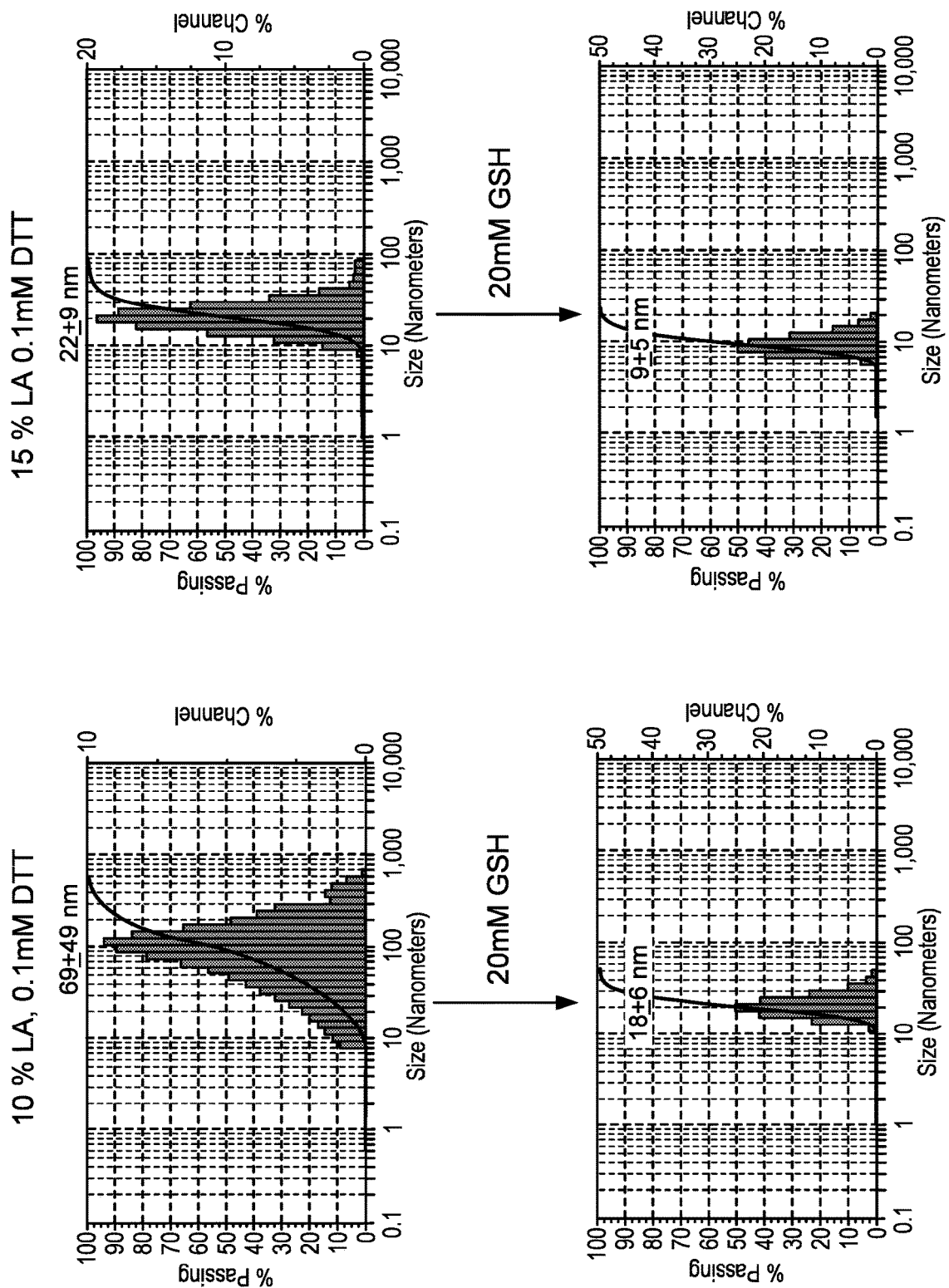
FIG. 8 shows the particle size of the lipoic acid-PVA derivative in the presence of DTT and glutathione (GSH).

FIG. 8 shows the particle size of the lipoic acid-PVA derivative in the presence of 10 mol % DTT relative to the lipoyl units (upper two panels) and de-crosslinked with 20 mM glutathione (GSH) (lower two panels).

Example 7

Core-Cross-Linked Nanocarriers Based on Poly(Vinyl Alcohol) Lipoic Acid Conjugates for Targeted Anticancer Drug Delivery Materials. Poly(vinyl alcohol)(PVA) (MW=27000) lipoic acid(LA), N-hydroxybenzotriazole (HOBt) Dithiothreitol (DTT), Diisopropyl carbodiimide (DIC), Dimethyl sulfoxide (DMSO), phosphate buffer saline solution(PBS) with 0.1 M and pH of 7.4 were purchased from Sigma-Aldrich (St. Louis, USA) and used without further purify. DOX was purchased from AK Scientific Inc. (Mountain View, Calif.). Cy5.5, a hydrophobic near infrared fluorescence dye was purchased from Invitrogen. Slide-A-Lyzer G2 Dialysis Cassettes (MWCO 3500) purchased from Thermo Fisher Scientific Inc., (Rockford, USA).

Synthesis of PVA-LA/Cy5.5 labeled PVA-LA Conjugates. The PVA-LA conjugates were synthesized via esterification. In a typical example, a solution of lipoic acid (0.469 g) in DMSO was added dropwise into a solution of PVA(1.0 g) in 50 mL DMSO using HOBT and DIC as coupling reagent under a nitrogen atmosphere. The reaction proceeds under magnetic stirring for 48 hr at room temperature in dark. The production was isolated by precipitation in cold ethanol, washed several times with ethanol. The product was subsequently dialyzed and lyophilized to yield a white powder. To monitor the real-time biodistribution of PVA-LA NPs. Cy5.5 was introduced into PVA-LA using the same method described as above and followed by dialysis to remove free Cy5.5 dye.

Preparation and characterization of DOX loaded N-PVA-LA, Pre-PVA-LA and Cr-PVA-LA NPs. For DOX loaded non-cross-linked PVA-LA (N-PVA-LA) NPs, DOX and no cross-linked PVA-LA were first dissolved in DMSO, then dropwise add additional of distilled water to a DMSO solution of DOX and PVA-LA, stirring for 2 hr at room temperature and followed by dialysis against PBS for 8 hr. For DOX loaded pre-cross-linked PVA-LA (N-PVA-LA) NPs, N-PVA-LA were dissolved in DMSO firstly and then the solution was adjusted to pH 8.5 using borate buffer. The dispersion was purged with $N_2$ and added 10% DTT relative to the amount of lipoyl units. The reaction proceeds under magnetic stirring for 22 hr at room temperature in dark. Then DOX were added into pre-PVA-LA solution, stirring for 2 hr and dropwise add additional of distilled water and followed by dialysis against PBS for 8 hr. To form DOX loaded cross-linked PVA-LA (Cr-PVA-LA) NPs, DOX was loaded and cross linked with the similar strategy except DOX and N-PVA-LA were dissolved together at the beginning.

The size and size distribution of the NPs were measured by dynamic light scattering(DLS) instruments (Nanotrac). The morphology of NPs was observed on a Philips CM-120 transmission electron microscope (TEM) operating at an acceleration voltage of 80 kV. The sample was prepared as literature.

Drug release study. DOX-loaded Cr-PVA-LA NPs solution was prepared to determine the in vitro drug release profile. The initial DOX concentration was 1.0 mg/mL, Aliquots of the DOX-loaded Cr-PVA-LA NPs solution were injected into dialysis cartridges with 3.5 kDa MWCO. The cartridges were dialyzed against 100 volume times PBS solution at 37° C. and rotator rate was set to 100 rpm. The concentration of DOX remained in the dialysis cartridge at various time points was determined using absorbance measurement by dilute the dialysis solution 10 times in DMSO. Values were reported as the means for each triplicate samples.

In vitro cytotoxicity study. The cytotoxicity of blank Cr-PVA-LA NPs was evaluated on MDA-MB-231 and MCF-7 cells. The in vitro anti-tumor effects of DOX loaded Cr-PVA-LA NPs were evaluated on MDA-MB-231 cell in comparison with the commercial DOX. MDA-MB-231 and MCF-7 cells were seeded in 96-well plates a day prior to the treatment at a density of 3000 cell/well. After 72 hr incubation with different concentrations of blank Cr-PVA-LA or DOX loaded Cr-PVA-LA NPs in a humidified 37° C., MTT was added to each well and further incubated for 2 hr. The absorbance at 486 nm was detected using a microplate ELISA reader(SpectraMax M2, Molecular Devices, USA). Values were reported as the means for each triplicate samples.

Intracellular Release of DOX. The cellular uptake and intracellular release behaviors of DOX-loaded core-cross-linked PVA-LA NPs were followed with confocal laser scanning microscopy (CLSM) using CMB-231 cells. The cells were cultured on microscope slides in a six-well plate using. The cells were incubated with DOX-loaded micelles for 6 hr at 37° C. in a humidified 5% CO2-containing atmosphere. The culture medium was removed and the cells were rinsed three times with PBS. The cell nuclei were stained with 4',6-diamidino-2-phenylindole (DAPI). The fluorescence images were obtained using a confocal microscope.

In vivo and ex vivo optical imaging. MDA-MB-231 breast cancer cells ($7 \times 10^6$ cells in a total volume of 100 μL PBS and Matrigel, 1:1 v/v) were injected subcutaneously into nude mice to form subcutaneous nodules. The MDA-MB-231 tumor bearing mouse was injected via tail vein with 100 μL of Cy5.5 labeled PVA-LA NPs solution (the concentrations is 1? tug/mL). The final size of the micelles was 9 nm. In vivo near infrared (NIRF) optical imaging of the mice was obtained by a Kodak Image Station 2000MM at different time points. The mouse was sacrificed at 72 h post-injection and all the major organs and tumor were excised for ex vivo imaging. All animal experiments were performed in compliance with institutional guidelines and according to protocol No. 06-12262 approved by the Animal Use and Care Administrative Advisory Committee at the University of California, Davis.

In vivo therapeutic study. Subcutaneous MDA-MB-231 breast cancer xenografts were implanted into nude mice as described above. The treatments were started when tumor xenograft reached a tumor volume of 100-200 mm³ and this day was designed as day 0. On day 0, these mice were randomly divided into three groups, with five mice in each group. PBS, DOX (5 mg/kg), and DOX loaded PVA-LA NPs (5 ma/kg) respectively was administered intravenously into the tail vein on every four day for total 6 doses. Tumor volume was calculated by the formula $(L \times W^2)/2$, where L is the longest and W is the shortest in tumor diameters(mm).

Fabrication and characterization of PVA-LA NPs. A PVA-LA conjugate was designed and synthesized via an esterification reaction, and the synthetic procedure for preparation of PVA-LA is shown in Scheme 8. The characteristic structural feature of lipoic acid is the presence of a constrained 1,2-dithiolane ring that is thermodynamically unstable and possesses a high tendency to thiol-disulfide exchange and self-polymerization.

Figure 14:
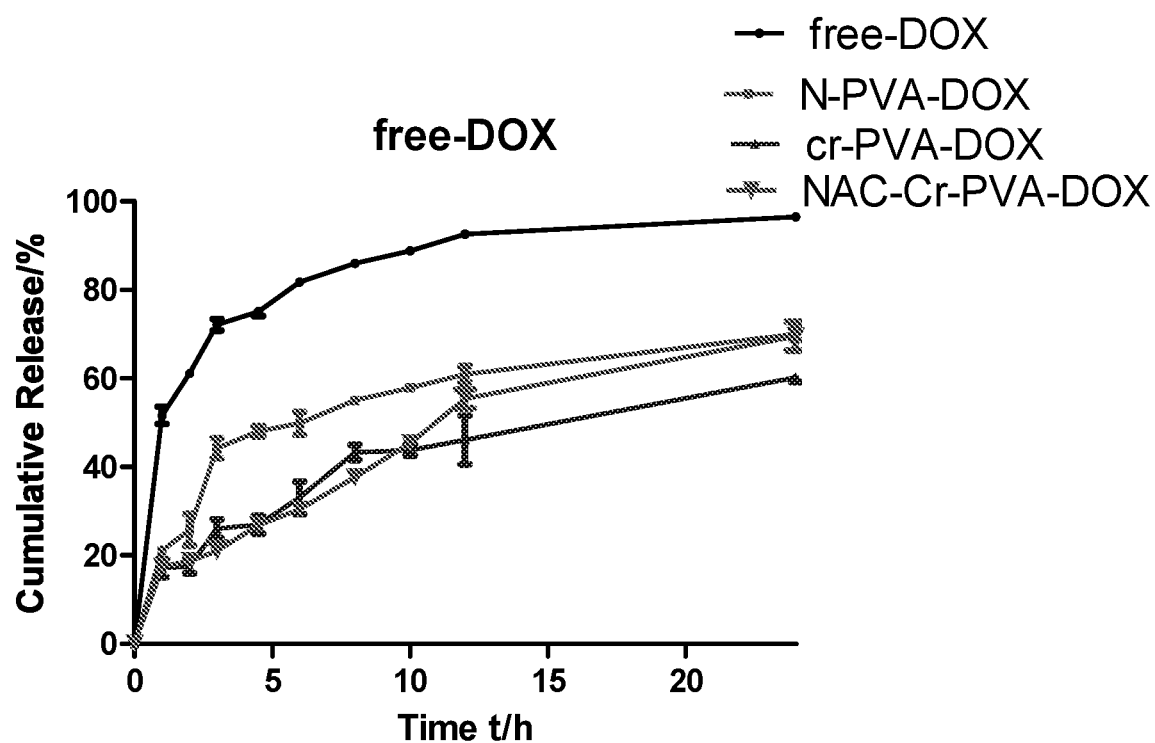
FIG. 14 shows the release profiles of DOX loaded in N-PVA-LA(red), cr-PVA-LA(blue) and treated with NAC (green) in PBS and compared to free-DOX(blue). The concentration of DOX remained in dialysis cartridges at various time points was measured by absorbance measurement.

Loading and Triggered Release of DOX. DOX, the most potent anticancer drugs used widely in the treatment of various malignant tumors, was used as a model to study the trigged drug release behavior of the PVA-LA NPs. The accumulated release results shown in FIG. 14 represent the total amount of DOX released from different sample. The free DOX displayed a burst release. More than 50% of DOX were release within 1 h. However, the release of DOX from PVA-LA NPs was largely inhibited, in which only about 60.0% and 70.0% drug was released in 24 hr from cross-linked and no cross-linked PVA-LA NPs, respectively. In the presence of 20 mM NAC, a reductive condition analogous to that of the intracellular compartments, drug release of DOX-loaded cr-PVA-LA can be enhanced to the same level of N-PVA-LA. It should be further noted that no burst release was observed even in the presence of NAC. The unique core-shell structure contributes to the constant release rate. This biodegradable PVA-LA NPs is a highly promising approach to controlled drug release.

Figure 15A:
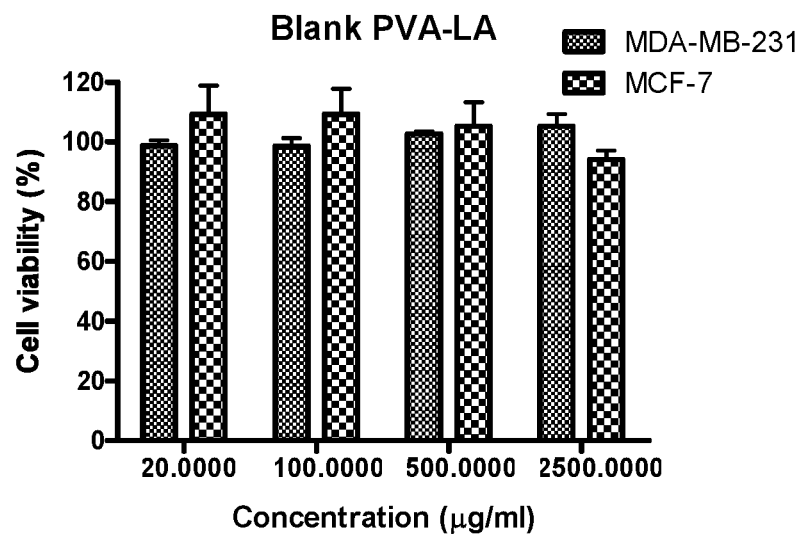
FIG. 15(A) shows the cytotoxicity of unloaded ("blank") PVA-LA to MDA-MB-231 cells and MCF-7 cells.

In vitro cytotoxicity study. Blank PVA-LA NPs were evaluated for their cytotoxicity against MDA-MB-231 cells and MCF-7 cells with an MTT assay. As shown in FIG. 15(A), the PVA-LA NPs were practically nontoxic to MDA- Scheme 8

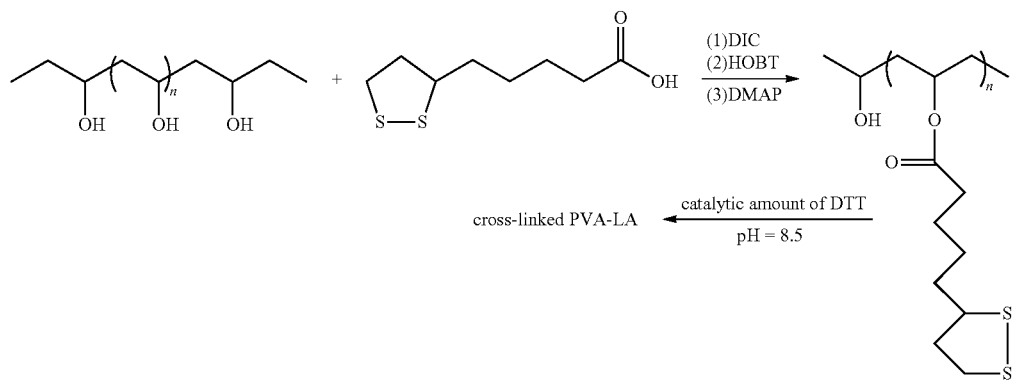

Figure 12:
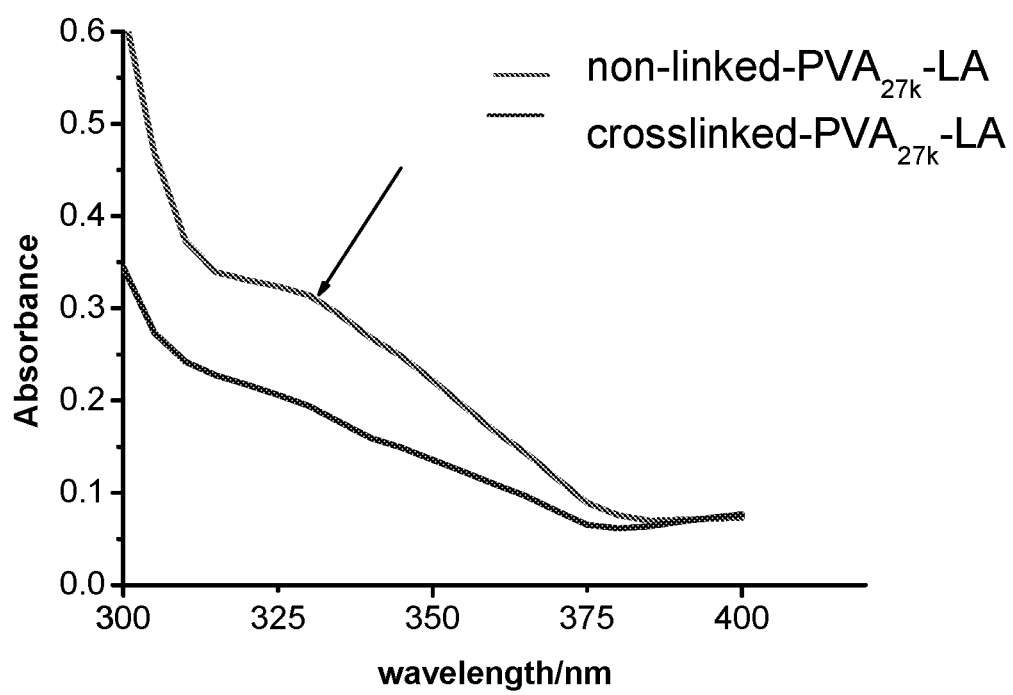
FIG. 12 shows UV spectral changes of non-crosslinked PVA-LA and crosslinked PVA-LA in DMSO.

The cross-linking of PVA-LA conjugate was carried out via a disulfide bond exchange reaction wherein lipoyl rings are opened at the S—S bond in the presence of catalytic amount of DTT and form preferentially linear disulfide between different lipoyl units, as reported previously. The structure change of the cross-linked PVA-LA in DMSO was determined by the ultraviolet(UV) spectra. As shown in FIG. 12, the characteristic absorption of the ring disulfide bond at 330 nm disappeared, which means the PVA-LA NPs have been crosslinked by sulfide bond exchange.

Figure 13A:
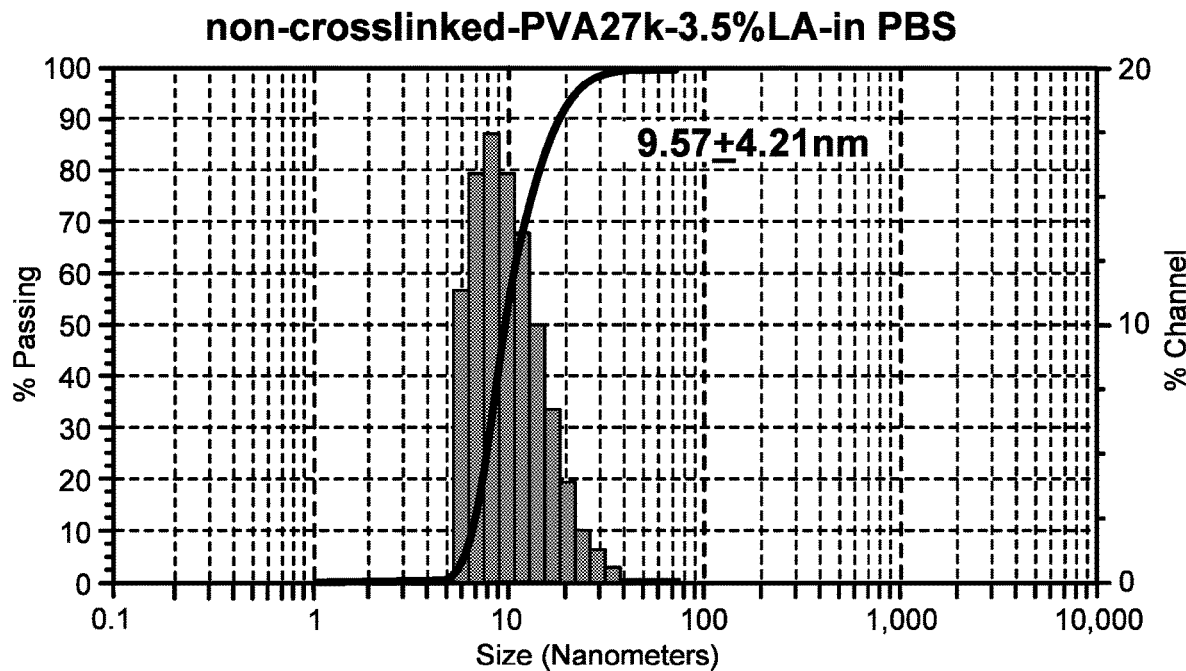
FIG. 13(A) shows the size of as-prepared PVA-LA NPs.
Figure 13B:
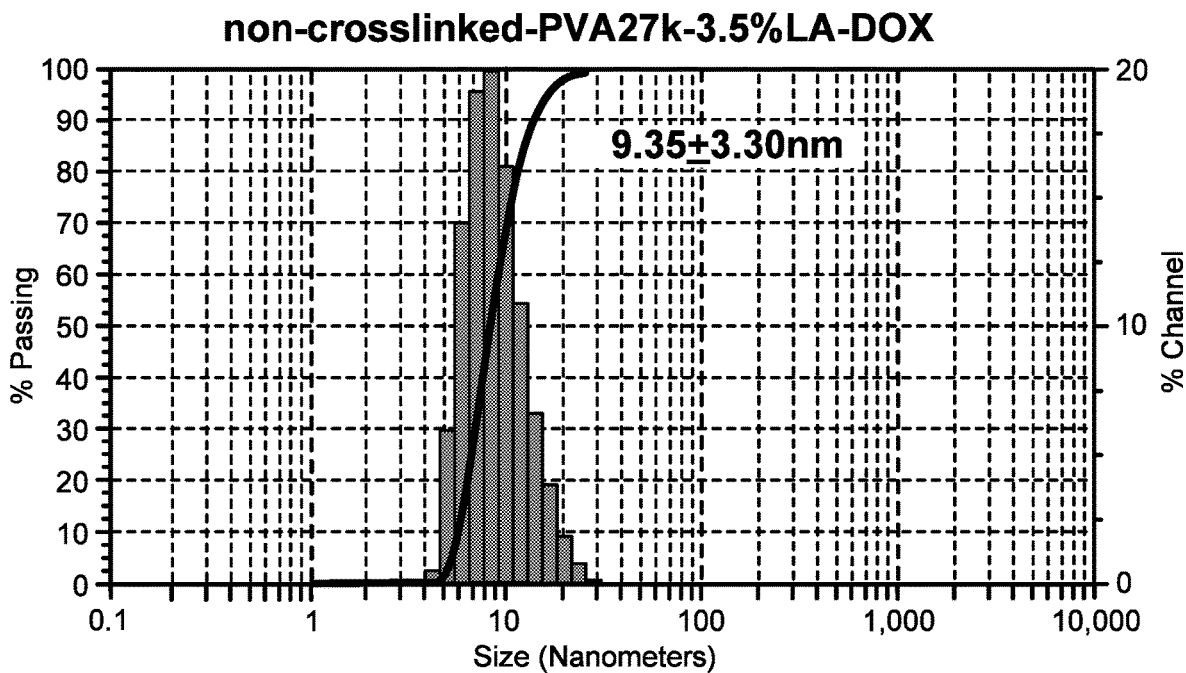
FIG. 13(B) shows the size of DOX loaded non-crosslinked PVA-LA NPs.

The size and size distribution of NPs is a very important parameter for intracellular drug delivery and maintain effective EPR effect for passive tumor-targeting. The size of PVA-LA NPs was determined by DLS measurement. As shown in FIG. 13, the size of PVA-LA NPs is about 9.57 nm and show a very narrow size distribution. After loading DOX, compared with no drug loading polymers, the size of DOX loaded non-PVA27-LA NPs shows a very little shrink from 9.57 nm to 9.35 nm while DOX loaded both the pre-crosslinked and crosslinked-PVA-LA NPs shows a very distinct shrink from 9.57 nm to 8.30 nm and 7.90 nm respectively, which means the conjugate mainly occurs intramolecularly. Both crosslinking and drug loading will affect the size of polymers.

MB-231 cells and MCF-7 cells at concentrations up to 2.5 mg/mL, indicating that PVA-LA NPs possess excellent biocompatibility. As a matter of fact, PVA are one of the few synthetic water-soluble polymers approved for used in drug carriers by U.S. Food and Drug Administration (FDA), while lipoic acid is produced naturally in the human body and commonly used as an antioxidant drug for treating diseases such as diabetes and HIV. Thus, these nanoparticles are based solely on well-accepted medical materials.

Figure 15B:
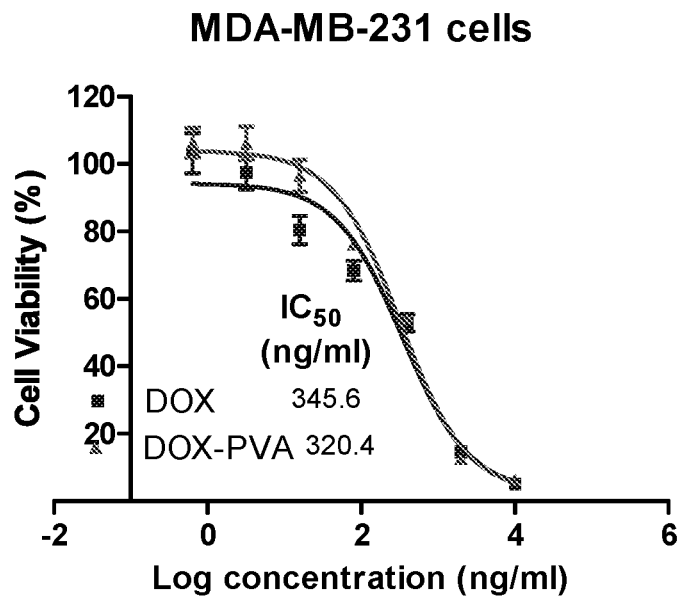
FIG. 15(B) shows the anticancer effects of DOX-loaded PVA-LA NPs compared with free DOX. MDA-MB-231 cells were treated with different DOX doses from $0.64 \times 10^{-3}$ to 0.1 mg mL$^{-1}$.

The ability of DOX-loaded PVA-LA NPs to inhibit proliferation of MDA-MB-231 cells was investigated using an MTT viability assay, and it was compared with DOX in free form. As shown in FIG. 15(B), similar dose-response curves were observed. The IC50 values of DOX-PVA-LA and free DOX were 320.4 mg/mL and 345.6 ng/mL, respectively, which indicated DOX-PVA-LA exhibited equivalent cytotoxic activity in vitro.

Figure 16A:
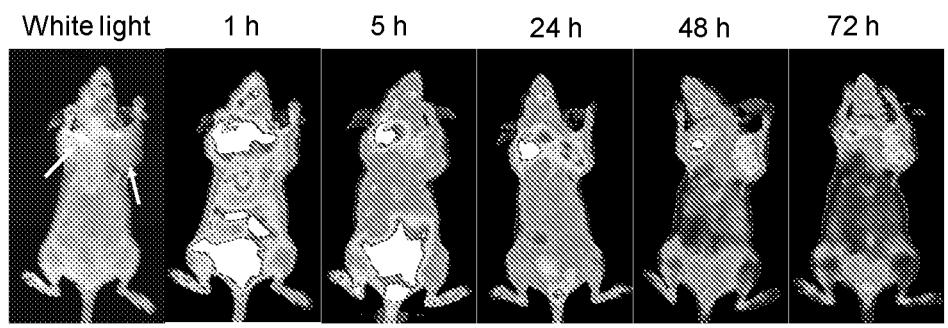
FIG. 16(A) shows in vivo NIRF optical images of orthotopic MDA-MB-231 breast cancer xenograft mouse injected intravenously with Cy5.5-loaded PVA27k-LA.
Figure 16B:
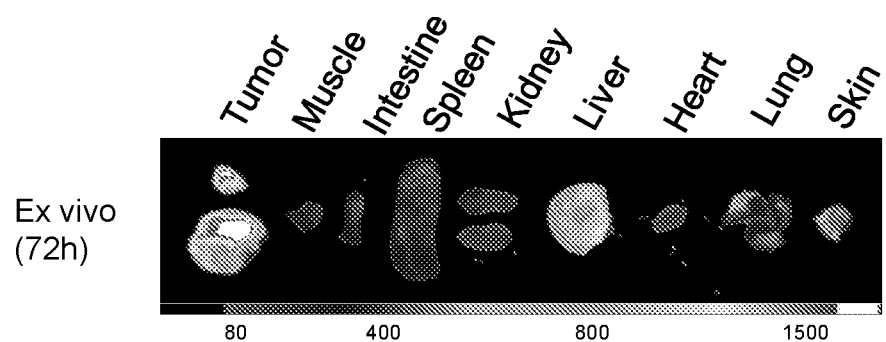
FIG. 16(B) shows ex vivo NIRF optical images of orthotopic MDA-MB-231 breast cancer xenograft mouse injected intravenously with Cy5,5-loaded PVA27k-LA. Tumors and major organs were excised for ex vivo imaging at 72 hours post-injection.

In vivo biodistribution of PVA-LA NPs in tumor bearing mice. Near infrared(NIR) fluorescent dyes enable deep tissue imaging with high penetration, low tissue absorption and scattering. Hereby, hydrophobic NIRF dyes Cy5.5, a hydrophobic near infrared were conjugated to PVA-LA NPs and utilized Noninvasive NIR fluorescence optical imaging technology to monitor the real-time distribution, excretion, and tumor targeting efficiency of Cy5.5 labeled PVA-LA NPs in mouse bearing orthotopic MDA-MB-231 breast cancer xenograft. As shown in FIG. 16, the substantial contrast between subcutaneous tumor and normal tissue was observed from the beginning and a significantly higher fluorescence signal in tumor site maintained up to 72 hr. This result demonstrated that PVA-LA NP could preferentially accumulate in tumors site compared to normal tissue, which were further confirmed by ex vivo results shown in bottom of FIG. 17. At 72 hr post injection, tumors and major organs were excised for ex vivo MIRE imaging to determine PVA-LA NPs tissue distribution. The highest fluorescence signal was observed in tumor tissue. Besides, there is a relative higher fluorescence signal in the liver tissue than other organ, which means PVA-LA NPs eliminated predominately via the liver. The prolonged circulation and enhanced permeability and retention(EPR) effects likely contributed to this results.

Figure 17A:
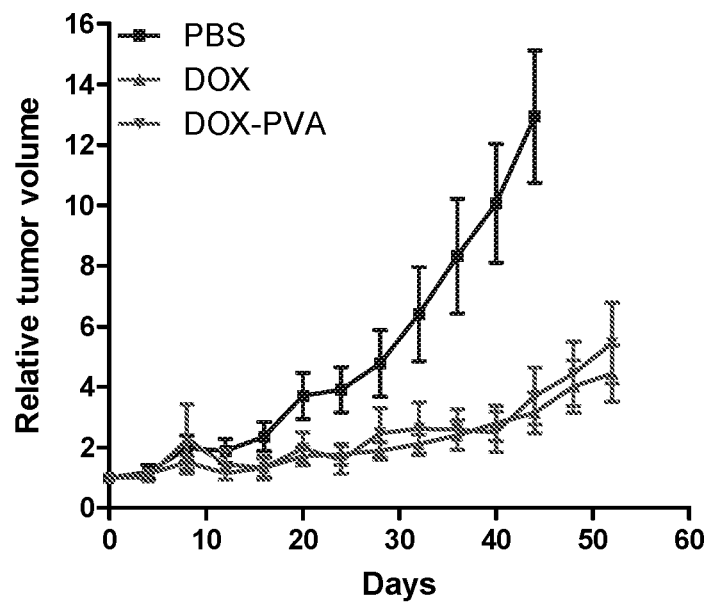
FIG. 17(A) shows in vivo anti-tumor efficacy in MDA-MB-231 tumor bearing mice (n=5-8) after intravenous treatment of PBS, DOX (5 mg/kg), and DOX-PVA (5 mg/kg) respectively, every four day for total 6 doses. Data represent mean±SEM of five mice per group.
Figure 17B:
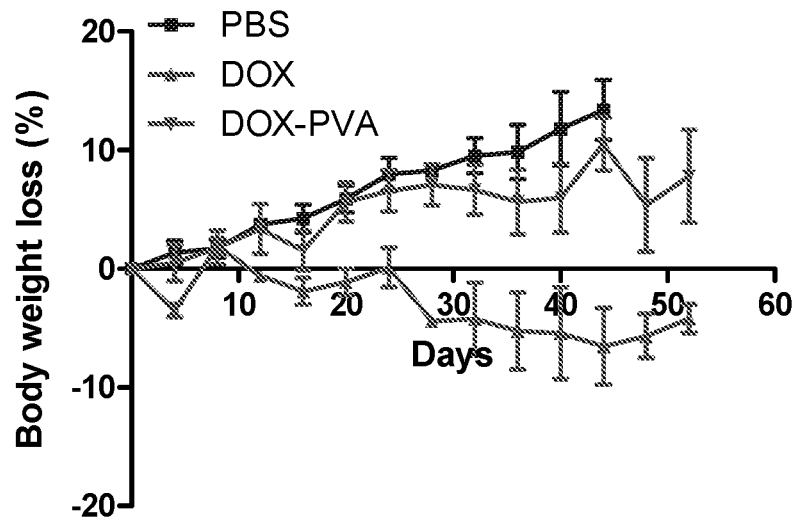
FIG. 17(B) shows body weight changes in MDA-MB-231 tumor bearing mice (n=5-8) after intravenous treatment of PBS. DOX (5 mg/kg), and DOX-PVA (5 mg/kg), every four day for total 6 doses. Data represent mean±SEM of five mice per group.

Anti-tumor efficacy in breast cancer xenograft mouse mode The anti-tumor effects of DOX-PVA-LA NPs after intravenous injection were evaluated in subcutaneous MDA-MB-231 tumor bearing mice. The mice were intravenously administrated with PBS, DOX (5 mg/kg), and DOX-PVA (5 mg/kg) respectively, every four day for total 6 doses. As shown in FIG. 17, treatment with either the DOX group or the DOX-PVA-LA NPs group showed significant anti-tumor activity as compared with the PBS control group. While no noticeable weight loss in treat group was observed in DOX-PVA-LA NPs treated group. The lower toxicity of DOX-PVA-LA NPs over MDA-MB-231 tumor bearing mice should be attributed to their preferential accumulation at tumor site and sustained drug release profile.

Conclusions. In summary, water-soluble and biodegradable PVA-LA conjugate NPs with core-shell structure was successfully developed, which can readily for loading hydrophobic drugs such as DOX and can be trigged release in reductive environment. The DOX loaded PVA-LA NPs showed significant anti-tumor activity and lower toxicity when compared to DOX alone. The PVA-LA NPs is a promising drug delivery system for hydrophobic drugs in the treatment of cancer.

Example 8

Synthesis of PVA-Porphyrin Conjugates

The present invention provides a new generation of poly(vinyl alcohol)(PVA)-porphyrin-based nanoparticles (PPNs) using a simple and cost-effective "one-pot" fabrication approach. By incorporation of drugs and imaging agents in the self-assembly procedure of PVA-porphyrin conjugates, the invention provides PPNs with a micelle-like structure and an integration of multiple imaging and therapy modalities including near-infrared (NIR) optical imaging, MR imaging, PET imaging, chemotherapy, photodynamic therapy (PDT) and photothermal therapy (PTT). The PVA-based nanoparticles are therefore useful in an exceptionally broad range of applications. As the building blocks, PVA and pyropheophorbide are both biocompatible, and the PPNs showed no apparent cytotoxicity up to 400 mg/kg in animal models. This highly biocompatible PVA-porphyrin-based nanoplatform can be used for multimodal imaging, combination therapy, and imaging-guided cancer therapies.

Synthesis of PVA-porphyrin conjugates: The PVA-porphyrin conjugates were synthesized via esterification. In a typical example, a solution of lipoic acid (1%, 5%, 10% or 15% molar ratio to the hydroxyl groups on PVA) in DMSO was added dropwise into a solution of PVA (1.0 g) in 50 mL DMSO using HOBT and DIC as coupling reagents under a nitrogen atmosphere. The reaction proceeds under magnetic stirring for 48 hr at room temperature in dark. The production was isolated by precipitation in cold ethanol and washed several times with ethanol. The product was subsequently dialyzed and lyophilized to yield a dark green powder.

Figure 18A:
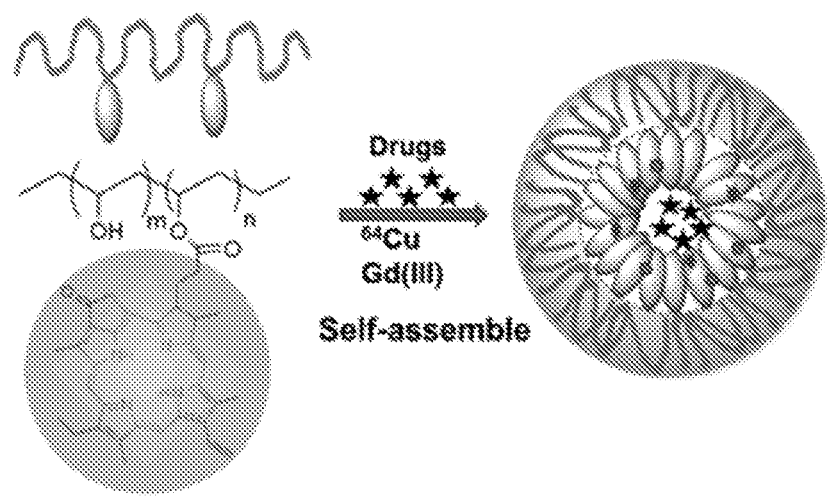
FIG. 18(A) shows a schematic representation of PVA-pheophorbide nanoparticles. The PVA-pheophorbide conjugates can self-assemble into nanoparticles in aqueous solution.
Figure 18B:
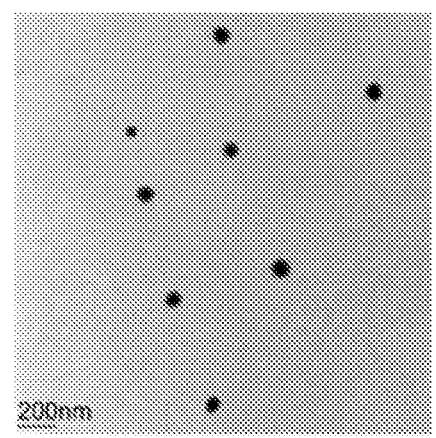
FIG. 18(B) shows a TEM image of PPNs stained with phosphotungstic acid.
Figure 18C:
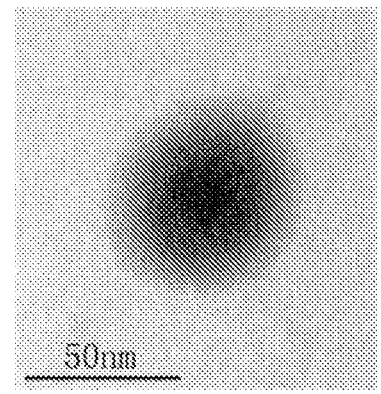
FIG. 18(C) shows a TEM image of a PPN stained with phosphotungstic acid.
Figure 18D:
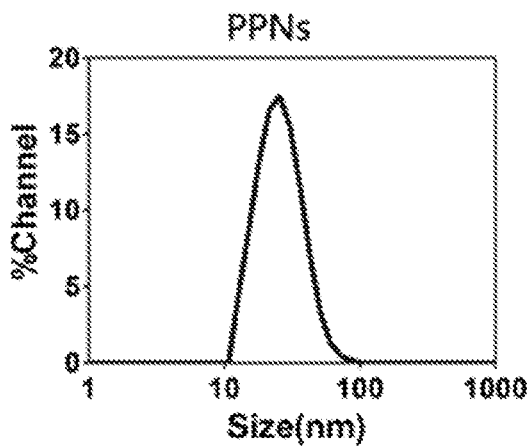
FIG. 18(D) shows the dynamic light scattering size distribution of PPNs in PBS.
Figure 18E:
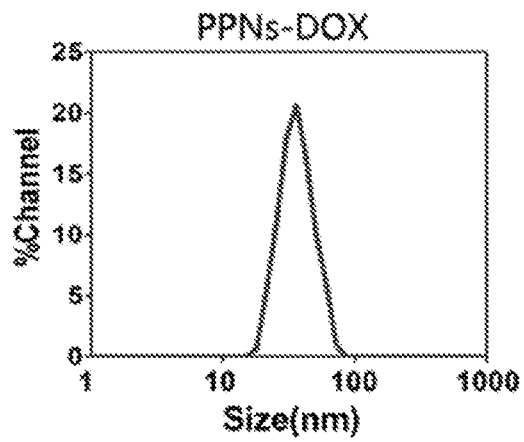
FIG. 18(E) shows the dynamic light scattering size distribution of DOX-loaded PPNs in PBS.
Figure 18F:
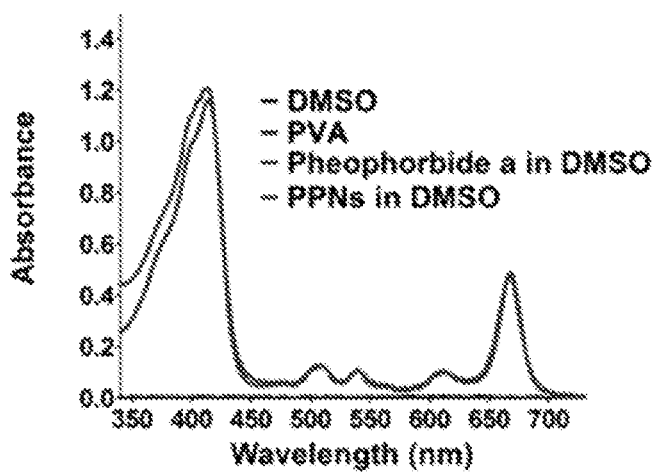
FIG. 18(F) shows absorption spectra of PVA (blue), pheophorbide a, (red) and pheophorbide a-conjugated PVA (green) in DMSO.
Figure 18G:
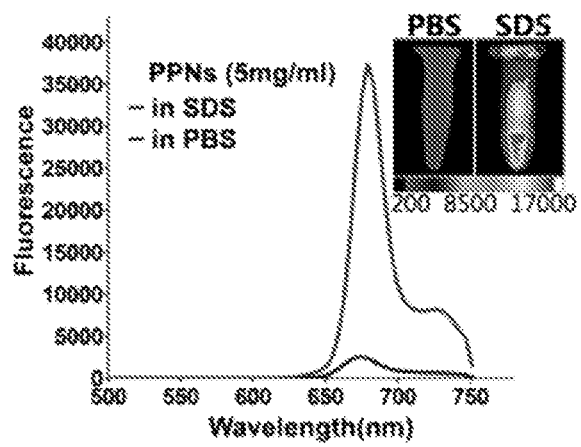
FIG. 18(G) shows the fluorescence emission of PPNs in PBS (blue) versus in the dissociated state in SDS (red), as well as near-infrared imaging of PPN solutions in PBS and SDS, respectively.

FIG. 18a schematically illustrates the chemical structures of PVA-porphyrin conjugates, and how they can be used as multifunctional nanoparticles. Pyropheophorbide, a chlorophyll derived porphyrin analogue (Chen, K. et al., *J. Photochem. Photobiol. B.*, 96 (1) 66-74 (2009)) was conjugated to the hydroxyl group of PVA via one-step ester formation. $^1$H NMR spectrometry was performed to determine the chemical structures of PVA and porphyrin-conjugated PVA (FIG. 30). The PVA-porphyrin conjugates (PVA-Por) can self-assemble to form PPNs in aqueous environments with a hydrophobic porphyrin core surrounded by the PVA chains (FIG. 18a). The morphology of PPNs was observed under a transmission electron microscope (TEM). As shown in FIG. 18b, PPNs in PBS exhibited spherical shapes and relatively uniform size distribution. At higher magnifications, a typical core-shell structure of PPNs was evident (FIG. 18c). The particle size was determined by dynamic light scattering (DLS). The results showed that mean size of PPNs in PBS was 21 nm in diameter, which was consistent with that observed by TEM (FIG. 18d). The PVA-Por exhibited two main absorption peaks, one at 405 nm and one in the near-infrared window at 670 nm (FIG. 18f). When excited at 625 nm, the PVA-Por formulated in PBS showed very weak fluorescence with a peak at around 680 nm. In contrast, when using sodium dodecyl sulfate (SDS) to disrupt the PPNs, much stronger fluorescence at around 680 nm was detected. Further, NIR fluorescence imaging also demonstrated tremendously higher fluorescence after dissociation of PPNs with the addition of SDS (FIG. 18g).

Example 9

Preparation and Characterization of Doxorubicin-Loaded PVA Porphyrin Nanoparticles DOX was loaded into PVA-porphyrin nanoparticles (PPNs) by dialysis of a polymer/DOX solution in DMSO against PBS buffer. DOX and PVA-porphyrin (1 mg:20 mg) was firstly dissolved in DMSO, and then the solution was adjusted to pH 8.5 with borate buffer, followed by dialysis against PBS buffer for 3 hours. Free DOX was removed via column filtration with a 10 kDa molecular weight cutoff membrane. The amount of DOX was determined using absorbance measurement by diluting PPNs-DOX solution 10 times in DMSO. The calibration curve was obtained using a series of DOX/DMSO standard solutions with different concentrations. The morphology and particle size distribution of PPNs-DOX nanoparticles were characterized by transmission electron microscopy (TEM) and dynamic light scattering (DLS), respectively. In vitro drug release profiles were carried out using the dialysis method. Aliquots of DOX-loaded PPNs solution were injected into a dialysis cartridge with a molecular weight cutoff of 3.5 kDa. The whole dialysis process was carried out at 37° C. with swirling at 70 rpm in the presence of 10 g/L activated charcoal in 1 L PBS buffer. The concentration of DOX remained in the dialysis cartridge at various time points was determined by absorbance measurement.

Figure 18H:
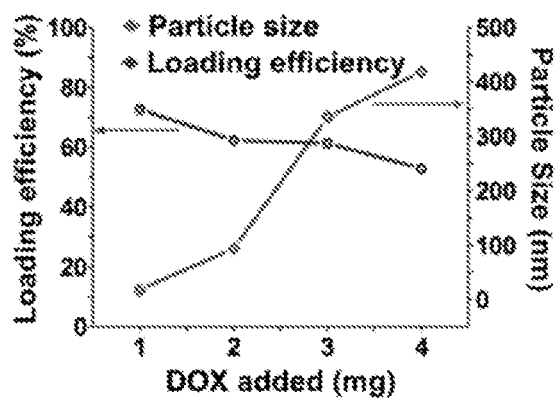
FIG. 18(H) shows the DOX loading efficiency of PPNs and the particle size change of PPNs-DOX versus the level of drug added at initial loading.
Figure 18I:
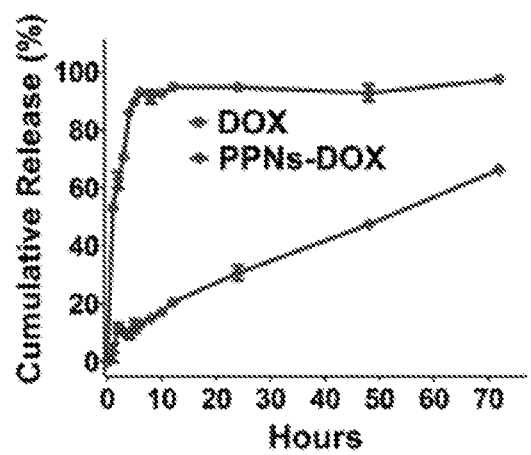
FIG. 18(I) shows the cumulative DOX release profiles from free DOX and DOX-loaded PPNs.

Besides their unique photonic properties, the PPNs could efficiently encapsulate hydrophobic drug, doxorubicin (DOX), during the nanoparticle formation by the self-assembly of PVA-Por. The loading efficiency (LE) for DOX approached 75% when the ratio of DOX to PPNs was 5% (w/w). However, the LE decreased to 62% and 53%, when the initial amount of DOX increased to 10% and 20%, respectively. The particle size ranged from 25 to 34 nm when the initial amount was 5%, which was slightly increased compared to the PPNs alone without payload. With increasing amount of DOX loading, the particles size increased gradually and the particle size distribution was broadened (FIG. 18h). TEM image showed that DOX-loaded PPNs are spherical in shape with an average diameter of 40 nm, which was close to that measured by DLS (FIG. 18e). The release profile of DOX from DOX-loaded PPNs was studied using a dialysis method. As shown in FIG. 18i, free DOX was rapidly diffused out of the dialysis cartridge and 90% of free DOX was released within the first 5 hrs. In contrast, DOX-loaded PPNs sustained DOX release into surrounding PBS, with initial release of 11% of DOX during the first 5 hrs according to our data. After that, DOX-loaded PPNs showed a slow linear release profile and released 66% of drug in 72 hrs. The stability of DOX-loaded PPNs was also evaluated. Both the particle size and drug content showed no significant changes over 3 months at 4° C. in PBS.

Example 10

Cellular Uptake of PVA-Porphyrin Nanoparticles and In Vitro Cytotoxicity Studies The uptake profiles of DOX-loaded PPNs in SKOV-3 ovarian cancer cells were qualitatively observed by confocal microscopy. SKOV-3 cells were seeded in an 8-well slide. When the cells were 80%~90% confluent, cells were incubated with free DOX and PPNs-DOX (final concentration of DOX=0.05 mg/ml) for 30 min and 6 hrs at 37° C. with 5% $CO_2$, respectively. Then the cells were washed thrice with PBS buffer, fixed with 4% paraformaldehyde for 15 min. The nuclei were stained with DAPI. The slides were mounted with coverslips and observed by confocal microscopy.

An MTS assay was carried out to evaluate the in vitro cytotoxicity of free DOX, blank/DOX-loaded PPNs against ovarian cancer cells. SKOV-3 cells were seeded in 96-well plates at the cell densities of $0.5\times10^4$ cells/well, respectively. After 24 hrs incubation, cells were treated with different concentrations of free DOX, PPNs-DOX, and equivalent doses of blank PPNs. At 72 hrs, MTS was added to each well and further incubated for another 2 hrs. The absorbance at 490 nm was detected with a microplate reader. The photosensitizing function of PPNs was evaluated as well. The cells were incubated with blank/PPNs-DOX, respectively. After 6 hours treatment, cells were washed with PBS 3 times, and replaced with fresh medium in the plates followed by exposure to 30 mW/cm$^2$ NIR light for 2 min. 72 hrs after light irradiation, cell viability was determined using MTS assay. To measure intracellular ROS production in ovarian cancer cells, the cells were incubated in medium containing 10 µM 2',7'-Dichlorofluorescin diacetate (DCF) for 30 min after light irradiation. The cells were washed thrice with PBS, fluorescent cell images were immediately acquired under fluorescence microscope using Metamorph programme. Other cells were trypsinized and used for flow cytometry analysis. Then mitochondrial membrane potential (ΔΨm) was evaluated in pre-treated ovarian cancer cells with PPNs. 18 hrs after illumination with NIR light, cells were loaded with 50 nM DiOC6(3) for 20 min. At the same time, cells were stained with propridium iodide (dead cells) and Hoechst 33342 (nucleus). Fluorescent images were acquired using fluoresce microscope. Next, to investigate the cellular response to PPNs and photodynamic therapy, SKOV-3 cells were treated with or without 10 µM PPNs for 2 hrs followed by exposure with or without light for 2 min. After 24 or 48 hrs incubation, expression level of caspase3 was measured by western blot. Lastly, cell morphology was studied via Hema3® staining SKOV-3 cells were seeded on 6-well plate, treated with or without 10 µM PPNs for 2 hrs. 16 hrs after light irradiation, cells were stained with Hema3®, observed under fluorescence microscopy.

Figure 19A:
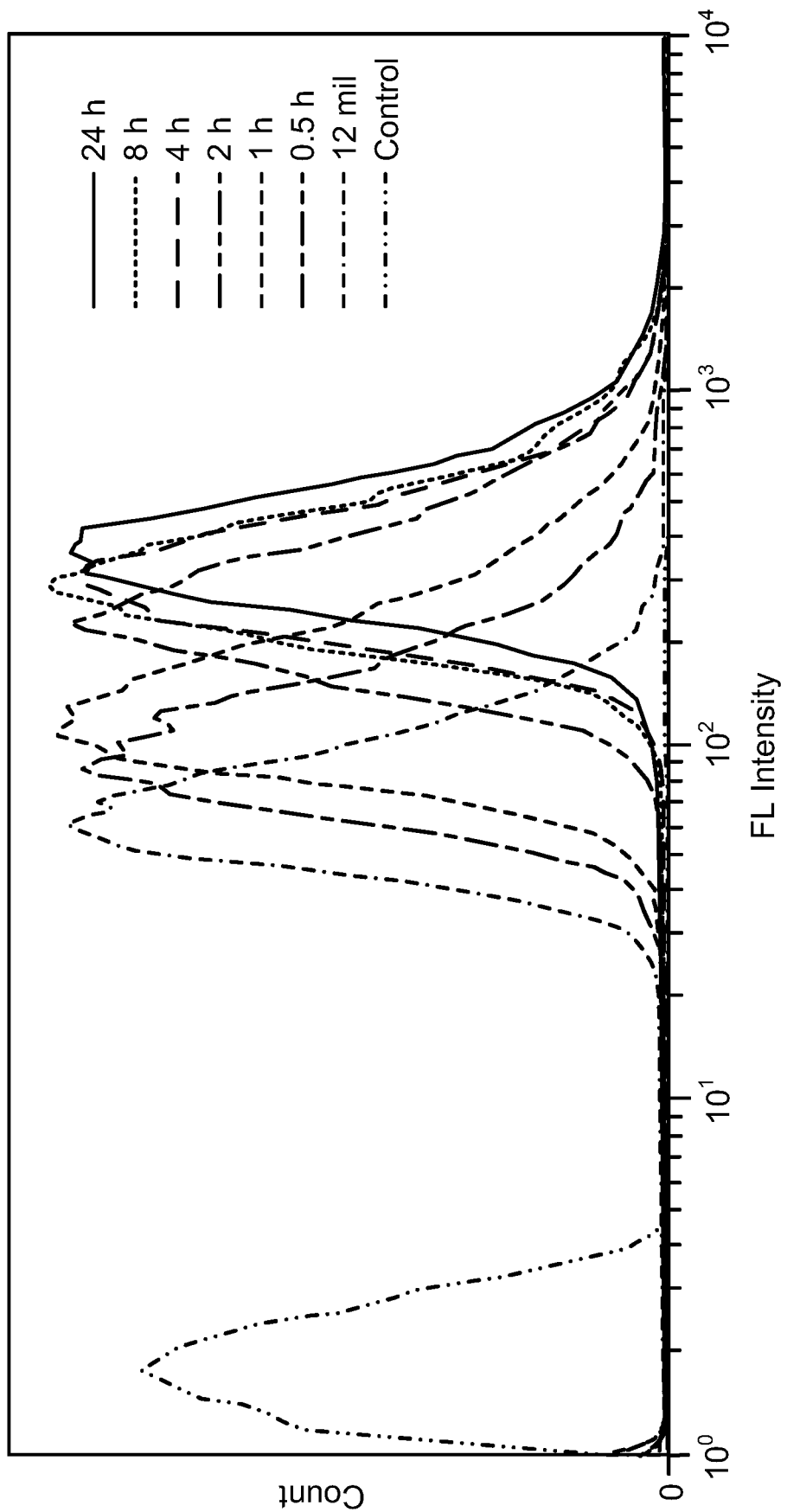
FIG. 19(A) shows porphyrin fluorescence in SKOV-3 cells after incubation with PPNs at different time points.
Figure 19B:
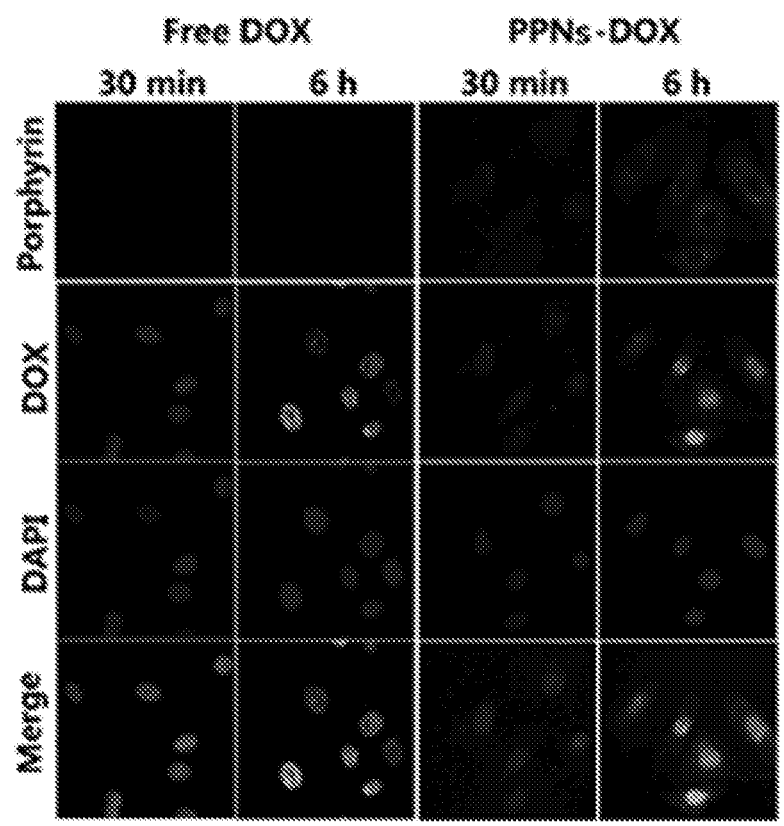
FIG. 19(B) shows confocal images of SKOV-3 cells incubated with 100 μg/ml free DOX and DOX-loaded PPNs for 30 min and 6 h.

The cellular uptake efficiency of PPNs in SKOV3 ovarian cancer cells was quantified with flow cytometry at different incubation time points (FIG. 19a). The fluorescence intensity of PPNs rapidly increased after 15 min incubation, and remained stable after 4 hrs. Next, intracellular uptake behavior and localization of free DOX and DOX-loaded PPNs were observed in SKOV-3 cells with confocal microscopy (FIG. 19b). After 30 min incubation, DOX fluorescence from DOX-loaded PPNs was mainly located in the cytoplasm while that from free DOX could be observed in the nuclei. At 6 hrs after incubation, DOX fluorescence from free DOX group was completely transported into the nuclei, whereas that from DOX-loaded PPN group remained a small amount in the cytoplasm. Additionally, a marked increase in porphyrin fluorescence from PPNs was visualized in the cytoplasm at 6 hrs, compared to that at 30 min after incubation.

An in vivo pharmacokinetic study of PPNs-DOX was conducted in rats. The jugular vein of a male Sprague-Dawley rat was cannulated and a catheter was implanted for IV injection and blood collection. The catheter patency was maintained by flushing the catheter with sterile saline once a week. Free DOX and PPNs-DOX were injected through the catheter at a dose of 5 mg/kg body weight, as well as equivalent dose of blank PPNs, respectively (n=2 for each group). Whole blood samples (approximately 200 µL) were collected via jugular vein catheter before dosing and at 1, 3, 5, 15, 30, 60, 120, 240, 480 and 1440 minutes post-dosing. At each time point, about 50 µL blood was drawn with a new syringe then discarded. Another new syringe took the 200 µL of sample blood. Then 50 µL of sterile saline was used to flush the catheter followed by 50 µL of heparin in saline. The samples were immediately centrifuged and the plasma was separated and stored at −20° C. until analysis. 20 µL of the plasma were added to 180 µL extraction buffer (10% Triton X-100, deionized water and acidified isopropanol (0.75 N HCl) with volumetric ratio of 1:2:15), DOX was extracted overnight at −20° C. The fluorescence of DOX was determined at excitation/emission of 480/580 nm and 410/670 nm, respectively.

Figure 19C:
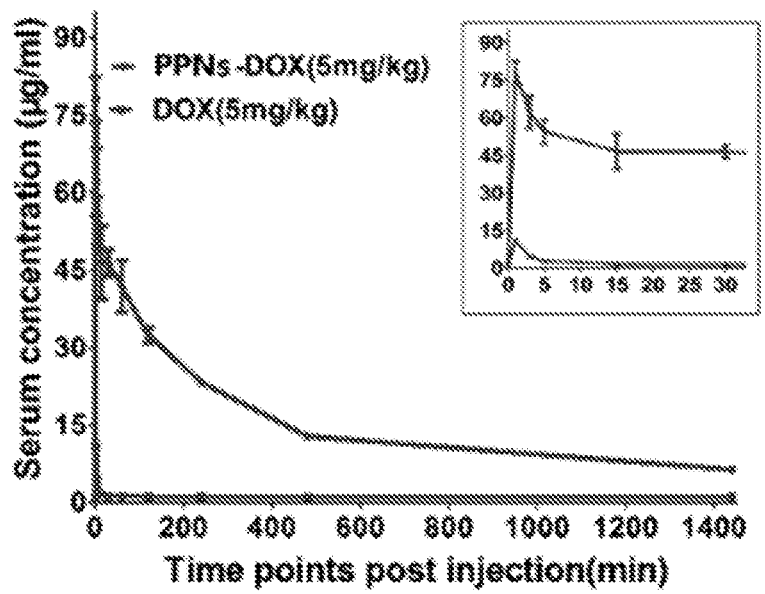
FIG. 19(C) shows the serum concentration of DOX and DOX-loaded PPNs observed during an in vivo pharmacokinetic study.
Figure 19D:
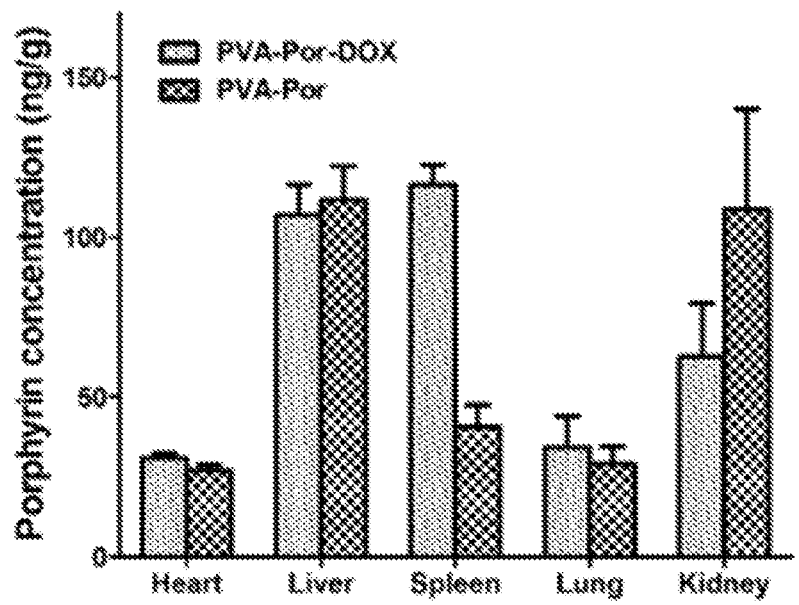
FIG. 19(D) shows the porphyrin concentration accumulated in various organs during a pharmacokinetic study.

The in vivo pharmacokinetic study in rats showed that DOX in PPNs-DOX group exhibited significantly prolonged circulation time in blood, compared to that in free DOX group (FIG. 19c). The major side-effect of DOX is cardiotoxicity. Interestingly, decreased cardiac accumulation of DOX was observed by using the formulation of PPNs-DOX compared to free DOX, indicating PPNs may be able to reduce the cardio-toxicity of this drug (FIG. 19d).

Example 11

Near Infrared Fluorescence (NIRF) Optical Imaging Using

All animal experiments present in this study were performed according to animal protocols approved by the Animal Care and Use Administrative Advisory Committee at University of California, Davis. Female nude mice ages 6 to 8 weeks were purchased from Harlan Laboratories. Ovarian cancer xenograft mouse model was established by subcutaneously injecting $5 \times 10^6$ SKOV-3 cells resuspended in 100 µl of mixture of PBS and Matrigel (1:1, v/v) at the right flank. When tumor xenograft reached 6 to 10 mm in diameter, the mice were subjected to NIRF optical imaging. For each mouse, 200 µl PBS solution of PPNs (20 mg/ml) was injected via tail vein (n=5). At different time points (0.15, 3, 6, 24, 48 and 82 hrs) post-injection, mice were anesthetized by intraperitoneal injection of pentobarbital (60 mg/kg), and scanned using Kodak multimodal imaging system IS2000MM with the excitation at 625 nm and the emission at 700 nm. At 6, 24, 48 and 82 hrs after in vivo imaging, mice were euthanized. Tumors and all major organs were excised for ex vivo imaging.

Figure 19E:
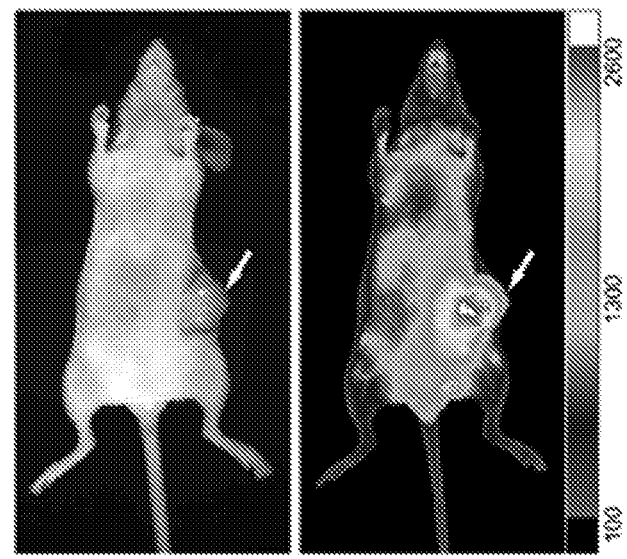
FIG. 19(E) shows representative in vivo NIRF optical images of subcutaneous SKOV-3 tumor-bearing mice at 18 h after intravenous administration of PPNs.
Figure 19F:
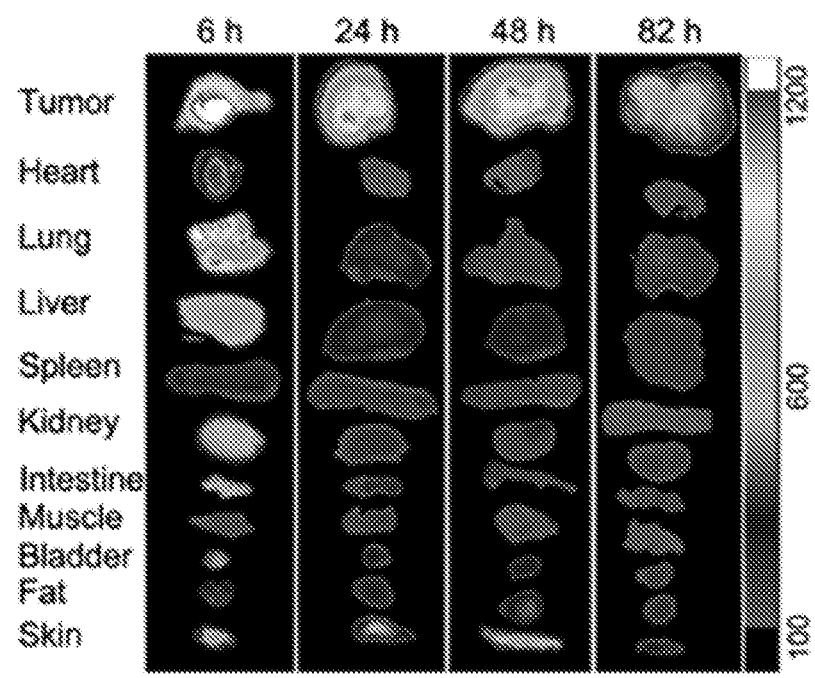
FIG. 19(F) shows ex vivo optical images of tumors and major organs of SKOV-3 xenograft-bearing mice euthanized at different time points after injection of PPNs.

As shown in FIG. 18g, PPNs emit NIR fluorescence with a peak at 680 nm, which is intrinsically suitable for in vivo fluorescence optical imaging. By intravenous injection of PPNs into mice bearing SKOV-3 ovarian cancer xenografts, it's convenient to monitor the real-time distribution, excretion, and tumor targeting efficiency of PPNs. At 5 min post-injection, there was a strong overall fluorescence signal of the entire animal. Subsequently, preferential PPN accumulation at tumor sites was observed from 6 hrs to 82 hrs after administration, which is probably attributed to the enhanced permeability and retention (EPR) effect (FIG. 19e). Ex vivo images (FIG. 19f) at different time points post-injection further confirmed the preferential uptake and retention of PPNs in tumor tissue, compared to other normal organs, although there was some uptake in lung and liver at 6 hrs, which is likely due to the nonspecific clearance by Kupffer cells and macrophages.

Example 12

Preparation of Gadolinium-Chelated PPNs

The $Gd^{3+}$ chelation was carried out through the addition of $GdCl_3$ to the PVA-porphyrin aqueous solution under stirring for 2 hrs at room temperature (Shahbazi-Gahrouei D et al., *Iran Biomed. J.*, 5 (2-3) 87-95 (2001)). The molar ratio of PVA-porphyrin and $Gd^{3+}$ depended on the amount of porphyrin conjugated on PVA. For a typical solution of 1 mmol porphyrin, 10 mmol of $GdCl_3$ were added. The removal of free $Gd^{3+}$ was performed via column filtration with a 10 kDa molecular weight cutoff membrane. The Gd-chelated PPNs were then reconstituted with PBS buffer. The free gadolinium in Gd-chelated PPNs was detected by Arsenazo III methods. Arsenazo III could hind to metal ions to form an Arsenazo-metal ion complex, which can be quantified colormetrically. Arsenazo III does not bind to complexed metal ions.

Example 13

In Vitro and In Vivo Magnetic Resonance Imaging (MRI) Studies

Solutions containing various concentrations of Gd-chelated PPNs were used for $T_1$ measurements on a Bruker Biospec 7 T MRI scanner. $T_1$-weighted contrast enhancement was performed using a multi-slice multi-echo (MSME) sequence with 411.7 ms repetition time (TR) and 14.3 ms echo time (TE). For $T_1$-weighted images of in vivo experiments, nude mice bearing SKOV-3 ovarian cancer xenografts were imaged with a FLASH imaging sequence at the 7 T. For all of the mice, transaxial and coronal $T_1$-weighted images were taken before injection and at different time points post injection of Gd-PPNs. The parameters were set as follows: spin-echo method. TR=500 ms, TE=15 ms, field of view (FOV)=6×4 cm (transaxial) or 8×6 cm (coronal), matrix size=128×128, and slice thickness=1 mm; FLASH method, TR=235.3 ms, TE=4 ms, flip angle=10°, FOV=6×4 cm (transaxial) or 8×6 cm (coronal), matrix size=128×128, and slice thickness=1 mm.

Figure 20A:
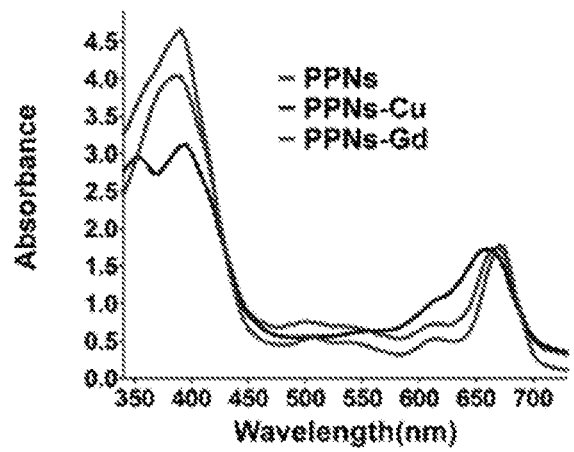
FIG. 20(A) shows the absorbance spectra of PPNs (red), $Gd^{3+}$-chelated PPNs and $Cu^{2-}$-chelated PPNs (blue).
Figure 20B:
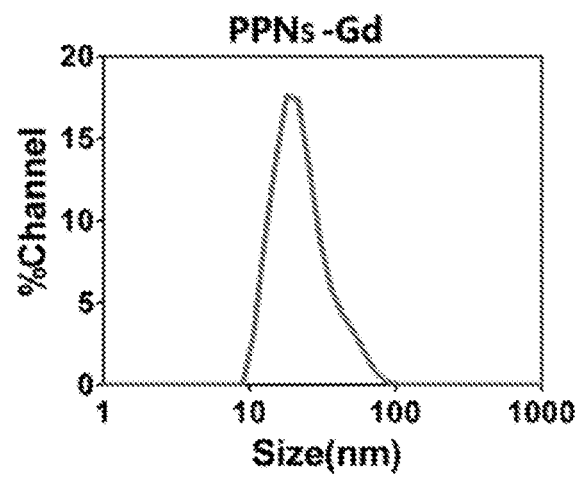
FIG. 20(B) shows the DLS size distribution of $Gd^{3+}$-chelated PPNs.
Figure 20C:
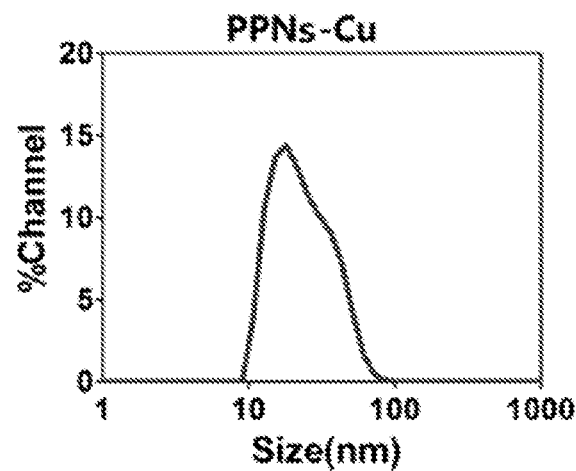
FIG. 20(C) shows the DLS size distribution of $Cu^{7+}$-chelated PPNs.
Figure 20D:
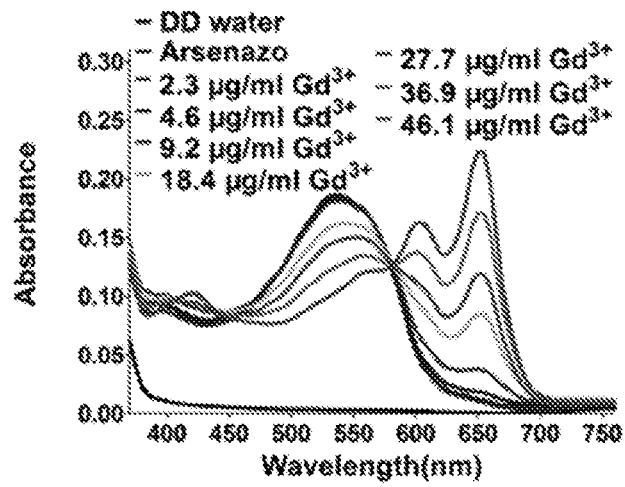
FIG. 20(D) shows the absorption spectra for each calibration standard of 100 μL 0.2 mM Arsenazo III, 50 μL standard and 850 μL water, used to determine the free gadolinium.
Figure 20E:
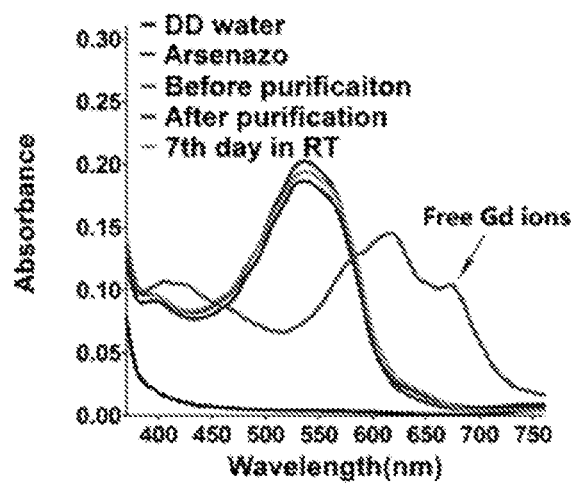
FIG. 20(E) shows absorption spectra of Arsenazo III solution with $Gd^{3+}$-chelated PPN solution after centrifuge filtration.

In addition to their unique photonic properties and excellent drug loading capacity, PPNs could conveniently chelate imaging agents such as gadolinium ($Gd^{3+}$) and copper ($^{64}Cu$), because porphyrins and their tetrapyrrole analogues can chelate with an incredibly diverse range of metal ions to form metalloporphyrin complexes. The chelation could be done separately or simultaneously with the drug loading procedure through the self-assembly of PVA-Por. After metal chelation, the absorption spectrum of Cu-chelated PPNs in PBS exhibited a 10-nm blue-shift to 660 nm while Gd-chelated PPNs exhibited a 5-nm red-shift to 675 nm, in contrast to the parent PPNs without metal ions with the peak at 670 nm (FIG. 20a). These metal ion-chelated PPNs showed similar particle size distributions as parent PPNs (FIG. 20b, c). The free metal ions in the PPN solution were removed via column filtration. Detection of unchelated $Gd^{3+}$ in PPN suspended solution was carried out using the routine arsenazo III method (Clogston, J. D et al., *Methods Mol. Biol.*, 697 101-8 (2011)). As shown in FIG. 20d, a calibration curve was first established to determine the concentration of free gadolinium. The arsenazo III method showed a strong visible absorbance at around 550 nm in the absence of $Gd^{3+}$, whereas it absorbed at 660 nm when complexed with $Gd^{3+}$ ions. After purification, it was confirmed that $Gd^{3+}$ was not detectable, up to 7 days at 4° C. in PBS (FIG. 20e). Instant thin-layer chromatography (ITLC) was immediately performed to evaluate the radiochemical purity and yield after the incorporation of $^{64}Cu$ into the PPNs. After centrifuge filtration, approximate 95% radiochemical purity was achieved, indicating that $^{64}Cu$-labeled PPNs could be used as a potential positron emission tomography (PET) imaging probe.

Figure 20F:
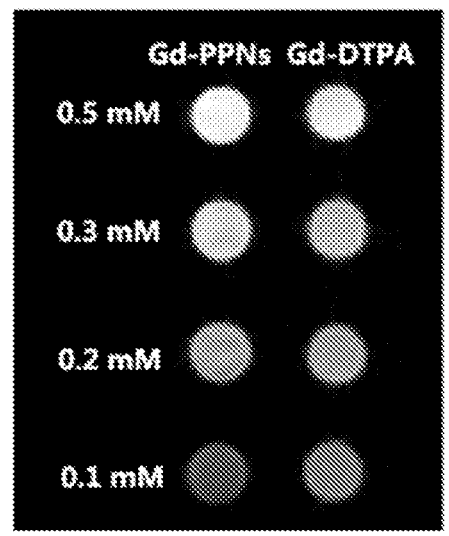
FIG. 20(F) shows $T_1$-weighted images of Gd-PPN and Gd-DTPA solutions at 7 T.
Figure 20G:
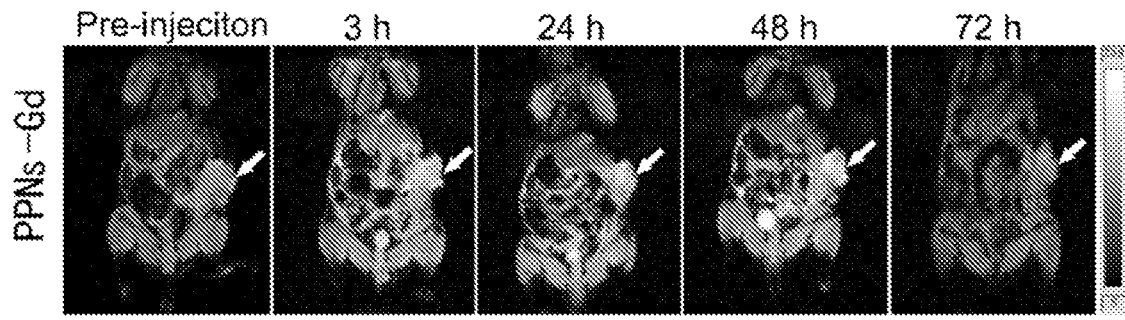
FIG. 20(G) shows in vivo $T_1$-weighted imaging of SKOV-3 tumor bearing mice at five time points (pre-injection, 3 h, 24 h, 48 h and 72 h post-injection). The white arrow indicates the tumor.

The performance of Gd-PPNs was further investigated as an MRI probe in vitro and in vivo. The relaxivity of Gd-PPNs was evaluated in vitro using a 7 T MRI. The longitudinal ($T_1$) relaxation times of Gd-PPNs were measured in SDS solutions with different $Gd^{3+}$ ion concentrations. The results showed an obvious dose-dependent $T_1$ enhancement (FIG. 20f). The $r_1$ was then calculated to be 4.17 $mM^{-1}s^{-1}$. However, no obvious $T_1$ signal enhancement was observed when Gd-PPNs retain their integrity in PBS. Finally, in vivo $T_1$-weighted imaging was performed on nude mice bearing SKOV-3 ovarian cancer xenografts with 7 T MRI. As shown in FIG. 20g, these $T_1$ images after 3 hrs of Gd-PPNs administration clearly demonstrated a significantly high contrast enhancement of the implanted tumor. Additionally, the tumor contrast enhancement could maintain up to 48 hrs, which was significantly stronger and longer than DTPA-Gd-caused T1 enhancement.

Example 14

In Vitro Antitumor Efficacy of Doxorubicin-Loaded Nanoparticles

Figure 21A:
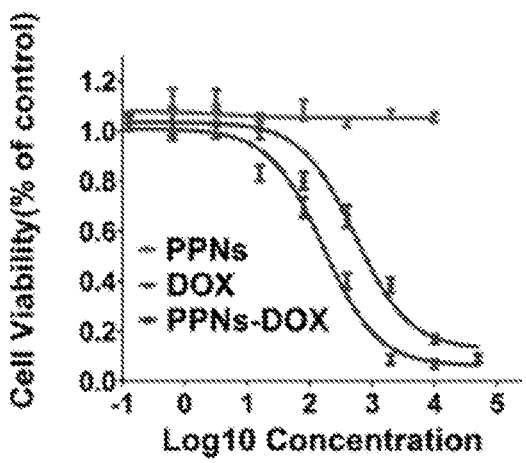
FIG. 21(A) shows the cytotoxicity of blank PPNs and the antitumor effects of DOX-loaded PPNs in SKOV-3 ovarian cancer cells, compared with free DOX.
Figure 21B:
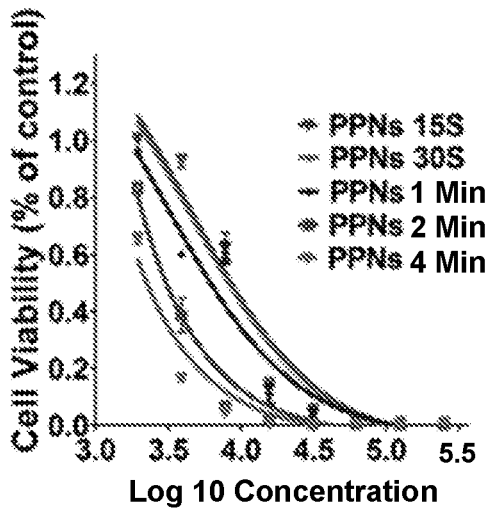
FIG. 21(B) shows cell viability of SKOV-3 cancer cells after 2 h incubation with PPNs followed by exposure to 30 mW/cm² NIR light for 15 s, 30 s, 1 min, 2 min and 4 min.
Figure 21C:
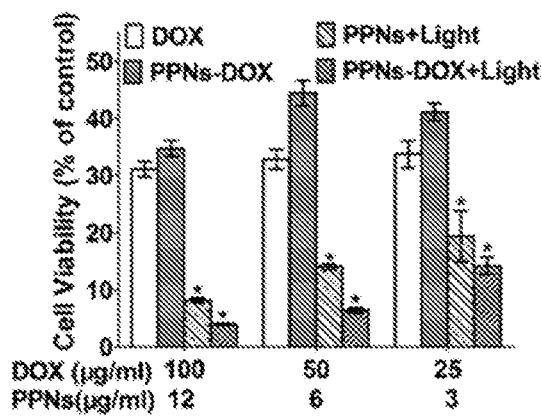
FIG. 21(C) shows the cell killing effect of DOX combined with PPN-mediated photo-therapy. SKOV-3 cancer cells were treated with PPM, free DOX, and DOX-loaded PPNs for 6 h. Cells were irradiated with light for 2 min, and cell viability was measured by MTS assay after 72 h (P<0.05).
Figure 21D:
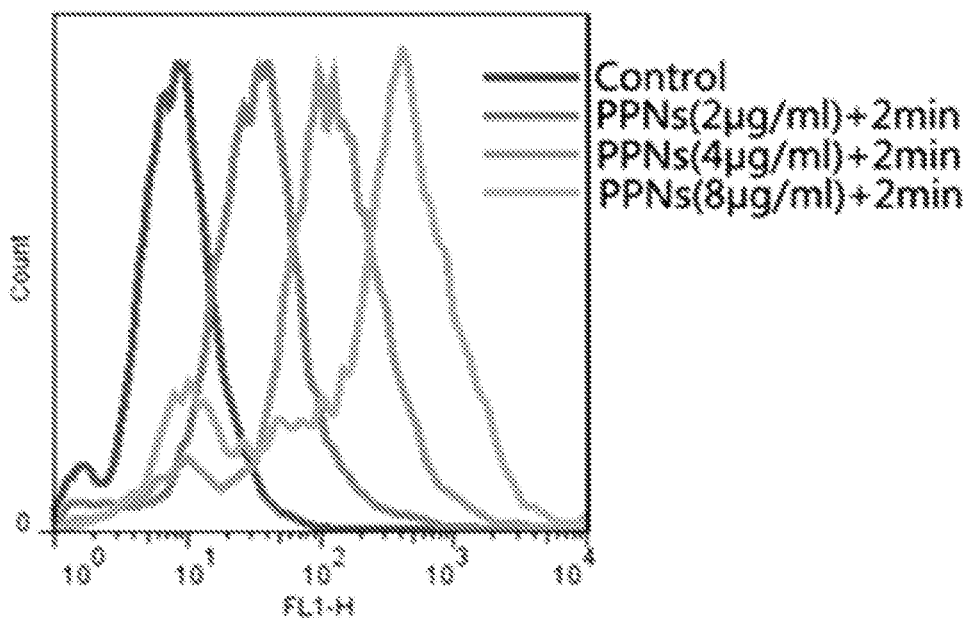
FIG. 21(D) shows ROS production as quantified by flow cytometry in SKOV-3 cancer cells treated with different concentrations of PPNs for 2 h, followed by 30 mW/cm² laser irradiation for 2 min.
Figure 21E:
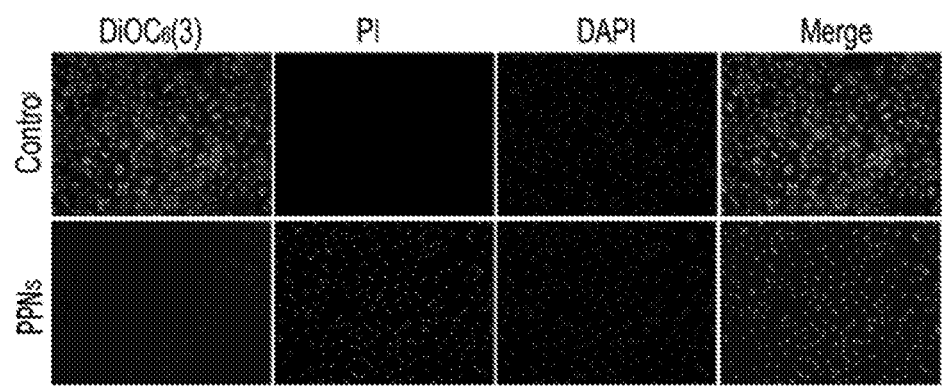
FIG. 21(E) shows SKOV-3 cancer cells incubated with 100 μg/ml PPNs for 2 h followed by light irradiation for 2 min. 24 h later, cells were stained with 40 nM $DiOC_6(3)$ (Green, mitochondrial membrane potential), propridium iodide (P1, red, dead cells) and Hoechst 33342 (blue, nucleus).
Figure 21F:
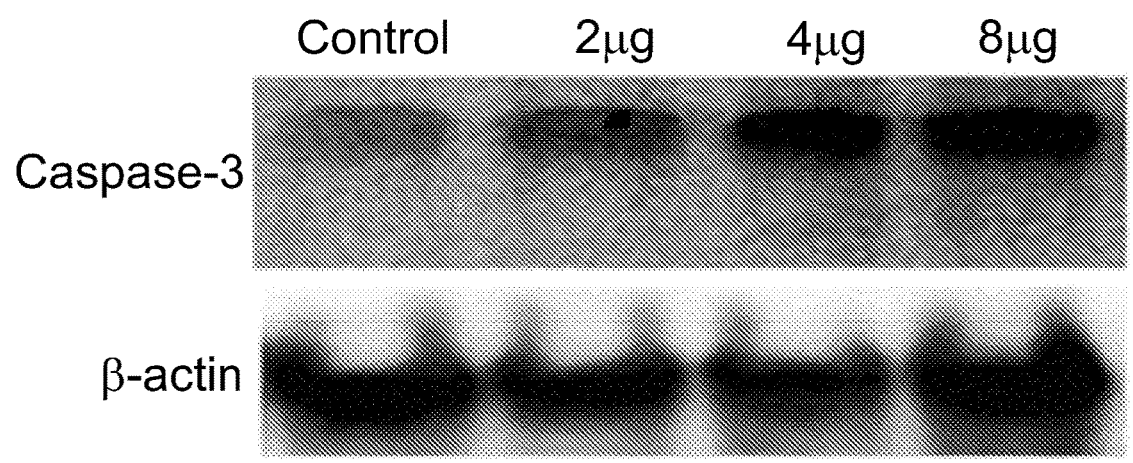
FIG. 21(F) shows SKOV-3 cancer cells treated with different concentrations of PPNs for 2 h followed by PDT. Caspase-3 expression was measured by western blot analysis 24 h later.
Figure 21G:
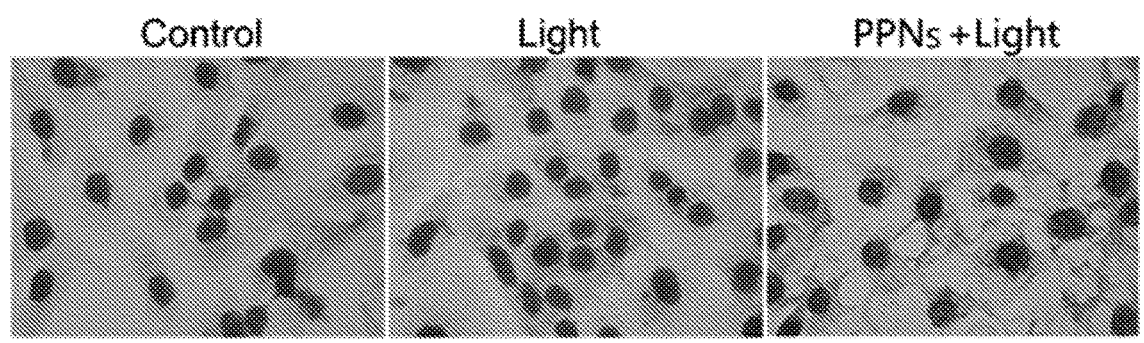
FIG. 21(G) shows cell morphology of SKOV-3 cancer cells after PDT was evaluated by Hema 3 staining.

The in vitro antitumor efficacy of free DOX, empty PPNs and DOX-loaded PPNs against SKOV-3 ovarian cancer cells after 72 hrs continuous exposure was investigated with an MTS assay. As shown in FIG. 21a, similar dose-dependent cytotoxicities were observed for free DOX and DOX-loaded PPNs. Additionally, the empty PPNs did not exhibit detectable cytotoxic effects at all the concentrations up to 20 mg/mL without light exposure. Furthermore, the phototoxic effect of PPNs against SKOV-3 cells was studied, by exposure of NIR light at 30 mW/cm$^2$ for 15 s, 30 s, 1 min, 2 min and 4 min. Prior to the light irradiation, the cells were incubated with different concentrations of PPNs for 2 hrs, followed by thoroughly washing out and replacing the medium. The results of MTS assay demonstrated both a light-dose dependent and PPN-concentration dependent cell killing upon light illumination (FIG. 21b). Interestingly, DOX-loaded PPNs were able to take advantage of both chemotherapy and photodynamic therapy for cell killing. The combination therapy via DOX-loaded PPNs was significantly more efficacious than free DOX, PPN-DOX without light and PPN-mediated photodynamic therapy alone (FIG. 21c). The mechanism of cell death after light irradiation was further investigated. Compared to the control group, significantly increased reactive oxygen spices (ROS) production was detected by flow cytometry (FIG. 21d). Furthermore, a marked increase in ROS fluorescence was observed under fluorescence microscopy. The ROS production led to loss of mitochondrial membrane potential and cell apoptosis, verified by propidium iodide (PI) and 3,3'-dihexyloxacarbocyanine iodide (DIOC$_6$(3)) co-staining (FIG. 21e) and increased caspase-3 activation (FIG. 21f), respectively. As shown in FIG. 21e, cells in the control group displayed green fluorescence of DIOC$_6$(3) without red fluorescence of PI, whereas cells in the treated group displayed only red fluorescence of PI, suggesting that the cells were killed upon light irradiation. The cellular damage was also observed after the light irradiation (FIG. 21g).

Example 15

Photodynamic Therapy Using PPNs

The thermal effect during irradiation was evaluated by monitoring the temperature of PPNs solutions using an infrared thermal camera (FLIR). PVA-porphyrin solutions in the absence and in the presence of SDS were irradiated with a 690 nm diode laser system (Applied Optronics, Newport, Conn.), and the power was measured as 1 W with a spot size of 5 mm diameter for 30 s. The concentrations of PPNs in the solutions were 0.019 to 0.3 mg/ml, calculated on porphyrin content. The tumor temperature in SKOV-3 bearing mice was also monitored during irradiation. PPNs were injected via tail vein into the mice at a dose of 2 mg/kg based on the porphyrin content. After 24 hrs, the tumor was irradiated with a 690 nm laser at a light dose of 1.25 W/cm$^2$ for 180 s. Tumor temperature changes in PBS control mice were also recorded with the thermal camera. After light irradiation, the tumor was immediately harvested to measure introtumoral ROS production. DCF was used as the ROS indicator by mixing with 100 μL of tissue lysates derived from tumors treated with PPNs and PBS. To evaluate PDT/PTT caused tumor ablation, the whole tumors were dissected 24 hours after irradiation. The specimens were fixed in 10% formaldehyde, cut into thin slices and stained with H&E. The sections were viewed and photographed under a bright-field microscopy at 20×.

MRI guided phototherapy. MRI was used to observe tumor development in SKOV-3 tumor-bearing mice after the phototherapy. MR images before injection and 3, 24, 48, 72, 96, 168 and 216 hrs post-injection were collected using the 7 T MRI scanner. The tumors in the treatment group were irradiated by the 690 nm laser at 1.25 W cm$^{-2}$ for 2 min 24 hrs after injection. Control MR images of tumor-bearing mice without laser irradiation were acquired using the same settings.

Phototherapy and tumor response. Subcutaneous SKOV-3 tumor-bearing mice were used for in vivo therapeutic study when tumor volumes reached 80-120 mm$^3$ (designate as Day 0). The therapeutic efficacy and toxicity profiles of different PPNs formulations were evaluated. On day 0, all mice were randomly divided into seven groups (n=6). Mice were intravenously administered with PBS, blank PPNs, DOX·HCl and PPNs-DOX. The DOX was given at the dose of 2.5 mg/kg, and PPNs was given at the dose of 2 mg/kg, calculated on the porphyrin content. The treatment was given every 5 days on day 0, 5, 10 and 15 for a total 4 doses. For the PPNs group, mice were irradiated under anesthesia with a 690 nm laser at a light dose of 0.5 W/cm$^2$ or 1.25 W/cm$^2$ for 120 s 24 hrs after the injection, and the light dose for PPNs-DOX group was set at 0.5 W/cm$^2$ for 120 s. Tumor size and body weight were measured twice a week. Tumor volume was calculated using the equation (L×W$^2$)/2, where L is the longest and W is shortest in tumor diameters (mm). For humane reasons, mice were sacrificed when tumor volume reached 1000 mm$^3$, which was considered as the end point of survival data. At day 5 after the last dosage, blood samples were collected from each group to test blood cell counts and serum chemistry.

Statistical analysis. Data were presented as mean±standard error (SEM). Student's t-test was used to analyse the statistical differences between two groups, and one-way ANOVA for multiple groups. A value of $P<0.05$ was considered as statistically significant.

Figure 22A:
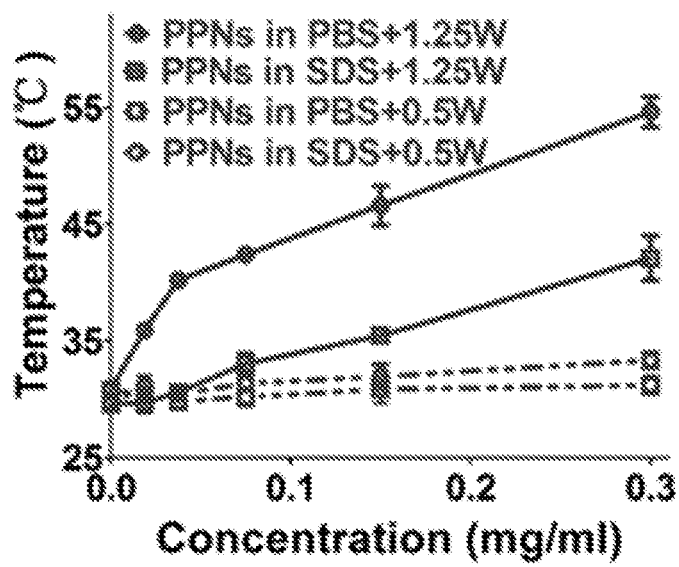
FIG. 22(A) shows the temperature increase curve of PPNs in the absence and in the presence of SDS upon irradiation with a 690 inn laser at the dose of 0.5 W/cm⁷ and 1.25 W/cm² for 30 s (n=3).
Figure 22B:
FIG. 22(B) depicts the light irradiation set-up, including a laser and a SKOV-3 tumor-bearing mouse.
Figure 22C:
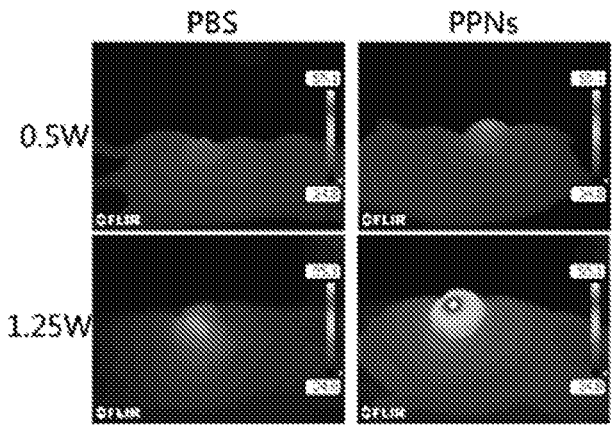
FIG. 22(C) shows representative thermal images of SKOV-3 tumor-bearing mice 24 h after intravenous administration of 2 mg/kg PPNs or PBS. The images were captured by thermal camera in tumors subjected to various irradiations with a 690 nm laser.
Figure 22D:
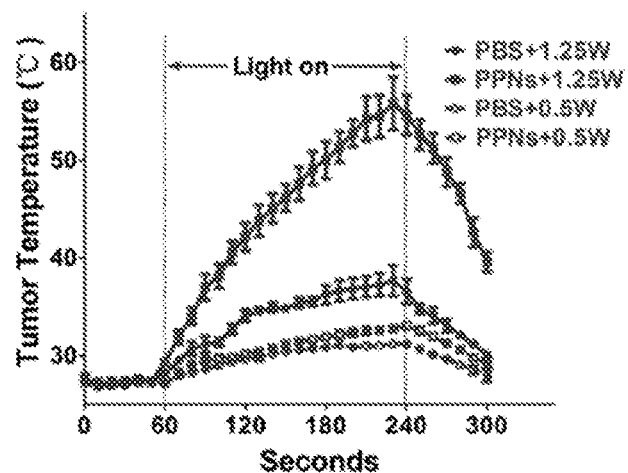
FIG. 22(D) shows a tumor temperature increase curve during laser irradiation for 180 s (n=3).
Figure 22E:
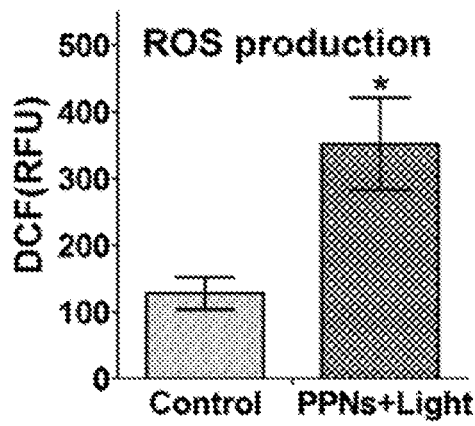
FIG. 22(E) shows ROS production at the tumor site in SKOV-3 tumor-bearing mice treated with 2 mg/kg PPNs or PBS for 24 h followed by laser irradiation for 2 mm (P<0.05).

Not only do PPN have imaging functions, they can also be used as photosensitizers for PDT and PTT. The photothermal transduction (heat generation) and photodynamic effect (ROS production) of PPNs were investigated in vitro and in tumors. As PPNs are highly self-quenched in PBS, the thermal effect of PPNs during different doses of light irradiation was evaluated using a thermal camera. The temperature increased rapidly from 31° C. to 54° C. when PPNs solutions at a concentration of 0 to 0.3 mg/ml porphyrin were exposed to a 690 nm laser at 1.25 W/cm$^2$ for 30 s. When PPNs were dissociated in the presence of SDS, the same dose of light caused a mild and continuous temperature increase to 42° C. However, with a laser at 0.5 W/cm$^2$, the temperature of PPNs in PBS and PPNs in SDS only increased to 33° C. and 31° C., respectively (FIG. 22a). The efficiency of photothermal transduction of PPNs was further investigated by recording tumor temperature during irradiation compared to PBS controls (FIG. 22b). The SKOV-3 xenograft-bearing mice were intravenously injected with 3 mg/kg PPNs or PBS. The tumors were then irradiated with 690 nm light at 1.25 W/cm$^2$ for 3 min at 24 hrs post-injection. The tumor temperature in the PBS control group increased moderately to 38° C. while that in the PPN group increased dramatically from 28° C. to 56° C. at the end of 3 min irradiation. However, with irradiation at 0.5 W/cm$^2$ for 3 min, a mild increase to a final temperature of 31° C. and 33° C. was observed in the PBS control group and PPN group, respectively (FIG. 22c, d). Moreover, the ROS production in the tumors upon laser irradiation was measured. In contrast to the PBS control group, significantly higher ROS was generated by light irradiation in the PPN group with irradiation at 0.5 W/cm$^2$ for 3 min (FIG. 22e).

Figure 23A:
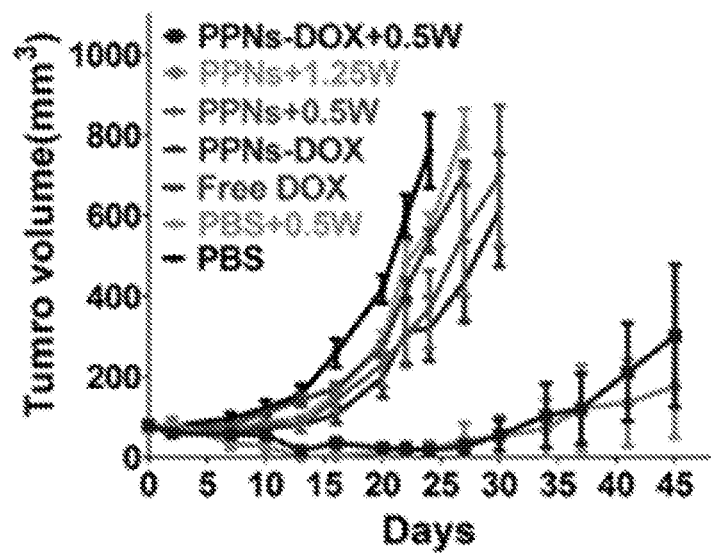
FIG. 23(A) shows in vivo antitumor efficacy after intravenous administration of various DOX formulations combined with PPNs mediated photo-therapy (n=6). The SKOV-3 tumor-bearing mice were intravenously injected with PBS (control), free DOX (2.5 mg/kg), PPNs (2 mg/kg calculate on porphyrin) and PPNs-DOX (PPNs 2 mg/kg, DOX 2.5 mg/kg) on day 0, 5, 10 and 15 followed by irradiation of tumors at 24 h post injection.
Figure 23B:
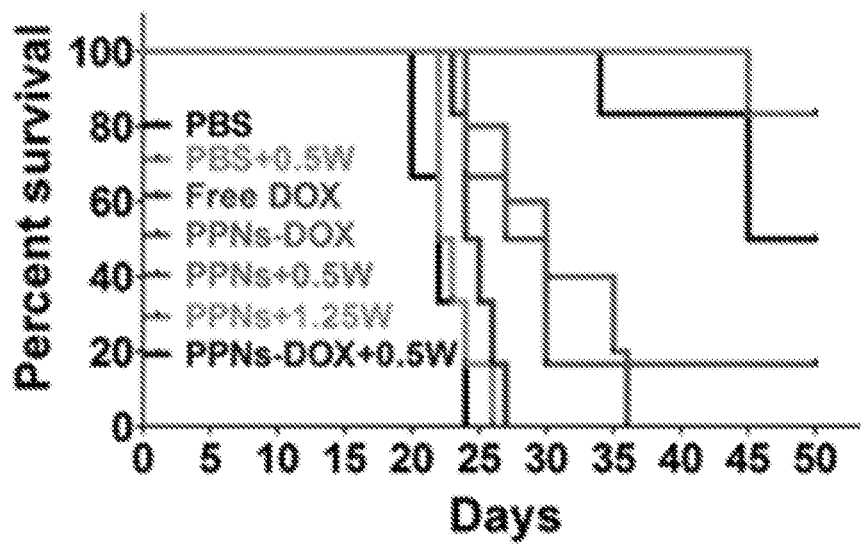
FIG. 23(B) shows Kaplan-Meier survival curves of SKOV-3 tumor-bearing mice treated with above indicated conditions (n=6). The time that the tumor volume reached 500 mm³ was taken as the end point for collection of survival data.

The antitumor efficacy of PPNs was further assessed by monitoring the growth rate of tumors in an in vivo subcutaneous model of ovarian cancer (FIG. 23a). Free DOX and PPNs-DOX at the equivalent DOX dose of 2.5 mg/kg, PPN and PPNs-DOX at the equivalent porphyrin dose of 2 mg/kg, as well as the PBS control were intravenously administrated every five days on days 0, 5, 10 and 15 respectively. Interestingly, mice receiving 2.5 mg/kg free DOX did not exhibit obvious antitumor effect compared to the PBS control group, whereas mice receiving 2.5 mg/kg PPNs-DOX did slow down the tumor growth considerably. In another group, tumors treated with PPNs and laser irradiation (690 nm laser at 0.5 W/cm$^2$ for 2 min) showed similar decreased tumor growth rate. Furthermore, PPNs-DOX mediated combination of phototherapy (low dose, 0.5 W/cm$^2$ for 2 min) with the same dose of DOX showed a remarkable delay in tumor growth compared to PPNs-DOX without light or with 690 nm laser at 0.5 W/cm$^2$ for 2 min. Under irradiation with a high dose of light at 1.25 W/cm$^2$ for 2 min, mice developed eschars on the tumors starting from day 2 post-treatment, and the tissue healed in the following 2 weeks. By day 45, the group of mice that received the high dose of light (690 nm laser at 1.25 W/cm$^2$ for 2 min) achieved a 100% survival rate, then tumor on one mouse progressed and reached the end point. The survival rate of mice in all groups was presented by the Kaplan-Meier survival curve as shown in FIG. 23b. For the mice treated with free DOX or laser-alone, no obvious prolonged survival rate was observed compared to the PBS control group. While mice in the PPNs-DOX treated group started to reach the end point on day 24, and all the mice were euthanized by day 36. However, the mice receiving combination therapy of phototherapy (low dose, low dose, 0.5 W/cm$^2$ for 2 min) with DOX achieved 80% survival rate by day 40, be tumors recurred and 50% of the mice reached the end point by day 45.

Figure 23C:
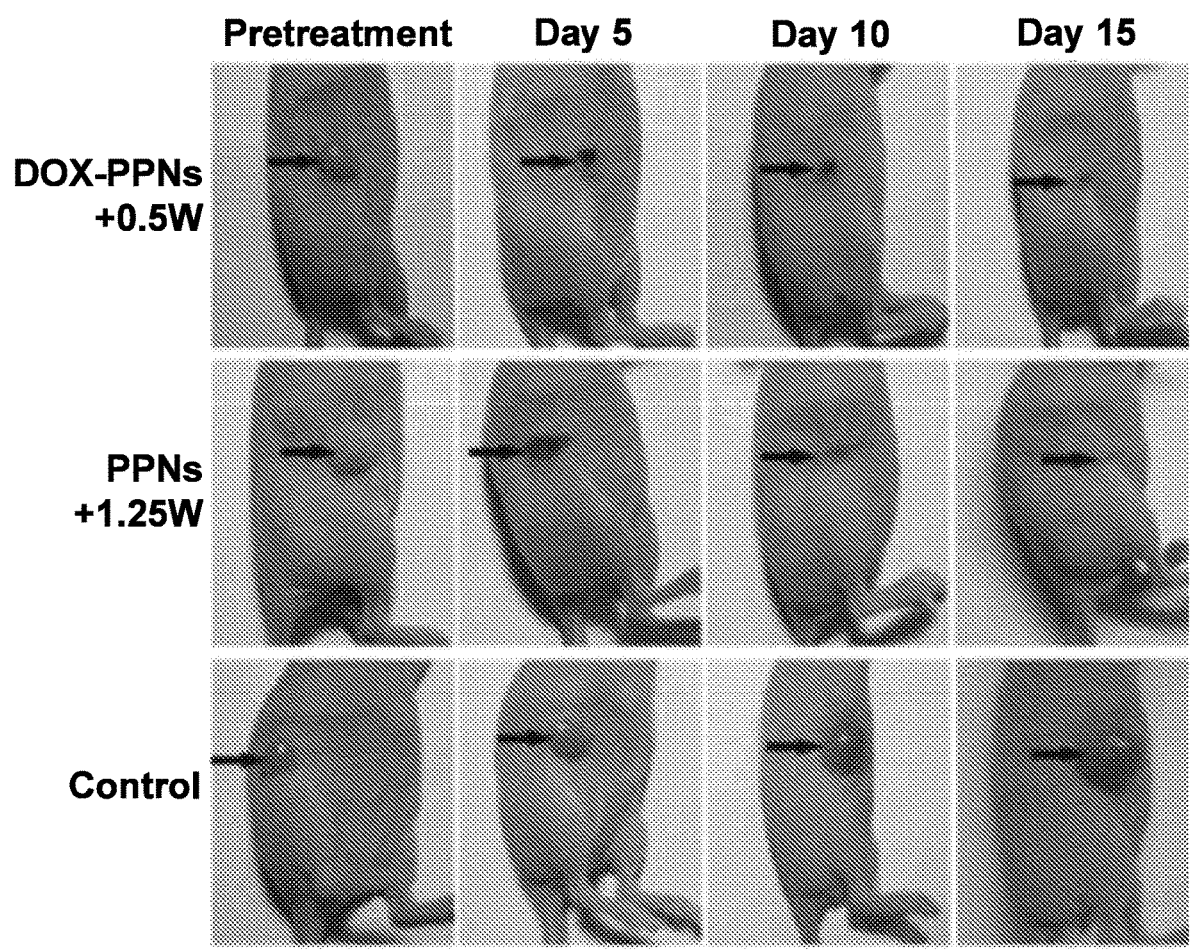
FIG. 23(C) shows the therapeutic response of mice to PPN-mediated photodynamic (0.4 W) therapy and photothermal therapy (1 W).
Figure 23D:
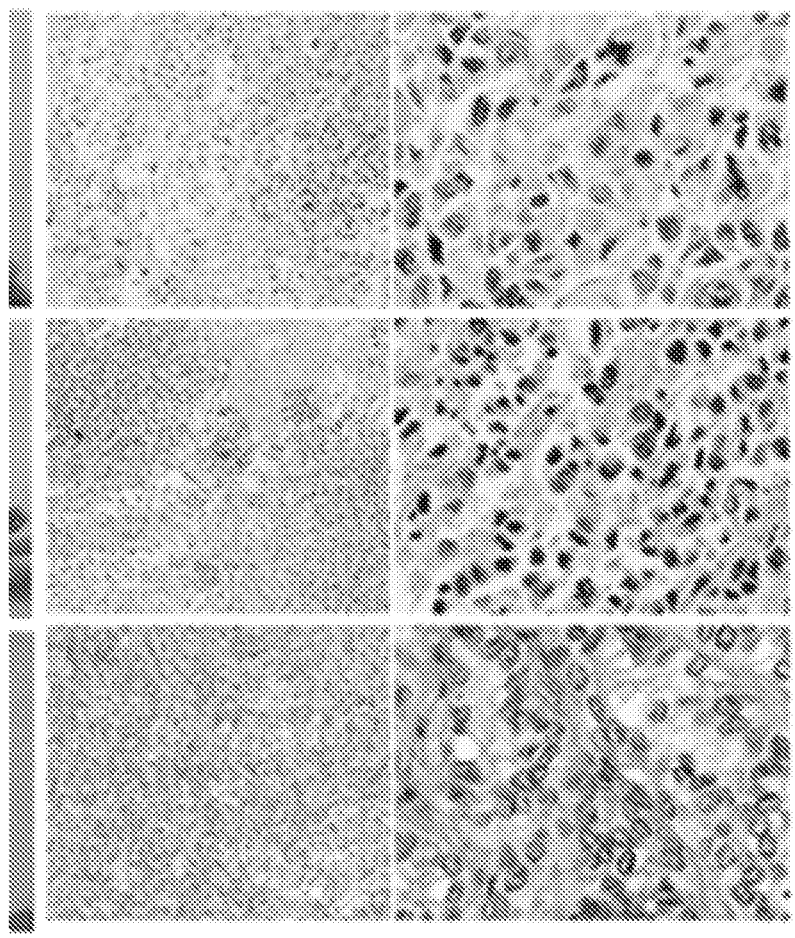
FIG. 23(D) shows H&E staining of tumor sections collected from control mice, mice injected with PPNs-Gd$^{3+}$ injected (2 mg/kg), and irradiated mice (0.4 W and 1 W) at 24 h post injection.
Figure 23E:
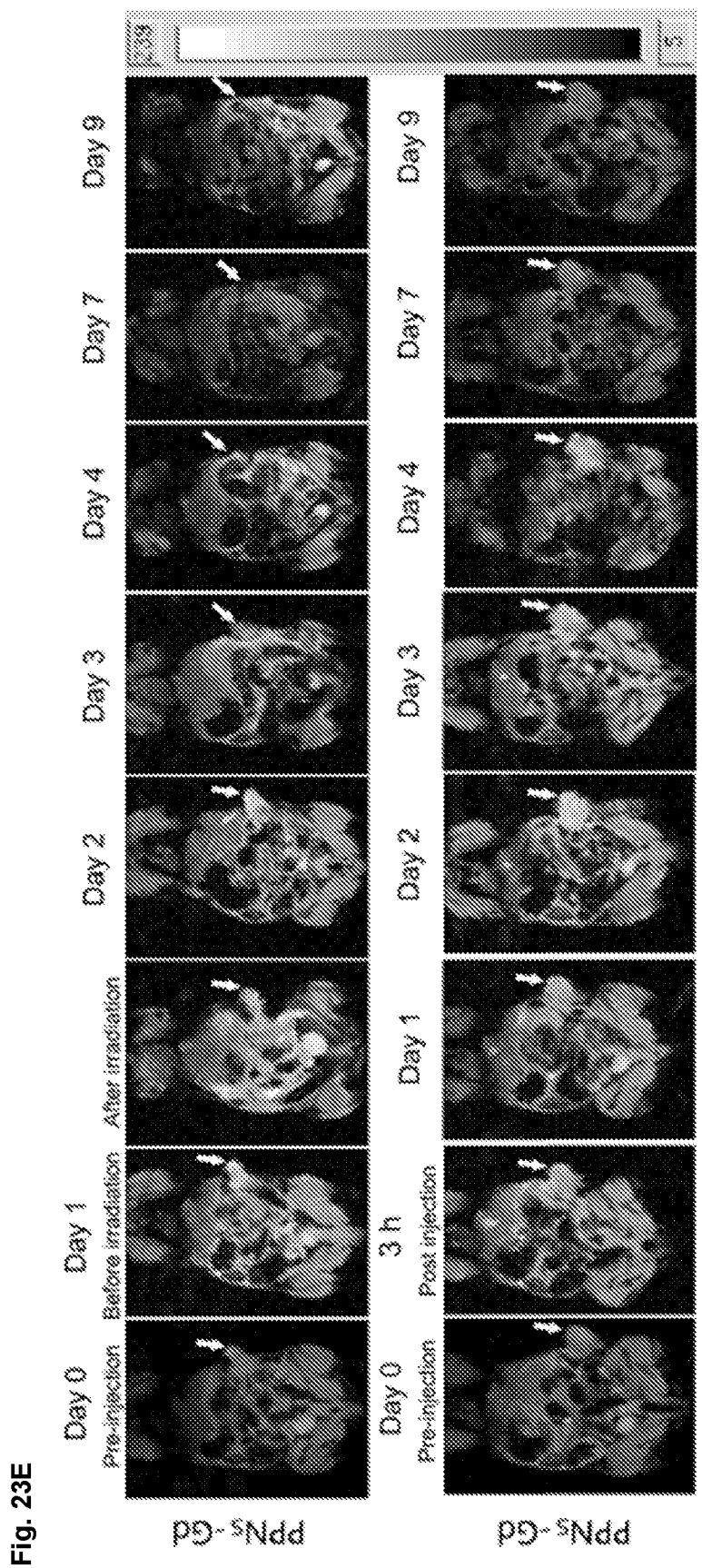
FIG. 23(E) shows coronal MR images of PPNs-Gd$^{3+}$ injected SKOV-3 tumor-bearing mice after laser irradiation (upper panel) or without laser irradiation (lower panel). White arrows indicate the tumor sites. The images at day 0 (pre-injection), day 1, day 3, day 4, day 7 and day 9 were acquired post-injection. MR imaging showed that the tumors in PPNs-Gd$^{3+}$ injected mice were completely ablated upon a 690 nm laser irradiation at the dose of 1.25 W/cm$^{-2}$ for 4 min, whereas the tumor growth of control mice was unaffected.

H&E staining of tumor tissue after phototherapy was performed to evaluate treatment efficacy, and an untreated tumor was used as control (FIG. 23c, d). In the control tumor, no necrosis or obvious cellular damage was noticed, whereas the tumor received low dose of light exhibited signs of sporadic necrosis. Furthermore, tumors irradiated with high intensity of light showed extensive cell destruction and loss of tissue architecture. To assess the delivery of PPNs and the therapeutic efficacy after phototherapy, $T_1$-weighted MR imaging was performed to monitor the tumor growth and phototherapy induced necrosis. MR images of SKOV-3 tumor-bearing mice were collected with a 7 T MRI scanner before Gd-PPNs injection, as well as different time points post-injection (FIG. 23e). The acquired axial and coronal MR images showed significant $T_1$ enhancement of the tumors as indicated by the obvious brightened tumor areas from 3 h post-injection. At 24 hrs, the tumors in the treatment group were exposed to 690 nm laser at 1.25 W/cm$^2$ for 4 min. MR images on day 3 showed obvious shrinkage of tumor volume. By day 4, complete tumor elimination was achieved as revealed by the continuous MRI monitoring. In contrast, the tumors of control mice without laser irradiation were not affected and continued to grow.

Figure 24A:
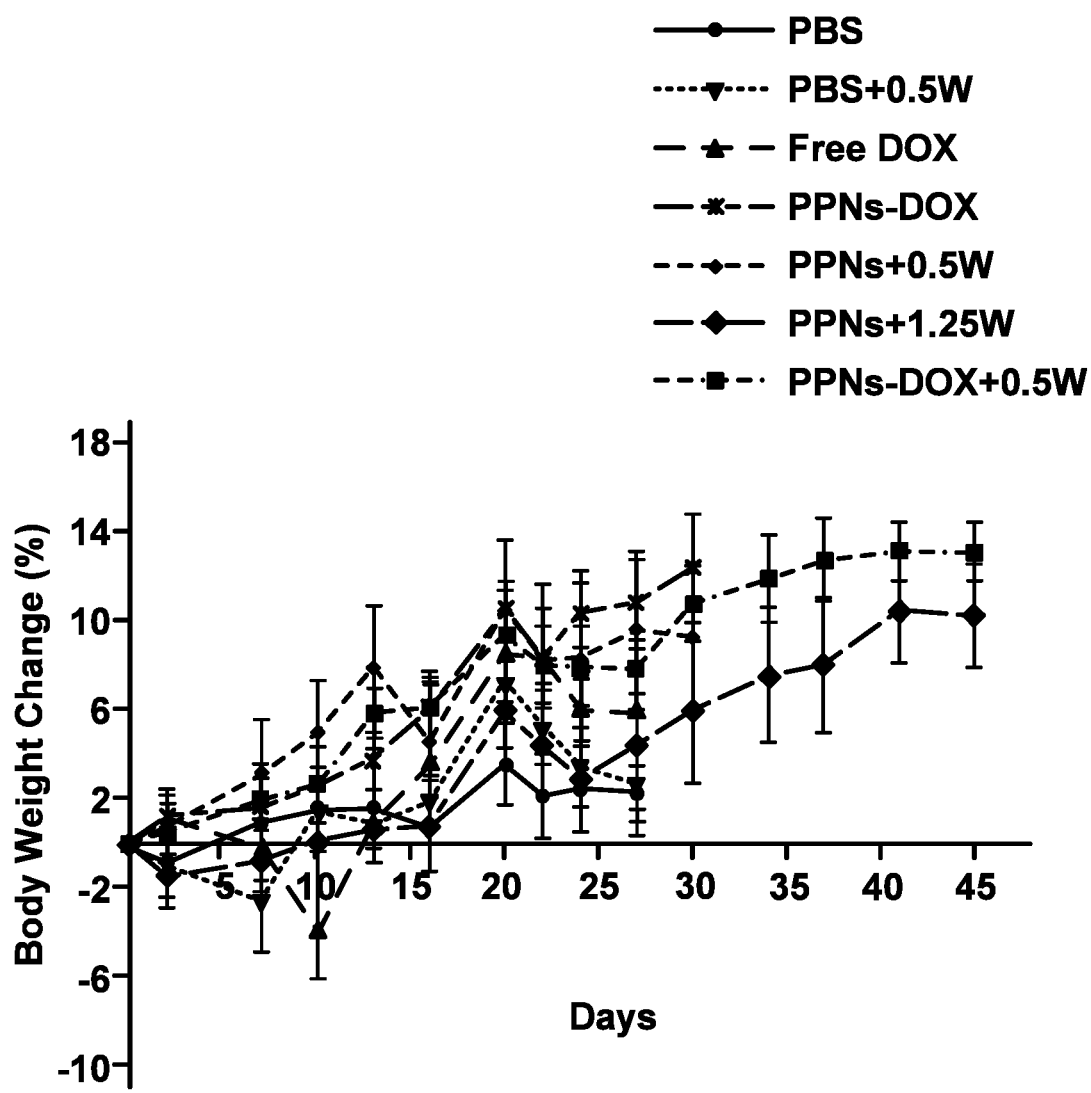
FIG. 24(A) shows body weight changes of SKOV-3 tumor-bearing mice after intravenous administration of various DOX formulations with or without light irradiation (n=6)
Figure 24B:
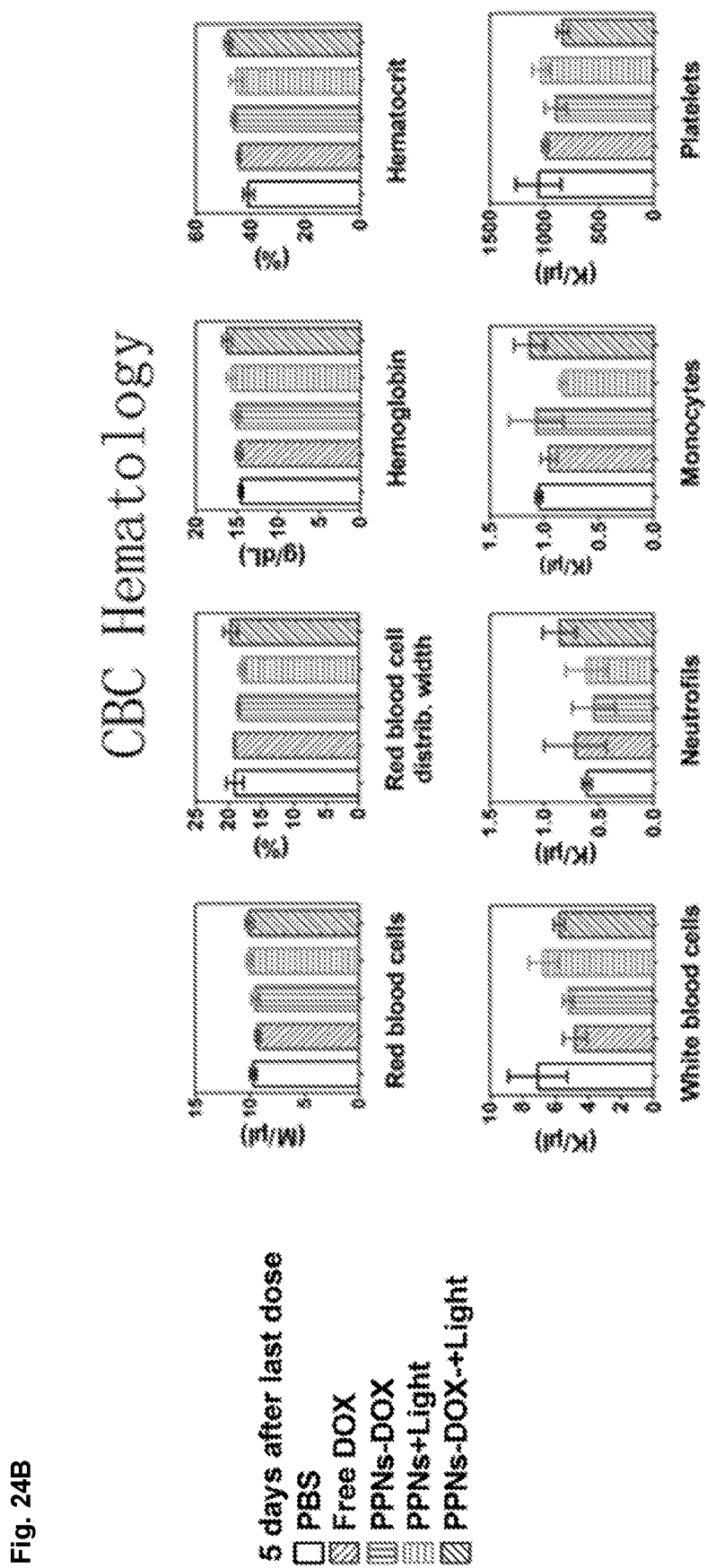
FIG. 24(B) shows blood cell counts and serum chemistry of mice treated by intravenous administration of PPNs or PBS, 50 days post treatment (mean±SD, n=3).
Figure 24B:
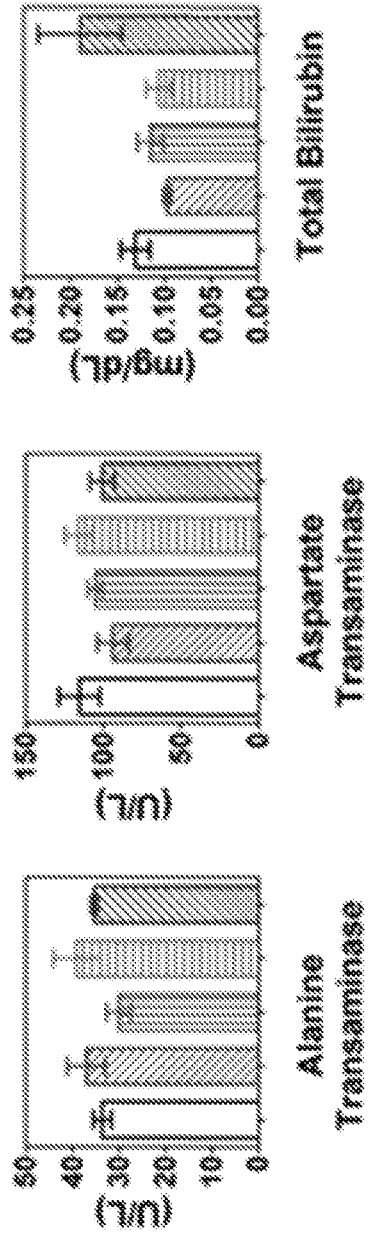
Figure 24B:
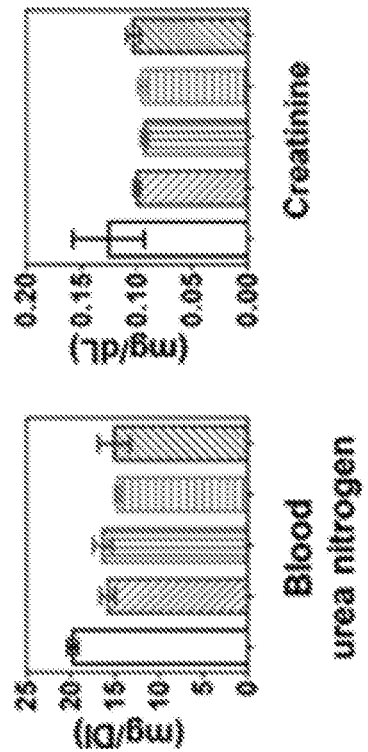
Figure 24C:
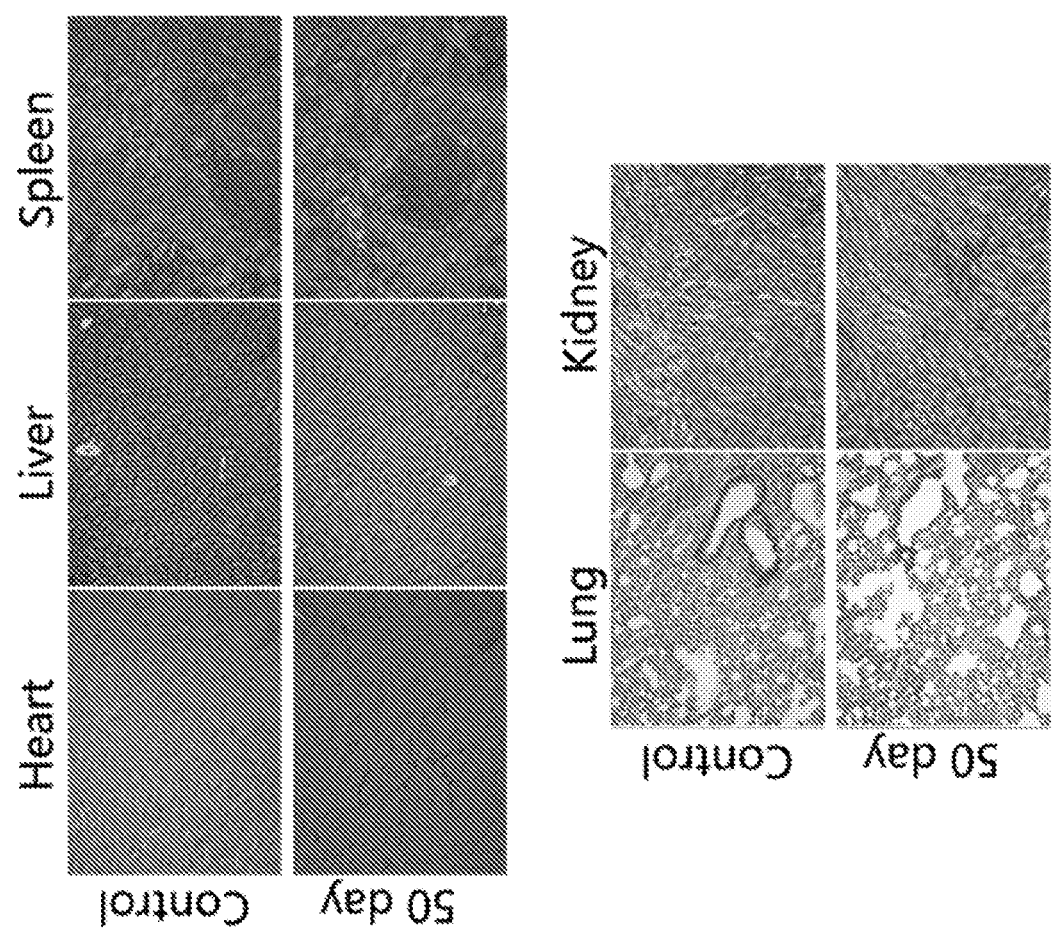
FIG. 24(C) shows representative H&E stained images of major organs from control mice and PPNs administrated (2 mg/kg, calculated on porphyrin) mice at 50 days.

In vivo toxicity evaluation. The potential toxicity of PPNs and the related formulations was assessed in all treated mice. The body weight change, blood cell counts and serum chemistry including renal and hepatic function panels were monitored. Compared to the PBS control group, no obvious body weight loss was observed in all groups (FIG. 24a). 5 days after the last dose on day 15, the blood samples were collected for blood cell counts and serum chemistry analysis. From the results shown in FIG. 24b, the renal and hepatic functions of the mice including ALT, AST, BUN and Cre were generally within the normal ranges, with the exception of elevated total bilirubin in the combination group, which was only one time out of the upper range of normal. Red blood cell counts, hemoglobin, platelets and attributes were unaffected after 4 doses of treatment. White blood cell counts in the free DOX and PPNs-DOX groups showed certain decrease, whereas they were within the normal range. Compared to the PBS control group, PPNs only group showed no changes of WBC counts. After mice in DOX nanoformulation group and PPNs group reached the end point on day 50, the major organs were resected for histopathological examination. The results indicated that all the examined organs were in good condition (FIG. 24c).

Discussion. Nanomaterials offer a new strategy for cancer diagnosis and therapy by altering pharmacokinetic profile of loaded drugs, reduce systematic toxicity, and improve the therapeutic index. However, the use of these clinically approved nanoformulations has not always achieved significantly improved clinical outcomes. Recently, integration of multimodal diagnostic and therapeutic functions within a single nanoparticle has been a trend in developing new generation of nanoparticles. Inorganic nanoparticles have been extensively explored for this application on the basis of their unique interaction with light, photodynamic/photothermal therapy, photoacoustic tomography and magnetic resonance imaging. However, concerns regarding biocompatibility and limited drug loading capacity hindered their further clinical applications. In contrast, organic nanoparticles including liposomes and micelles, have achieved broad clinical implementation due to robust long-term safety and effective drug delivery capacity. However, these carrier-based organic nanoparticles can hardly bring about new therapeutic and imaging modalities. In the present study, by using one single building block, PVA-phorphyrin conjugate and a simple and economic "one-pot" approach, fabrication of multifunctional PPNs was accomplished in aqueous solutions. The PPNs showed interesting light-absorbing in the near-infrared region and structure dependent fluorescence self-quenching. Beside their drug delivery function, PPNs could be used as photosensitizers for PDT and PTT, as well as imaging probes for MRI, NIR fluorescence imaging and potentially PET imaging.

Highly biocompatible materials for obtainment of new devices in the biomedical field have drawn great attention. Poly(vinyl alcohol) (PVA), a water-soluble synthetic polymer with simple linear structure, has a well-documented history of biomedical applications, specifically in the form of hydrogel materials and utility in tissue engineering. However, PVA based physical hydrogels failed to appear in the focus of biomedical research due to their hundreds of micrometers in size that largely ruled out nanoscale materials design. Here, PVA-porphyrin conjugates were prepared via one step ester formation, which could self-assemble into micelle-like structure in aqueous solutions, with particle sizes under 50 nm. A variety of hydrophobic drugs and imaging agents could be incorporated during the nanoparticle formation via self-assembly. With well-defined chemical structure, uniform size and size distribution, excellent drug loading efficiency and biocompatibility, the PVA-porphyrin-based nanoparticles offer unprecedented opportunities for bioimaging and therapeutic applications.

PDT and PTT have shown great promise for the treatment of human diseases. In PDT and PTT, photosensitizers are needed for the light energy conversion. So far, most of the PTT agents are based on inorganic nanomaterials including gold nanoparticles, and carbon nanotubes, which demonstrate much larger absorption coefficient in the NIR regions in contrast to the monomeric chromophores. In the present study, PPNs were developed to use as organic PTT agents as a result of the unique structure-based highly self-quenching properties of porphyrin, showing comparable photothermal efficiency to inorganic PTT agents. In our animal study, PPNs mediated PTT achieved the best overall efficacy in treating ovarian cancers on a SKOV-3 xenograft nude-mice model. Furthermore, the use of PDT in combination with chemotherapy could reinforce the therapeutic efficacy and lessen the side effects, as PDT has been demonstrated to function synergistically with chemotherapy in vitro. Here, in an in vivo system, the combination of PDT and chemotherapy, mediated by doxorubicin-loaded PPNs (DOX-PPNs), produced more pronounced synergistic effect on SKOV-3 xenograft-bearing mice than the sum of the individual therapies. It is beneficial to monitor the biodistribution, tumor accumulation of drug molecules as well as the tumor response after treatments. Therefore, imaging-guided drug delivery and therapy opens up possibilities for real personalized nanomedicine. Based on the intrinsic metal chelation ability of porphyrin, gadolinium-chelated PPNs (Gd-PPNs) achieved great MRI $T_1$ enhancement in vitro and in vivo. Furthermore, dual-modality NIR/MRI enabled by Gd-PPNs were used to noninvasively image in vivo PPNs accumulation in tumor sites and observe tumor growth after PTT in real time. Therefore, this multifunctional nanoplatform was able to integrate diagnostic and therapeutic unites in a synergistic fashion to achieve multiple modalities of imaging and therapy, as well as imaging-guided therapy.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A nanoparticle comprising:
   at least one poly(vinyl alcohol) (PVA) having a molecular weight of from about 10 kDa to about 200 kDa, substituted with one or more moieties of
   a therapeutic agent having a boronic acid moiety, wherein the therapeutic agent is covalently linked to the PVA via a boronate ester bond,
   wherein the PVA has a structure according to formula I:

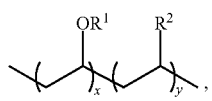
(I)

wherein:
   each R' is independently selected from the group consisting of H and a moiety according to formula Ia:

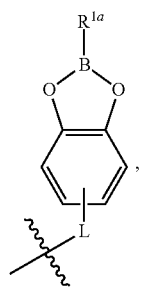
(Ia)

wherein L is a linking moiety and $R^{1a}$ is a therapeutic moiety, provided that at least one R' is H and at least one R' is other than H;

each $R^2$ is independently selected from the group consisting of —OH, a cellular targeting moiety, and an imaging moiety, or any two adjacent $R^2$ moieties are taken together to form a cellular targeting moiety or an imaging moiety;

subscript x is an integer of from about 1 to about 1200, and subscript y is an integer of from 0 to about 3800, wherein the sum of x and y is an integer of from about 200 to about 5000, and the x and y repeating units are randomly distributed in the PVA.

2. The nanoparticle of claim 1, wherein the therapeutic agent moiety is selected from the group consisting of a proteasome inhibitor, a serine protease inhibitor, a β-lactamase inhibitor, and an arginase inhibitor.

3. The nanoparticle of claim 1, wherein each $R^{1a}$ is independently selected from the group consisting of:

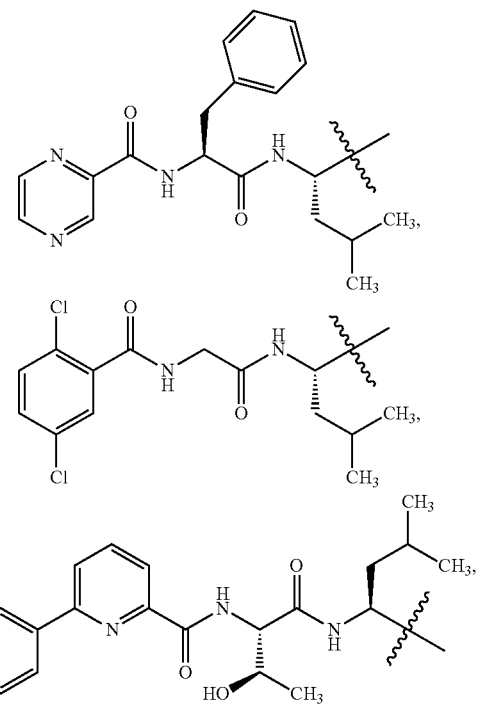

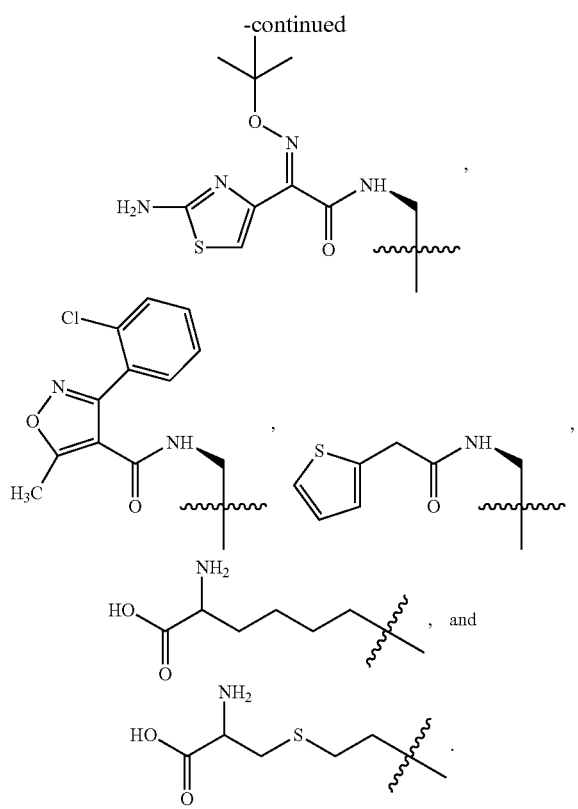

4. The nanoparticle of claim 1, further comprising a drug encapsulated in the nanoparticle.

5. The nanoparticle of claim 1, wherein each $R^2$ is a moiety according to formula IVa

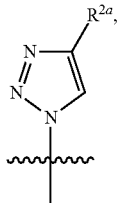

or any two adjacent $R^2$ moieties are taken together to form a moiety according to formula IVb (IVb)

wherein each $R^{2a}$ is independently selected from the group consisting of a cellular targeting moiety and an imaging moiety.

6. The nanoparticle of claim 5, wherein each cellular targeting moiety is independently selected from the group consisting of an antibody, a peptidomimetic moiety, a folic acid moiety, and a peptide.

7. The nanoparticle of claim 5, wherein each cellular targeting moiety is independently selected from the group consisting of LLP2A, bombesin, LXY1, LXY3, LXY4, LXY30, LXW7, O A02, luteinizing-hormone-releasing hormone (LHRH), a melanocyte-stimulating hormone (MSH), folic acid, prostate-specific membrane antigen (PSMA)-targeted ligand, and a PSMA-targeted antibody.

8. The nanoparticle of claim 5, wherein the imaging moiety comprises a fluorophore.

9. The nanoparticle of claim 1, further comprising a branched polymeric crosslinker having from 2 to 4 branches and one boronic acid moiety per branch.

10. A method of treating a disease via photodynamic or photothermal therapy, comprising administering to a subject in need thereof a therapeutically effective amount of a nanoparticle of claim 1, and exposing the subject to radiation, thereby treating the disease via photodynamic or photothermal therapy.

11. A method of detecting a tumor in a subject, comprising:
    administering to the subject an effective amount of a nanoparticle of claim 1; and
    detecting the tumor using an imaging modality selected from the group consisting of fluorescence imaging, magnetic resonance imaging, and positron emission tomography.

* * * * *